US009241916B2

(12) United States Patent
Sinclair et al.

(10) Patent No.: US 9,241,916 B2
(45) Date of Patent: *Jan. 26, 2016

(54) COGNITIVE PERFORMANCE WITH SIRTUIN ACTIVATORS

(75) Inventors: David A. Sinclair, West Roxbury, MA (US); Li-Huei Tsai, Cambridge, MA (US); Andre Fischer, Goettingen (DE)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/955,680

(22) Filed: Dec. 13, 2007

(65) Prior Publication Data

US 2008/0194803 A1 Aug. 14, 2008

Related U.S. Application Data

(63) Continuation-in-part of application No. PCT/US2006/023239, filed on Jun. 14, 2006.

(60) Provisional application No. 60/690,306, filed on Jun. 14, 2005, provisional application No. 60/702,236, filed on Jul. 25, 2005.

(51) Int. Cl.

| | |
|---|---|
| *A01N 37/18* | (2006.01) |
| *A61K 38/00* | (2006.01) |
| *C07H 21/04* | (2006.01) |
| *A61K 31/122* | (2006.01) |
| *A61K 31/015* | (2006.01) |
| *A61K 31/05* | (2006.01) |
| *A61K 31/352* | (2006.01) |
| *A61K 31/415* | (2006.01) |
| *A61K 31/473* | (2006.01) |
| *A61K 31/519* | (2006.01) |

(52) U.S. Cl.
CPC ............ *A61K 31/122* (2013.01); *A61K 31/015* (2013.01); *A61K 31/05* (2013.01); *A61K 31/352* (2013.01); *A61K 31/415* (2013.01); *A61K 31/473* (2013.01); *A61K 31/519* (2013.01); *G01N 2333/98* (2013.01); *G01N 2800/2814* (2013.01)

(58) Field of Classification Search
None
See application file for complete search history.

(56) References Cited

U.S. PATENT DOCUMENTS

| | | |
|---|---|---|
| 4,591,600 A | 5/1986 | Creuzet et al. |
| 4,598,089 A | 7/1986 | Hadvary et al. |
| 5,500,367 A | 3/1996 | Hain et al. |
| 5,689,046 A | 11/1997 | Schroder et al. |
| 5,689,047 A | 11/1997 | Hain et al. |
| 5,747,536 A | 5/1998 | Cavazza |
| 5,827,898 A | 10/1998 | Khandwala et al. |
| 5,874,399 A | 2/1999 | Samal |
| 5,874,444 A | 2/1999 | West |
| 5,945,106 A | 8/1999 | Sinnott |
| 5,985,647 A | 11/1999 | Schroder et al. |
| 6,008,260 A | 12/1999 | Pezzuto et al. |
| 6,020,129 A | 2/2000 | Schroder et al. |
| 6,022,901 A | 2/2000 | Goodman |
| 6,048,903 A | 4/2000 | Toppo |
| 6,063,820 A | 5/2000 | Cavazza |
| 6,063,988 A | 5/2000 | Hain et al. |
| 6,080,701 A | 6/2000 | Jeandet et al. |
| 6,087,385 A | 7/2000 | Pershadsingh et al. |
| 6,124,125 A | 9/2000 | Kemp et al. |
| 6,132,740 A | 10/2000 | Hu |
| 6,147,121 A | 11/2000 | Breton et al. |
| 6,184,248 B1 | 2/2001 | Lee et al. |
| 6,190,716 B1 | 2/2001 | Galbreath, Jr. |
| 6,197,834 B1 | 3/2001 | Docherty |
| 6,211,247 B1 | 4/2001 | Goodman |
| 6,245,814 B1 | 6/2001 | Nag et al. |
| 6,264,995 B1 | 7/2001 | Newmark et al. |
| 6,270,780 B1 | 8/2001 | Carson et al. |
| 6,300,377 B1 | 10/2001 | Chopra |
| 6,319,523 B1 | 11/2001 | Zhou |
| 6,331,633 B1 | 12/2001 | Neogi et al. |
| 6,333,441 B1 | 12/2001 | Sato et al. |
| 6,355,692 B2 | 3/2002 | Docherty |
| 6,358,517 B1 | 3/2002 | Pillai et al. |
| 6,361,815 B1 | 3/2002 | Zheng et al. |
| 6,368,617 B1 | 4/2002 | Hastings et al. |
| 6,387,416 B1 | 5/2002 | Newmark et al. |
| 6,410,596 B1 | 6/2002 | Hopp et al. |
| 6,414,037 B1 | 7/2002 | Pezzuto et al. |
| 6,416,806 B1 | 7/2002 | Zhou |
| 6,423,747 B1 | 7/2002 | Lanzendorfer et al. |

(Continued)

FOREIGN PATENT DOCUMENTS

| | | |
|---|---|---|
| DE | 102 30 961 A1 | 2/2004 |
| EP | 1 064 931 A1 | 1/2001 |

(Continued)

OTHER PUBLICATIONS

Welsh, 1999, Current Opinion in Mol. Therapeutics, 1 (4), pp. 464-470.*
Quin et al., J. Biol. Chem., 2006, 281(31):21745-54.*
Chen et al., J. Biol. Chem., 2005, 280(48):40364-74.*
Michan et al., J. Neurosci., 2010, 30(29):9695-707.*
[No Author Listed] Grape expectations. Boston Globe Editorial. Aug. 29, 2003. 1 page.
[No Author Listed] Guarente Describes Investigation into Longevity Gene at Dean's Distinguished Lecture Series, Harvard Public Health Now. Feb. 20, 2004:1-3.

(Continued)

*Primary Examiner* — Olga N Chernyshev
(74) *Attorney, Agent, or Firm* — Wolf, Greenfield & Sacks, P.C.

(57) ABSTRACT

Provided herein are methods and compositions for enhancing the cognitive performance of a subject in need thereof. A method may include administering to a subject an agent that increases the level of protein or activity of a sirtuin, such as SIRT1.

6 Claims, 5 Drawing Sheets

(56) References Cited

U.S. PATENT DOCUMENTS

| | | | |
|---|---|---|---|
| 6,426,061 B1 | 7/2002 | Li et al. | |
| 6,440,433 B1 | 8/2002 | Breton et al. | |
| 6,448,450 B1 | 9/2002 | Nag et al. | |
| 6,469,055 B2 | 10/2002 | Lee et al. | |
| 6,475,530 B1 | 11/2002 | Kuhrts | |
| 6,479,466 B1 | 11/2002 | Redfield et al. | |
| 6,486,203 B1 | 11/2002 | Dannenberg | |
| 6,500,451 B2 | 12/2002 | Adams | |
| 6,515,020 B1 * | 2/2003 | Cavazza | 514/547 |
| 6,537,969 B1 | 3/2003 | Blass | |
| 6,541,522 B2 | 4/2003 | Inman et al. | |
| 6,544,564 B1 | 4/2003 | Farley | |
| 6,552,085 B2 | 4/2003 | Inman et al. | |
| 6,552,213 B1 | 4/2003 | Deshpande et al. | |
| 6,572,882 B1 | 6/2003 | Vercauteren et al. | |
| 6,573,299 B1 | 6/2003 | Petrus | |
| 6,576,660 B1 | 6/2003 | Liao et al. | |
| 6,605,296 B1 | 8/2003 | Stuckler | |
| 6,615,843 B2 | 9/2003 | Pera | |
| 6,624,197 B1 | 9/2003 | Nag et al. | |
| 6,638,543 B2 | 10/2003 | Kang et al. | |
| 6,638,545 B1 | 10/2003 | Rombi | |
| 6,656,925 B2 | 12/2003 | Petrus | |
| 6,844,163 B1 | 1/2005 | Matsuzawa et al. | |
| 6,964,969 B2 * | 11/2005 | McCleary | 514/283 |
| 7,544,497 B2 | 6/2009 | Sinclair et al. | |
| 7,763,588 B2 | 7/2010 | Van Praag et al. | |
| 7,977,049 B2 | 7/2011 | Sinclair | |
| 8,017,634 B2 | 9/2011 | Sinclair et al. | |
| 8,242,171 B2 | 8/2012 | Sinclair | |
| 2001/0020043 A1 | 9/2001 | Docherty | |
| 2001/0039296 A1 | 11/2001 | Bagchi et al. | |
| 2001/0056071 A1 | 12/2001 | Pelliccia et al. | |
| 2002/0002200 A1 | 1/2002 | Nag et al. | |
| 2002/0009482 A1 | 1/2002 | Adams | |
| 2002/0028852 A1 | 3/2002 | Ghai et al. | |
| 2002/0051799 A1 | 5/2002 | Pruche et al. | |
| 2002/0052407 A1 | 5/2002 | Lee et al. | |
| 2002/0058701 A1 | 5/2002 | Inman et al. | |
| 2002/0058707 A1 | 5/2002 | Hopp et al. | |
| 2002/0091087 A1 | 7/2002 | Zhang et al. | |
| 2002/0110604 A1 | 8/2002 | Babish et al. | |
| 2002/0111383 A1 | 8/2002 | Hassen | |
| 2002/0119952 A1 | 8/2002 | Petrus | |
| 2002/0120008 A1 | 8/2002 | Benzer et al. | |
| 2002/0142017 A1 | 10/2002 | Simonnet | |
| 2002/0146424 A1 | 10/2002 | Benza et al. | |
| 2002/0146472 A1 | 10/2002 | Chen et al. | |
| 2002/0148478 A1 | 10/2002 | Pera | |
| 2002/0155075 A1 | 10/2002 | Collington | |
| 2002/0164385 A1 | 11/2002 | Dannenberg et al. | |
| 2002/0173472 A1 | 11/2002 | Pezzuto et al. | |
| 2002/0173549 A1 | 11/2002 | Wurtmann et al. | |
| 2002/0182196 A1 | 12/2002 | McCleary | |
| 2002/0192310 A1 | 12/2002 | Bland et al. | |
| 2003/0004142 A1 | 1/2003 | Prior et al. | |
| 2003/0004143 A1 | 1/2003 | Prior et al. | |
| 2003/0031693 A1 | 2/2003 | Breton et al. | |
| 2003/0044474 A1 | 3/2003 | C. Tao et al. | |
| 2003/0044946 A1 | 3/2003 | Longo | |
| 2003/0054053 A1 | 3/2003 | Young et al. | |
| 2003/0054357 A1 | 3/2003 | Young et al. | |
| 2003/0055108 A1 | 3/2003 | Young | |
| 2003/0055114 A1 | 3/2003 | Young | |
| 2003/0064913 A1 | 4/2003 | Sonis | |
| 2003/0078212 A1 | 4/2003 | Li et al. | |
| 2003/0082116 A1 | 5/2003 | Badejo et al. | |
| 2003/0082203 A1 | 5/2003 | Farley | |
| 2003/0082597 A1 | 5/2003 | Cannon et al. | |
| 2003/0082647 A1 | 5/2003 | Reenan et al. | |
| 2003/0084912 A1 | 5/2003 | Pera | |
| 2003/0086986 A1 | 5/2003 | Bruijn et al. | |
| 2003/0118536 A1 | 6/2003 | Rosenbloom | |
| 2003/0118617 A1 | 6/2003 | Soby et al. | |
| 2003/0124101 A1 | 7/2003 | Gu et al. | |
| 2003/0124161 A1 | 7/2003 | Biatry et al. | |
| 2003/0129247 A1 | 7/2003 | Ju et al. | |
| 2003/0133992 A1 | 7/2003 | Bagchi et al. | |
| 2003/0145354 A1 | 7/2003 | Milkowski et al. | |
| 2003/0149261 A1 | 8/2003 | Schramm et al. | |
| 2003/0152617 A1 | 8/2003 | Yatvin | |
| 2003/0161830 A1 | 8/2003 | Jackson et al. | |
| 2003/0161902 A1 | 8/2003 | Duncan | |
| 2003/0165854 A1 | 9/2003 | Cunningham et al. | |
| 2003/0180719 A1 | 9/2003 | Herget et al. | |
| 2003/0182302 A1 | 9/2003 | Li | |
| 2003/0185912 A1 | 10/2003 | Rosenbloom | |
| 2003/0186898 A1 | 10/2003 | Maurya et al. | |
| 2003/0190337 A1 | 10/2003 | Bissett | |
| 2003/0190381 A1 | 10/2003 | Bland et al. | |
| 2003/0191064 A1 | 10/2003 | Kopke | |
| 2003/0199581 A1 | 10/2003 | Seligson et al. | |
| 2003/0203973 A1 | 10/2003 | Cooper et al. | |
| 2003/0207325 A1 | 11/2003 | Guarente et al. | |
| 2003/0224077 A1 | 12/2003 | Mahe et al. | |
| 2003/0228269 A1 | 12/2003 | DeRosa et al. | |
| 2003/0232782 A1 | 12/2003 | Escalante-Semerena et al. | |
| 2004/0002499 A1 | 1/2004 | Aggarwal | |
| 2004/0005574 A1 | 1/2004 | Guarente et al. | |
| 2004/0009197 A1 | 1/2004 | DeRosa et al. | |
| 2004/0014682 A1 | 1/2004 | Ravagnan et al. | |
| 2004/0014721 A1 | 1/2004 | Hensley et al. | |
| 2004/0015020 A1 | 1/2004 | Deshpande et al. | |
| 2004/0018987 A1 | 1/2004 | Hoffman et al. | |
| 2004/0028607 A1 | 2/2004 | Verdin et al. | |
| 2004/0067894 A1 | 4/2004 | Carola et al. | |
| 2004/0209952 A1 | 10/2004 | Kim et al. | |
| 2004/0249938 A1 | 12/2004 | Bunch | |
| 2004/0259938 A1 | 12/2004 | Nag et al. | |
| 2004/0265861 A1 | 12/2004 | Goldfarb | |
| 2005/0004046 A1 | 1/2005 | Praag et al. | |
| 2005/0020511 A1 | 1/2005 | Li et al. | |
| 2005/0038125 A1 | 2/2005 | Smit et al. | |
| 2005/0049208 A1 | 3/2005 | Kaufmann et al. | |
| 2005/0070470 A1 | 3/2005 | Coy et al. | |
| 2005/0096256 A1 | 5/2005 | Sinclair | |
| 2005/0107338 A1 | 5/2005 | Seidman | |
| 2005/0136429 A1 | 6/2005 | Guarente et al. | |
| 2005/0136537 A1 | 6/2005 | Sinclair et al. | |
| 2005/0171027 A1 | 8/2005 | Sinclair et al. | |
| 2005/0267023 A1 | 12/2005 | Sinclair et al. | |
| 2006/0002914 A1 | 1/2006 | Milbrandt et al. | |
| 2006/0014705 A1 | 1/2006 | Howitz et al. | |
| 2006/0025337 A1 | 2/2006 | Sinclair et al. | |
| 2006/0084085 A1 | 4/2006 | Sinclair et al. | |
| 2006/0084135 A1 | 4/2006 | Howitz et al. | |
| 2006/0111435 A1 | 5/2006 | Sinclair et al. | |
| 2006/0229265 A1 | 10/2006 | Milburn et al. | |
| 2006/0257502 A1 | 11/2006 | Liu | |
| 2006/0276393 A1 | 12/2006 | Milburn et al. | |
| 2006/0276416 A1 | 12/2006 | Sinclair et al. | |
| 2007/0105109 A1 * | 5/2007 | Geesaman et al. | 435/6 |
| 2007/0160586 A1 | 7/2007 | Alt et al. | |
| 2008/0194803 A1 | 8/2008 | Sinclair et al. | |
| 2009/0117543 A1 | 5/2009 | Sinclair | |
| 2010/0035885 A1 | 2/2010 | Sinclair et al. | |
| 2011/0082189 A1 | 4/2011 | Sinclair | |
| 2012/0021924 A1 | 1/2012 | Sinclair | |
| 2012/0022013 A1 | 1/2012 | Sinclair | |
| 2012/0029065 A1 | 2/2012 | Sinclair et al. | |
| 2012/0164670 A1 | 6/2012 | Hubbard et al. | |

FOREIGN PATENT DOCUMENTS

| | | | |
|---|---|---|---|
| EP | 1 440 688 A1 | 7/2004 | |
| JP | 2001-048722 A | 2/2001 | |
| JP | 2002-527389 A | 8/2002 | |
| JP | 2003-137727 A | 5/2003 | |
| JP | 2004-18376 | 1/2004 | |
| WO | WO 97/07790 A1 | 3/1997 | |
| WO | WO 98/41113 A2 | 9/1998 | |
| WO | WO 98/57928 A1 | 12/1998 | |
| WO | WO 99/59561 * | 11/1999 | A61K 31/00 |
| WO | WO 99/59561 A2 | 11/1999 | |

(56) References Cited

FOREIGN PATENT DOCUMENTS

| | | |
|---|---|---|
| WO | WO 00/21526 A1 | 4/2000 |
| WO | WO 00/53176 A1 | 9/2000 |
| WO | WO 00/59522 A1 | 10/2000 |
| WO | WO 00/69430 A1 | 11/2000 |
| WO | WO 01/98291 A2 | 12/2001 |
| WO | WO 02/13811 A2 | 2/2002 |
| WO | WO 02/14252 A2 | 2/2002 |
| WO | WO 02/17959 A2 | 3/2002 |
| WO | WO 02/49575 A2 | 6/2002 |
| WO | WO 02/49994 A2 | 6/2002 |
| WO | WO 02/102981 A2 | 12/2002 |
| WO | WO 03/031404 A2 | 4/2003 |
| WO | WO 03/037315 A1 | 5/2003 |
| WO | WO 03/039535 A1 | 5/2003 |
| WO | WO 03/103583 A2 | 12/2003 |
| WO | WO 2004/016726 A2 | 2/2004 |
| WO | WO 2004/041758 A2 | 5/2004 |
| WO | WO 2004/105517 A1 | 12/2004 |
| WO | WO 2005/002527 A2 | 1/2005 |
| WO | WO 2005/002555 A2 | 1/2005 |
| WO | WO 2005/002672 A2 | 1/2005 |
| WO | WO 2005/004814 A2 | 1/2005 |
| WO | WO 2005/026112 A2 | 3/2005 |
| WO | WO 2005/053609 A2 | 6/2005 |
| WO | WO 2006/034485 A2 | 3/2006 |
| WO | WO 2006/068656 A2 | 6/2006 |
| WO | WO 2006/076681 A2 | 7/2006 |
| WO | WO 2006/078941 A2 | 7/2006 |
| WO | WO 2006/094235 A1 | 9/2006 |
| WO | WO 2006/096780 A2 | 9/2006 |
| WO | WO 2006/138418 A2 | 12/2006 |

OTHER PUBLICATIONS

[No Author Listed] The latest research on caloric restriction and animal and human longevity. American Federation for Aging Research. Jul. 8, 2003. 2 pages.

Aguilaniu et al., Asymmetric inheritance of oxidatively damaged proteins during cytokinesis. Science. Mar. 14, 2003;299(5613):1751-3. Epub Feb. 27, 2003.

Aiston et al., Glucose 6-phosphate causes translocation of phosphorylase in hepatocytes and inactivates the enzyme synergistically with glucose. Biochem J. Jan. 1, 2004;377(Pt 1):195-204.

Anderson et al., Manipulation of a nuclear NAD+ salvage pathway delays aging without altering steady-state NAD+ levels. J Biol Chem. May 24, 2002;277(21):18881-90. Epub Mar. 7, 2002.

Anderson et al., Nicotinamide and PNC1 govern lifespan extension by calorie restriction in Saccharomyces cerevisiae. Nature. May 8, 2003;423(6936):181-5.

Anderson et al., Yeast life-span extension by calorie restriction is independent of NAD fluctuation. Science. Dec. 19, 2003;302(5653):2124-6. Epub Nov. 6, 2003.

Araki et al., Increased nuclear NAD biosynthesis and SIRT1 activation prevent axonal degeneration. Science. Aug. 13, 2004;305(5686):1010-3.

Bagchi et al., Phytoestrogen, resveratrol and women's health. Research Communications in Pharmacology and Toxicology. 2000;5(1&2). XP-001018765.

Bastianetto et al., Reversatrol and red wine constituents: evaluation of their neuroprotective properties. Pharmaceutical News. 2001;8(5):33-38.

Baur et al., Resveratrol improves health and survival of mice on a high-calorie diet. Nature Articles. Nature Publishing Group, 2006:1-6.

Baur et al., Therapeutic potential of resveratrol: the in vivo evidence. Nat Rev Drug Discov. Jun. 2006;5(6):493-506. Epub May 26, 2006. Review.

Bedalov et al., Identification of a small molecule inhibitor of Sir2p. Proc Natl Acad Sci U S A. Dec. 18, 2001;98(26):15113-8.

Bedalov et al., Neuroscience. NAD to the rescue. Science. Aug. 13, 2004;305(5686):954-5.

Benguria et al., Sir2p suppresses recombination of replication forks stalled at the replication fork barrier of ribosomal DNA in Saccharomyces cerevisiae. Nucleic Acids Res. Feb. 1, 2003;31(3):893-8.

Bergeron et al., Effect of 5-aminoimidazole-4-carboxamide-1-beta-D-ribofuranoside infusion on in vivo glucose and lipid metabolism in lean and obese Zucker rats. Diabetes. May 2001;50(5):1076-82.

Berkow et al., Merck Manual of Diagnosis and Therapy. Merck & Co, US. 1987:2392. XP002141064.

Bieganowski et al., Discoveries of nicotinamide riboside as a nutrient and conserved NRK genes establish a Preiss-Handler independent route to NAD+ in fungi and humans. Cell. May 14, 2004;117(4):495-502.

Bitterman et al., Inhibition of silencing and accelerated aging by nicotinamide, a putative negative regulator of yeast sir2 and human SIRT1. J Biol Chem. Nov. 22, 2002;277(47):45099-107. Epub Sep. 23, 2002.

Bitterman et al., Longevity regulation in Saccharomyces cerevisiae: linking metabolism, genome stability, and heterochromatin. Microbiol Mol Biol Rev. Sep. 2003;67(3):376-99, table of contents. Review.

Borra et al., Mechanism of human SIRT1 activation by resveratrol. J Biol Chem. Apr. 29, 2005;280(17):17187-95. Epub Mar. 4, 2005.

Brachmann et al., The SIR2 gene family, conserved from bacteria to humans, functions in silencing, cell cycle progression, and chromosome stability. Genes Dev. Dec. 1, 1995;9(23):2888-902.

Brandolini et al., Capillary electrophoresis determination, synthesis, and stability of resveratrol and related 3-O-beta-D-glucopyranosides. J Agric Food Chem. Dec. 4, 2002;50(25):7407-11.

Brehm, The skinny of fat: MIT researchers establish first link between eating and aging. Massachusetts Institute of Technology. Jun. 2, 2004. 2 pages.

Brunet et al., Stress-dependent regulation of FOXO transcription factors by the SIRT1 deacetylase. Science. Mar. 26, 2004;303(5666):2011-5. Epub Feb. 19, 2004.

Bryk et al., Transcriptional silencing of Ty1 elements in the RDN1 locus of yeast. Genes Dev. Jan. 15, 1997;11(2):255-69.

Campisi, Aging, chromatin, and food restriction—connecting the dots. Science. Sep. 22, 2000;289(5487):2062-3.

Chua et al., Mammalian SIRT1 limits replicative life span in response to chronic genotoxic stress. Cell Metab. Jul. 2005;2(1):67-76.

Cohen et al., Acetylation of the C terminus of Ku70 by CBP and PCAF controls Bax-mediated apoptosis. Mol Cell. Mar. 12, 2004;13(5):627-38.

Cohen et al., Calorie restriction promotes mammalian cell survival by inducing the SIRT1 deacetylase. Science. Jul. 16, 2004;305(5682):390-2. Epub Jun. 17, 2004.

Coronado et al., Alfalfa Root Flavonoid Production Is Nitrogen Regulated. Plant Physiol. Jun. 1995;108(2):533-542.

Couzin, Scientific community. Aging research's family feud. Science. Feb. 27, 2004;303(5662):1276-9.

Dai et al., SIRT1 activation by small molecules: kinetic and biophysical evidence for direct interaction of enzyme and activator. J Biol Chem. Oct. 22, 2010;285(43):32695-703. Epub Aug. 11, 2010.

Dajas et al., Cell culture protection and in vivo neuroprotective capacity of flavonoids. Neurotox Res. 2003;5(6):425-32. Abstract Only.

De Cabo et al., An in vitro model of caloric restriction. Exp Gerontol. Jun. 2003;38(6):631-9.

Defossez et al., Elimination of replication block protein Fob1 extends the life span of yeast mother cells. Mol Cell. Apr. 1999;3(4):447-55.

Denu, Linking chromatin function with metabolic networks: Sir2 family of NAD(+)-dependent deacetylases. Trends Biochem Sci. Jan. 2003;28(1):41-8. Review.

Dong, Molecular mechanism of the chemopreventive effect of resveratrol. Mutat Res. Feb.-Mar. 2003;523-524:145-50. Review.

Ferguson, Role of plant polyphenols in genomic stability. Mutat Res. 2002;475:89-111.

Flam, PA scientists may be onto antiaging compound. Philadelphia Inquirer. Sep. 10, 2003. 3 pages.

Frye, Phylogenetic classification of prokaryotic and eukaryotic Sir2-like proteins. Biochem Biophys Res Commun. Jul. 5, 2000;273(2):793-8.

Glossmann et al., Quercetin inhibits tyrosine phosphorylation by the cyclic nucleotide-independent, transforming protein kinase, pp60src. Naunyn Schmiedebergs Arch Pharmacol. Aug. 1981;317(1):100-2.

(56) References Cited

OTHER PUBLICATIONS

Gottlieb et al., A new role for a yeast transcriptional silencer gene, SIR2, in regulation of recombination in ribosomal DNA. Cell. Mar. 10, 1989;56(5):771-6.
Graefe et al., Pharmacokinetics and bioavailability of the flavonol quercetin in humans. Int J Clin Pharmacol Ther. May 1999;37(5):219-33. Review.
Grozinger et al., Identification of a class of small molecule inhibitors of the sirtuin family of NAD-dependent deacetylases by phenotypic screening. J Biol Chem. Oct. 19, 2001;276(42):38837-43. Epub Aug. 1, 2001.
Guarente et al., Genetic pathways that regulate ageing in model organisms. Nature. Nov. 9, 2000;408(6809):255-62. Review.
Hekimi et al., Genetics and the specificity of the aging process. Science. Feb. 28, 2003;299(5611):1351-4. Review.
Hendrickson, A dietary magic bullet? Harvard team says pill will fight effects of high-fat eating. The Journal of New England Technology, Mass. High Tech. Dec. 8-14, 2003.
Herzenberg et al., The history and future of the fluorescence activated cell sorter and flow cytometry: a view from Stanford. Clin Chem. Oct. 2002;48(10):1819-27.
Hildebrandt, Pschyrembel Klinisches Woerterbuch. 1998:47-49. XP002141063.
Hirao et al., Identification of selective inhibitors of NAD+-dependent deacetylases using phenotypic screens in yeast. J Biol Chem. Dec. 26, 2003;278(52):52773-82. Epub Oct. 8, 2003.
Holla et al., New bis-aminomercaptotriazoles and bis-triazolothiadiazoles as possible anticancer agents. Eur J Med Chem. Jun. 2002;37(6):511-7.
Holzenberger et al., IGF-1 receptor regulates lifespan and resistance to oxidative stress in mice. Nature. Jan. 9, 2003;421(6919):182-7. Epub Dec. 4, 2002.
Howitz et al., Small molecule activators of sirtuins extend Saccharomyces cerevisiae lifespan. Nature. Sep. 11, 2003;425(6954):191-6. Epub Aug. 24, 2003.
Hu et al., Antioxidants may contribute in the fight against ageing: an in vitro model. Mech Ageing Dev. Dec. 20, 2000;121(1-3):217-30.
Ignatowicz et al., Resveratrol, a natural chemopreventive agent against degenerative diseases. Pol J Pharmacol. Nov.-Dec. 2001;53(6):557-69. Review.
Imai et al., Transcriptional silencing and longevity protein Sir2 is an NAD-dependent histone deacetylase. Nature. Feb. 17, 2000;403(6771):795-800.
Jang et al., Cancer chemopreventive activity of resveratrol, a natural product derived from grapes. Science. Jan. 10, 1997;275(5297):218-20.
Jazwinski, Metabolic control and gene dysregulation in yeast aging. Ann N Y Acad Sci. Jun. 2000;908:21-30. Review.
Jia et al., Pre-B cell colony-enhancing factor inhibits neutrophil apoptosis in experimental inflammation and clinical sepsis. J Clin Invest. May 2004;113(9):1318-27.
Johnstone et al., Histone deacetylase inhibitors in cancer therapy: is transcription the primary target? Cancer Cell. Jul. 2003;4(1):13-8. Review.
Kaeberlein et al., Grapes versus gluttony. Nature News & Views: Nature Publishing Group, 2006:1-2.
Kaeberlein et al., High osmolarity extends life span in Saccharomyces cerevisiae by a mechanism related to calorie restriction. Mol Cell Biol. Nov. 2002;22(22):8056-66.
Kaeberlein et al., Substrate-specific activation of sirtuins by resveratrol. J Biol Chem. Apr. 29, 2005;280(17):17038-45. Epub Jan. 31, 2005.
Kaeberlein et al., The SIR2/3/4 complex and SIR2 alone promote longevity in Saccharomyces cerevisiae by two different mechanisms. Genes Dev. Oct. 1, 1999;13(19):2570-80.
Kenyon, A conserved regulatory system for aging. Cell. Apr. 20, 2001;105(2):165-8. Review.
Khanna et al., Dermal wound healing properties of redox-active grape seed proanthocyanidins. Free Radic Biol Med. Oct. 15, 2002;33(8):1089-96.

Kim et al., SIRT1 deacetylase protects against neurodegeneration in models for Alzheimer's disease and amyotrophic lateral sclerosis. EMBO J. Jul. 11, 2007;26(13):3169-79. Epub Jun. 21, 2007.
Kimura, Pharmacological studies on resveratrol. Methods Find Exp Clin Pharmacol. May 2003;25(4):297-310. Review.
Koubova et al., How does calorie restriction work? Genes Dev. Feb. 1, 2003;17(3):313-21. Review.
Kris-Etherton et al., Bioactive compounds in foods: their role in the prevention of cardiovascular disease and cancer. Am J Med. Dec. 30, 2002;113 Suppl 9B:71S-88S. Review.
Lacey, Glenn launches labs for aging research. Harvard Medical School Communications, Harvard University Gazette. Mar. 17, 2005.
Lamming et al., Small molecules that regulate lifespan: evidence for xenohormesis. Mol Microbiol. Aug. 2004;53(4):1003-9. Review.
Landry et al., The silencing protein SIR2 and its homologs are NAD-dependent protein deacetylases. Proc Natl Acad Sci U S A. May 23, 2000;97(11):5807-11.
Langley et al., Human SIR2 deacetylates p53 and antagonizes PML/p53-induced cellular senescence. EMBO J. May 15, 2002;21(10):2383-96.
Laurenson et al., Silencers, silencing, and heritable transcriptional states. Microbiol Rev. Dec. 1992;56(4):543-60. Review.
Ledford, Much ado about ageing. Nature. Mar. 2010;464:480-481.
Lin et al., Requirement of NAD and SIR2 for life-span extension by calorie restriction in Saccharomyces cerevisiae. Science. Sep. 22, 2000;289(5487):2126-8.
Liu et al., Antimalarial alkoxylated and hydroxylated chalcones [corrected]: structure-activity relationship analysis. J Med Chem. Dec. 6, 2001;44(25):4443-52. Erratum in: J Med Chem Apr. 11, 2002;45(8):1734.
Longo et al., Evolutionary medicine: from dwarf model systems to healthy centenarians? Science. Feb. 28, 2003;299(5611):1342-6. Review.
Luo et al., Negative control of p53 by Sir2alpha promotes cell survival under stress. Cell. Oct. 19, 2001;107(2):137-48.
Mai et al., Histone deacetylation in epigenetics: an attractive target for anticancer therapy. Med Res Rev. May 2005;25(3):261-309. Review.
Marcotte et al., Fluorescence assay of SIRT protein deacetylases using an acetylated peptide substrate and a secondary trypsin reaction. Anal Biochem. Sep. 1, 2004;332(1):90-9.
Michael, Compound in blueberries may prevent heart disease and type 2 diabetes. Healthy Living NYC. 2005. 4 pages.
Middleton et al., The effects of plant flavonoids on mammalian cells: implications for inflammation, heart disease, and cancer. Pharmacol Rev. Dec. 2000;52(4):673-751. Review.
Mills et al., MEC1-dependent redistribution of the Sir3 silencing protein from telomeres to DNA double-strand breaks. Cell. May 28, 1999;97(5):609-20.
Monod et al., On the nature of allosteric transitions: a plausible model. J Mol Biol. May 1965;12:88-118.
Morino et al., Specific regulation of HSPs in human tumor cell lines by flavonoids. In Vivo. May-Jun. 1997;11(3):265-70.
Motta et al., Mammalian SIRT1 represses forkhead transcription factors. Cell. Feb. 20, 2004;116(4):551-63.
Nemoto et al., Nutrient availability regulates SIRT1 through a forkhead-dependent pathway. Science. Dec. 17, 2004;306(5704):2105-8.
Nicolini et al., Anti-apoptotic effect of trans-resveratrol on paclitaxel-induced apoptosis in the human neuroblastoma SH-SY5Y cell line. Neurosci Lett. Apr. 13, 2001;302(1):41-4.
Nothwehr et al., A retention factor keeps death at bay. Nat Cell Biol. Apr. 2003;5(4):281-3. Review.
Ognjanovic et al., Genomic organization of the gene coding for human pre-B-cell colony enhancing factor and expression in human fetal membranes. J Mol Endocrinol. Apr. 2001;26(2):107-17.
Oliver et al., Inhibition of mast cell Fc epsilon R1-mediated signaling and effector function by the Syk-selective inhibitor, piceatannol. J Biol Chem. Nov. 25, 1994;269(47):29697-703.
Pacholec et al., SRT1720, SRT2183 and SRT1460 do not activate Sirt1 with native substrates. Poster 30. FASEB Summer Research Conferences. Arizona. Jun. 21-26, 2009.

(56) References Cited

OTHER PUBLICATIONS

Pacholec et al., SRT1720, SRT2183, SRT1460, and resveratrol are not direct activators of SIRT1. J Biol Chem. Mar. 12, 2010;285(11):8340-51. Epub Jan. 8, 2010. Supplemental Materials Included.

Pandey et al., Analysis of histone acetyltransferase and histone deacetylase families of Arabidopsis thaliana suggests functional diversification of chromatin modification among multicellular eukaryotes. Nucleic Acids Res. Dec. 1, 2002;30(23):5036-55.

Parfitt et al., Antineoplastics and Immunosuppressants. Pharmaceutical Press. London. 1995. 2nd edition. XP002329271.

Park et al., Effects of mutations in DNA repair genes on formation of ribosomal DNA circles and life span in Saccharomyces cerevisiae. Mol Cell Biol. May 1999;19(5):3848-56.

Perez et al., Synthesis and characterization of complexes of p-isopropyl benzaldehyde and methyl 2-pyridyl ketone thiosemicarbazones with Zn(II) and Cd(II) metallic centers. Cytotoxic activity and induction of apoptosis in Pam-ras cells. J Inorg Biochem. Jul. 15, 1999;75(4):255-61.

Picard et al., Sirt1 promotes fat mobilization in white adipocytes by repressing PPAR-gamma. Nature. Jun. 17, 2004;429(6993):771-6. Epub Jun. 2, 2004.

Pont et al., Relation between the chemical structure and the biological activity of hydroxystilbenes against *botrytis cinerea*. J Phytopathology. 1990;130:1-8.

Porcu et al., The emerging therapeutic potential of sirtuin-interacting drugs: from cell death to lifespan extension. Trends Pharmacol Sci. Feb. 2005;26(2):94-103. Review.

Pugh et al., Controlling caloric consumption: protocols for rodents and rhesus monkeys. Neurobiol Aging. Mar.-Apr. 1999;20(2):157-65. Review.

Raffaelli et al., Identification of a novel human nicotinamide mononucleotide adenylyltransferase. Biochem Biophys Res Commun. Oct. 4, 2002;297. Abstract Only.

Regev-Shoshani et al., Glycosylation of resveratrol protects it from enzymic oxidation. Biochem J. Aug. 15, 2003(Pt 1):157-63

Revollo et al., The NAD biosynthesis pathway mediated by nicotinamide phosphoribosyltransferase regulates Sir2 activity in mammalian cells. J Biol Chem. Dec. 3, 2004;279(49):50754-63. Epub Sep. 20, 2004.

Rogina et al., Longevity regulation by Drosophila Rpd3 deacetylase and caloric restriction. Science. Nov. 29, 2002;298(5599):1745.

Samal et al., Cloning and characterization of the cDNA encoding a novel human pre-B-cell colony-enhancing factor. Mol Cell Biol. Feb. 1994;14(2):1431-7.

Sampson, Compound identified in grapes may fight cancer and diabetes. http://prohealth.com. Last Accessed on May 27, 2002. 4 pages.

Sandmeier et al., Telomeric and rDNA silencing in Saccharomyces cerevisiae are dependent on a nuclear NAD(+) salvage pathway. Genetics. Mar. 2002;160(3):877-89.

Sawada et al., Cytoprotective membrane-permeable peptides designed from the Bax-binding domain of Ku70. Nat Cell Biol. Apr. 2003;5(4):352-7.

Sawada et al., Ku70 suppresses the apoptotic translocation of Bax to mitochondria. Nat Cell Biol. Apr. 2003;5(4):320-9. Abstract.

Sharma et al., Chronic treatment with trans resveratrol prevents intracerebroventricular streptozotocin induced cognitive impairment and oxidative stress in rats. Life Sci. Oct. 11, 2002;71(21):2489-98.

Shimokawa et al., Life span extension by reduction of the growth hormone-insulin-like growth factor-1 axis: relation to caloric restriction. FASEB J. Jun. 2003;17(9):1108-9. Epub Apr. 8, 2003.

Sinclair et al., Extrachromosomal rDNA circles—a cause of aging in yeast. Cell. Dec. 26, 1997;91(7):1033-42.

Sinclair, Paradigms and pitfalls of yeast longevity research. Mech Ageing Dev. Apr. 30, 2002;123(8):857-67. Review.

Sinclair, Sirtuins for healthy neurons. Nat Genet. Apr. 2005;37(4):339-40.

Smith et al., A phylogenetically conserved NAD+-dependent protein deacetylase activity in the Sir2 protein family. Proc Natl Acad Sci U S A. Jun. 6, 2000;97(12):6658-63.

Smith et al., An unusual form of transcriptional silencing in yeast ribosomal DNA. Genes Dev. Jan. 15, 1997;11(2):241-54.

Soleas et al., Resveratrol: a molecule whose time has come? and gone? Clin Biochem. Mar. 1997;30(2):91-113. Review.

Solomon et al., Inhibition of SIRT1 catalytic activity increases p53 acetylation but does not alter cell survival following DNA damage. Mol Cell Biol. Jan. 2006;26(1):28-38.

Stojanovic et al., Efficiency and mechanism of the antioxidant action of trans-resveratrol and its analogues in the radical liposome oxidation. Arch Biochem Biophys. Jul. 1, 2001;391(1):79-89.

Subramanian et al., Ku70 acetylation mediates neuroblastoma cell death induced by histone deacetylase inhibitors. Proc Natl Acad Sci U S A. Mar. 29, 2005;102(13):4842-7. Epub Mar. 18, 2005.

Sun et al., The "French Paradox" and beyond: neuroprotective effects of polyphenols. Free Radic Biol Med. Feb. 15, 2002;32(4):314-8. Review.

Tanner et al., Silent information regulator 2 family of NAD-dependent histone/protein deacetylases generates a unique product, 1-O-acetyl-ADP-ribose. Proc Natl Acad Sci U S A. Dec. 19, 2000;97(26):14178-82.

Tanny et al., An enzymatic activity in the yeast sir2 protein that is essential for gene silencing. Cell. 1999;99:735-745.

Tanny et al., Coupling of histone deacetylation to NAD breakdown by the yeast silencing protein Sir2: Evidence for acetyl transfer from substrate to an NAD breakdown product. Proc Natl Acad Sci U S A. Jan. 16, 2001;98(2):415-20. Epub Dec. 26, 2000.

Tatar et al., The endocrine regulation of aging by insulin-like signals. Science. Feb. 28, 2003;299(5611):1346-51. Review.

Tissenbaum et al., Increased dosage of a sir-2 gene extends lifespan in Caenorhabditis elegans. Nature. Mar. 8, 2001;410(6825):227-30.

Tredici et al., Resveratrol, map kinases and neuronal cells: might wine be a neuroprotectant? Drugs Exp Clin Res. 1999;25(2-3):99-103.

Vaziri et al., hSIR2(SIRT1) functions as an NAD-dependent p53 deacetylase. Cell. Oct. 19, 2001;107(2):149-59.

Vergnes et al., Cytoplasmic SIR2 homologue overexpression promotes survival of Leishmania parasites by preventing programmed cell death. Gene. Aug. 21, 2002;296(1-2):139-50.

Wade, Study spurs hope of finding way to increase human life. New York Times. Aug. 25, 2003. 3 pages.

Wood et al., Sirtuin activators mimic caloric restriction and delay ageing in metazoans. Nature. Aug. 5, 2004;430(7000):686-9. Epub Jul. 14, 2004.

Wu et al., Ginkgo biloba extract EGb 761 increases stress resistance and extends life span of Caenorhabditis elegans. Cell Mol Biol (Noisy-le-grand). Sep. 2002;48(6):725-31.

Yoshida et al., Histone deacetylase as a new target for cancer chemotherapy. Cancer Chemother Pharmacol. Aug. 2001;48 Suppl 1:S20-6. Review.

Zern et al., Grape polyphenols decrease plasma triglycerides and cholesterol accumulation in the aorta of ovariectomized guinea pigs. J Nutr. Jul. 2003; 133(7):2268-72.

Zhang et al., Crystal structures of *E. coli* nicotinate mononucleotide adenylyltransferase and its complex with deamido-NAD. Structure. Jan. 2002;10(1):69-79.

Zhao et al., Structural basis for nicotinamide cleavage and ADP-ribose transfer by NAD(+)-dependent Sir2 histone/protein deacetylases. Proc Natl Acad Sci U S A. Jun. 8, 2004;101(23):8563-8. Epub May 18, 2004.

Zhou et al., Role of AMP-activated protein kinase in mechanism of metformin action. J Clin Invest. Oct. 2001;108(8):1167-74.

GENBANK Submission; NCBI, Accession No. BC020691; Strausberg et al.; Jun. 29, 2004.

GENBANK Submission; NCBI, Accession No. NP_005737; Jia et al.; Oct. 28, 2004.

GENBANK Submission; NCBI, Accession No. NP_877591; Jia et al.; Oct. 27, 2004.

Couzin-Frankel, Genetics. Aging genes: the sirtuin story unravels. Science. Dec. 2, 2011;334(6060):1194-8.

Donmez et al., SIRT1 protects against α-synuclein aggregation by activating molecular chaperones. J Neurosci. Jan. 4, 2012;32(1):124-32.

(56) References Cited

OTHER PUBLICATIONS

Donmez et al., SIRT1 suppresses beta-amyloid production by activating the alpha-secretase gene ADAM10. Cell. Jul. 23, 2010;142(2):320-32. Erratum in: Cell. Aug. 6, 2010;142(3):494-5.
Gao et al., A novel pathway regulates memory and plasticity via SIRT1 and miR-134. Nature. Aug. 26, 2010;466(7310):1105-9. Epub Jul. 11, 2010.
Jiang et al., Neuroprotective role of Sirt1 in mammalian models of Huntington's disease through activation of multiple Sirt1 targets. Nature Medicine. Jan. 2012; 18(1):153-9.
Agnivesa; Caraka Samhita- Edited & translated by P.V Sharma, vol. II: Chaukhamba Orientalia, Varanasi, Edn. $5^{th}$ 2000. [ Time of origin 1000 BC-$4^{th}$ century] p. 412. Formulation ID: BP/1834B. Formulation Name: Medhyarasanam—2.
Chang et al., Nuclear envelope dispersion triggered by deregulated CdkS precedes neuronal death. Mol Biol Cell. May 2011;22(9):1452-62. doi:10.1091/mbc.E10-07-0654. Epub Mar. 9, 2011.
Govinda Dasa; Bhaisajya Ratnavali- Edited by Rajeshvaradutta Shastri, Translated by Ambikaduttashastri: Chaukhamba Sanskrit Sansthan, Varanasi, Edn. $14^{th}$ 2001. [This book contains references from 1000 B.C to $18^{th}$ century] p. 766. Formulation ID: AK/4041B. Formulation Name: Catvarirasayanam (2).
Meyer et al., Striatal dysregulation of Cdk5 alters locomotor responses to cocaine, motor learning, and dendritic morphology. Proc Natl Acad Sci U S A. Nov. 25, 2008;105(47):18561-6. doi: 10.1073/pnas.0806078105. Epub Nov. 18, 2008.
Nicolosi, Chemo-enzymatic preparation of resveratrol derivatives. J Mol Catalysis B: Enzymatic 16. 2002:223-229.
Park et al., Resveratrol ameliorates aging-related metabolic phenotypes by inhibiting cAMP phosphodiesterases. Cell. Feb. 3, 2012;148(3):421-33. doi:10.1016/j.cell.2012.01.017.
Rasayoga Sagara- Compiled and Translated by Vaidya Pandita Hariprapanna Ji, vol. 1: Krishnada Academy, Varanasi, Edn. Reprint, 1999. [This book contains back references from 1000 B.C. to 20th century] p. 365. Formulation ID: SJ/875. Formulation Name: Gandhakarasayanam—3.
Rasayoga Sagara- Compiled and Translated by Vaidya Pandita Hariprapanna Ji, vol. 1: Krishnadas Academy, Varanasi, Edn. Reprint, 1999. [This book contains back references from 1000 B.C to $20^{th}$ centry] p. 591. Formulation ID: SJ/1498. Formulation Name: Trsnarirasah.
Siddhayogasamgrahah- Compiled by Yadavji Trikamji Acharya, Sri Baidyanath Ayurved Bhawan, Allahabad, Edn. $1^{st}$ 1978 p. 157. Formulation ID: RG10/244A. Formulation Name: Abhraka Maranaam.
Sodhala; Sodhalanighantauh- (Namasamgraha Va Gunasamgraha) Edited by P.V. Sharma, Oriental Institute, Baroda, Edn $1^{st}$ 1978 p. 127. Formulation ID: RG9/299. Formulation Name: Rasona Guna.
Sundaram et al., Cdk5/p25-induced cytosolic PLA2-mediated lysophosphatidylcholine production regulates neuroinflammation and triggers neurodegeneration. J Neurosci. Jan. 18, 2012;32(3):1020-34.
Tennen et al., Finding a target for resveratrol. Cell. Feb. 3, 2012;148(3):387-9. doi: 10.1016/j.cell.2012.01.032.
Third Party Observations mailed Nov. 29, 2010 for Application No. 10167645.0.
Yogaratnakarah- Commentary by Laksmipatisastri, Edited by Brahmasankara Sastri, Chaukhamba Sanskrit Sansthan (Varanasi) Ed. $7^{th}$ 2002 p. 34. Formulation ID: RG3/73A. Formulation Name: Lasuna Guna.
Yogaratnakarah- Commentary by Laksmipatisastri. Edited by Brahmasankara Sastri. Chaukhamba Sanskrit Sansthan (Varanasi) Ed. $7^{th}$ 2002. p. 115. Formulation ID: RG3/285. Formulation Name: Samtarpana Guna.
Hendriks et al., Flavonoids inhibit myelin phagocytosis by macrophages; a structure-activity relationship study. Biochem Pharmacol. Mar. 1, 2003;65(5):877-85.
TANG, Resveratrol is neuroprotective because it is not a direct activator of Sirt1-A hypothesis. Brain Res Bull. Mar. 16, 2010;81(4-5):359-61. doi: 10.1016/j.brainresbull.2009.12.007. Epub Dec. 21, 2009.

\* cited by examiner

COGNITIVE PERFORMANCE WITH SIRTUIN ACTIVATORS

GOVERNMENT SUPPORT

This invention was made with government support under Grant number GM053049 awarded by the National Institutes of Health. The government has certain rights in this invention.

CROSS-REFERENCE TO RELATED APPLICATIONS

This application is a Continuation-in-part of International Application No. PCT/US2006/023239, filed Jun. 14, 2006, which claims the benefit of U.S. Provisional Application No. 60/690,306, filed Jun. 14, 2005, and U.S. Provisional Application No. 60/702,236, filed Jul. 25, 2005, the content of each of which is specifically incorporated by reference herein in its entirety.

BACKGROUND

Learning is a process by which organisms alter and adapt their behavior in response to environmental stimuli. As such learning and memory are mechanisms that are ultimately important for the organism's survival and its biological fitness. In a number of pathological situations, including Alzheimer's disease, Lewy body diseases, mood and anxiety disorders but also during normal aging, cognitive processes such as learning and memory are impaired. It is therefore desirable to identify components that would enhance cognitive function.

SUMMARY

Provided herein are methods for enhancing or preventing the decline of cognitive performance in a subject, comprising administering to a subject in need thereof a therapeutically effective amount of an agent that increases the level or activity of a sirtuin. A subject may be a healthy subject, e.g., a subject who desires increasing its cognitive performance. For example, the subject may be preparing for an intellectual challenge. A subject may also be a subject that is or will be sleep deprived, fatigued, drowsy or sleepy. A subject may be a subject who has or will have a substance-induced cognitive decline. A substance-induced cognitive decline may be an alcohol- or drug abuse-induced cognitive decline or a medicament-induced cognitive decline. A subject may be a subject having an injury-related decline in cognitive performance. A subject may have an aging related decline in a cognitive function and may be, e.g., at least about 50 years old. A subject may have been diagnosed as having impaired cognitive performance relative to the subject's usual cognitive performance.

The methods described herein may also be used for treating a subject having a learning disability; a mood disorder, an anxiety disorder, depression, schizophrenia, autism, anxiety, panic attacks, binge eating, social phobia, an affective disorder, attention deficit hyperactivity disorder, or a psychiatric disorder. A subject that may be treated may have a disease that impairs cognitive performance, e.g., a neurodegenerative disease or a central nervous system condition, such as a disease selected from the group consisting of Lewy body diseases, Alzheimer's disease, amniotropic lateral sclerosis (ALS), Parkinson's Disease, Huntington's Chorea, senile dementia, Pick's disease, parkinsonism dementia syndrome, progressive subcortical gliosis, progressive supranuclear palsy, thalamic degeneration syndrome, hereditary aphasia, and myoclonus epilepsy.

Other diseases that may be treated include a condition or disease selected from the group consisting of frontal-temporal dementia, mood and anxiety disorders, depression, Schizophrenia, autism, anxiety, panic attacks, binge eating, social phobia, an affective disorder, a psychiatric disorder, mild cognitive impairment, seizures, neurodegenerative illnesses, dementia, head trauma or injury, hysteria accompanied by confusion, cognitive disorders; age-related dementias; age-induced memory impairment; ion deficit disorder; psychosis; cognitive deficits associated with psychosis; and drug-induced psychosis.

A method may comprise administering to a subject in need thereof an agent that increases the level or activity of human SIRT1. The agent may be a sirtuin activator, e.g., a compound having a formula selected from formulas 1-25, 30, and 32-73. A sirtuin activator may be administered orally. A method may comprise further administering to the subject another agent, such as an anti-oxidant. A subject may be a mammal, such as a human. An agent may also be a sirtuin protein or a biologically active portion thereof or nucleic acid encoding such.

Also provided herein are compositions, such as therapeutic compositions, e.g., comprising a sirtuin activator and another agent that enhances a cognitive function. In certain embodiments, the sirtuin activator and the other agent do not naturally occur together in the same composition.

A method for improving cognitive performance in a subject may also comprise one or more of the following steps in any order or in the following order: (i) determining the cognitive performance of a subject; (ii) comparing the cognitive performance of the subject to a control value; and (iii) administering to the subject a sirtuin-activating agent if the cognitive performance of the subject is lower than the control value. The control value may be a value that corresponds to the usual cognitive performance of the subject. The control value may be a value of the average cognitive performance of a group of control subjects of similar age to that of the subject. A method may further comprise determining the cognitive performance of the subject after administration of an agent that increases the level or activity of a sirtuin. A method may further comprise determining the level or activity of a sirtuin in a cell of the subject prior to and/or after administration of the agent that increases the level or activity of a sirtuin.

Also provided herein are methods for identifying an agent that enhances a cognitive function in a subject. A method may comprise (i) identifying an agent that increases the level or activity of a sirtuin and (ii) testing the agent identified in (i) in an animal model of cognitive function.

DETAILED DESCRIPTION

Figure 1:
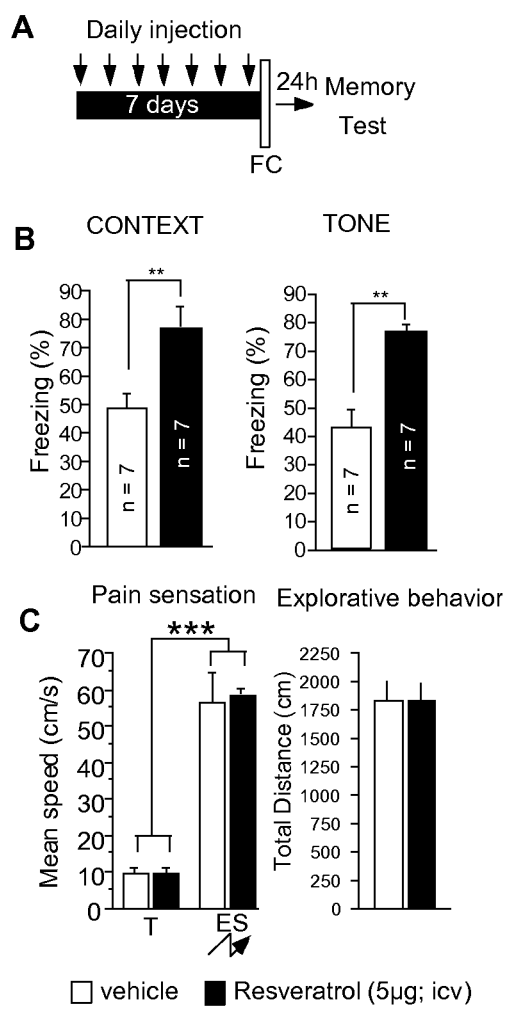
FIG. 1: Resveratrol facilitates associative learning. A. Experimental design. B. Freezing behavior of mice that were injected icv. with resveratrol or vehicle during the context- and tone dependent memory test. C. Mean activity of both groups during the training procedure (T) and the increased activity during the application of the electric foot shock (ES) indicating that pain sensation is not affected by resveratrol injection as the activity in both groups was indistinguishable. C. Total distance traveled during the training procedure reflecting the explorative behavior in response to a novel context. P<0.01 vs. vehicle; *P<0.0001 vs. vehicle.

Exemplary Compounds that Increase the Activity of a Sirtuin Protein

Compounds that increase the activity of sirtuins, e.g., SIRT1, are referred to as sirtuin "activation compounds" or "activating compounds." Exemplary compounds are described, e.g., in WO 05/002672 and WO 05/002555, and include polyphenols, e.g. plant polyphenols.

"Sirtuin deacetylase protein family members;" "Sir2 family members;" "Sir2 protein family members;" or "sirtuin proteins" includes yeast Sir2, Sir-2.1, and human SIRT1 and SIRT2 proteins. The nucleotide and amino acid sequences of the human sirtuin, SIRT1 (silent mating type information regulation 2 homolog); corresponding to GenBank Accession numbers NM_012238 and NP_036370, respectively. The mouse homolog of SIRT1 is Sirt2α. Human Sirt2 corresponds to GenBank Accession numbers NM_012237 and NP_036369 (for variant 1) and NM_030593 and NP_085096 (for variant 2). Other family members include the four additional yeast Sir2-like genes termed "HST genes" (homologues of Sir two) HST1, HST2, HST3 and HST4, and the five other human homologues hSIRT3 variant a (corresponding to GenBank Accession numbers NM_012239 and NP_036371), hSIRT3 variant b (corresponding to GenBank Accession numbers NM_001017524 and NP_001017524), hSIRT4 (corresponding to GenBank Accession numbers NM_012240 and NP_036372), hSIRT5 (corresponding to GenBank Accession numbers NM_012241 and NP_036373 for variant 1 and NM_031244 and NP_112534 for variant 2), hSIRT6 (corresponding to GenBank Accession numbers NM_016539 and NP_057623) and hSIRT7 (corresponding to GenBank Accession numbers NM_016538 and NP_057622) (Brachmann et al. (1995) Genes Dev. 9:2888 and Frye et al. (1999) BBRC 260:273). Preferred sirtuins are those that share more similarities with SIRT1, i.e., hSIRT1, and/or Sir2 than with SIRT2, such as those members having at least part of the N-terminal sequence present in SIRT1 and absent in SIRT2 such as SIRT3 has.

Nucleotide and amino acid sequences of human sirtuins and exemplary conserved domains are set forth below:

| Sirt domains | | nucleotide sequence | amino acid sequence | conserved (amino acids) |
|---|---|---|---|---|
| SIRT1 | | NM_012238 | NP_036370 | 431-536; 254-489 |
| SIRT2 | i1 | NM_012237 | NP_036369 | 77-331 |
| | i2 | NM_030593 | NP_085096 | 40-294 |
| SIRT3 | ia | NM_012239 | NP_036371 | 138-373 |
| | ib | NM_001017524 | NP_001017524 | 1-231 |
| SIRT4 | | NM_012240 | NP_036372 | 47-308 |
| SIRT5 | i1 | NM_012241 | NP_036373 | 51-301 |
| | i2 | NM_031244 | NP_112534 | 51-287 |
| SIRT6 | | NM_016539 | NP_057623 | 45-257 |
| SIRT7 | | NM_016538 | NP_057622 | 100-314 |

"Activating a sirtuin protein" refers to the action of producing an activated sirtuin protein, i.e., a sirtuin protein that is capable of performing at least one of its biological activities to at least some extent, e.g., with an increase of activity of at least about 10%, 50%, 2 fold or more. Biological activities of sirtuin proteins include deacetylation, e.g., of histones and p53; extending lifespan; increasing genomic stability; silencing transcription; and controlling the segregation of oxidized proteins between mother and daughter cells.

An "activating compound" of a sirtuin or a "sirtuin activating compound" refers to a compound that activates a sirtuin protein or stimulates or increases at least one of its activities. Activating compounds may have a formula selected from the group of formulas 1-25, 30 and 32-73. A "direct activator" of a sirtuin is a molecule that activates a sirtuin by binding to or interacting with it.

Exemplary activating compounds are those selected from the group consisting of flavones, stilbenes, flavanones, isoflavanones, catechins, chalcones, tannins and anthocyanidins. Exemplary stilbenes include hydroxystilbenes, such as trihydroxystilbenes, e.g., 3,5,4'-trihydroxystilbene ("resveratrol"). Resveratrol is also known as 3,4',5-stilbenetriol. Tetrahydroxystilbenes, e.g., piceatannol, are also encompassed. Hydroxychalones including trihydroxychalones, such as isoliquiritigenin, and tetrahydroxychalones, such as butein, can also be used. Hydroxyflavones including tetrahydroxyflavones, such as fisetin, and pentahydroxyflavones, such as quercetin, can also be used. At least some of these compounds may be obtained from Biomol, Sigma/Aldrich or Indofine.

In one embodiment, methods for activating a sirtuin protein comprise using an activating compound that is a stilbene or chalcone compound of formula 1:

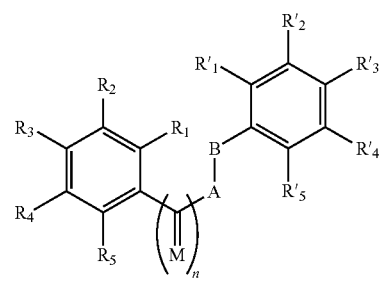

1 wherein, independently for each occurrence, $R_1$, $R_2$, $R_3$, $R_4$, $R_5$, $R'_1$, $R'_2$, $R'_3$, $R'_4$, and $R'_5$ represent H, alkyl, aryl, heteroaryl, aralkyl, alkaryl, heteroaralkyl, halide, $NO_2$, SR, OR, $N(R)_2$, or carboxyl;

R represents H, alkyl, aryl, heteroaryl, aralkyl, —SO₃H, monosaccharide, oligosaccharide, glycofuranosyl, glycopyranosyl, glucuronosyl, or glucuronide;

M represents O, NR, or S;

A-B represents a bivalent alkyl, alkenyl, alkynyl, amido, sulfonamido, diazo, ether, alkylamino, alkylsulfide, hydroxylamine, or hydrazine group; and n is 0 or 1.

In a further embodiment, the methods comprise a compound of formula 1 and the attendant definitions, wherein n is 0. In a further embodiment, the methods comprise a compound of formula 1 and the attendant definitions, wherein n is 1. In a further embodiment, the methods comprise a compound of formula 1 and the attendant definitions, wherein A-B is ethenyl. In a further embodiment, the methods comprise a compound of formula 1 and the attendant definitions, wherein A-B is —CH₂CH(Me)CH(Me)CH₂—. In a further embodiment, the methods comprise a compound of formula 1 and the attendant definitions, wherein M is O. In a further embodiment, the methods comprises a compound of formula 1 and the attendant definitions, wherein R₁, R₂, R₃, R₄, R₅, R'₁, R'₂, R'₃, R'₄, and R'₅ are H. In a further embodiment, the methods comprise a compound of formula 1 and the attendant definitions, wherein R₂, R₄, and R'₃ are OH. In a further embodiment, the methods comprise a compound of formula 1 and the attendant definitions, wherein R₂, R₄, R'₂ and R'₃ are OH. In a further embodiment, the methods comprise a compound of formula 1 and the attendant definitions, wherein R₃, R₅, R'₂ and R'₃ are OH. In a further embodiment, the methods comprise a compound of formula 1 and the attendant definitions, wherein R₁, R₃, R₅, R'₂ and R'₃ are OH. In a further embodiment, the methods comprise a compound of formula 1 and the attendant definitions, wherein R₂ and R'₂ are OH; R₄ is O—β-D-glucoside; and R'₃ is OCH₃. In a further embodiment, the methods comprise a compound of formula 1 and the attendant definitions, wherein R₂ is OH; R₄ is O-β-D-glucoside; and R'₃ is OCH₃.

In a further embodiment, the methods comprise a compound of formula 1 and the attendant definitions, wherein n is 0; A-B is ethenyl; and R₁, R₂, R₃, R₄, R₅, R'₁, R'₂, R'₃, R'₄, and R'₅ are H (trans stilbene). In a further embodiment, the methods comprise a compound of formula 1 and the attendant definitions, wherein n is 1; A-B is ethenyl; M is O; and R₁, R₂, R₃, R₄, R₅, R'₁, R'₂, R'₃, R'₄, and R'₅ are H (chalcone). In a further embodiment, the methods comprise a compound of formula 1 and the attendant definitions, wherein n is 0; A-B is ethenyl; R₂, R₄, and R'₃ are OH; and R₁, R₃, R₅, R'₁, R'₂, R'₄, and R'₅ are H (resveratrol). In a further embodiment, the methods comprise a compound of formula 1 and the attendant definitions, wherein n is 0; A-B is ethenyl; R₂, R₄, R'₂ and R'₃ are OH; and R₁, R₃, R₅, R'₁, R'₄ and R'₅ are H (piceatannol). In a further embodiment, the methods comprise a compound of formula 1 and the attendant definitions, wherein n is 1; A-B is ethenyl; M is O; R₃, R₅, R'₂ and R'₃ are OH; and R₁, R₂, R₄, R'₁, R'₄, and R'₅ are H (butein). In a further embodiment, the methods comprise a compound of formula 1 and the attendant definitions, wherein n is 1; A-B is ethenyl; M is O; R₁, R₃, R₅, R'₂ and R'₃ are OH; and R₂, R₄, R'₁, R'₄, and R'₅ are H (3,4,2',4',6'-pentahydroxychalcone). In a further embodiment, the methods comprise a compound of formula 1 and the attendant definitions, wherein n is 0; A-B is ethenyl; R₂ and R'₂ are OH, R₄ is O-β-D-glucoside, R'₃ is OCH₃; and R₁, R₃, R₅, R'₁, R'₄, and R'₅ are H (rhapontin). In a further embodiment, the methods comprise a compound of formula 1 and the attendant definitions, wherein n is 0; A-B is ethenyl; R₂ is OH, R₄ is O-β-D-glucoside, R'₃ is OCH₃; and R₁, R₃, R₅, R'₁, R'₂, R'₄, and R'₅ are H (deoxyrhapontin). In a further embodiment, the methods comprise a compound of formula 1 and the attendant definitions, wherein n is 0; A-B is —CH₂CH(Me)CH(Me)CH₂—; R₂, R₃, R'₂, and R'₃ are OH; and R₁, R₄, R₅, R'₁, R'₄, and R'₅ are H (NDGA).

In another embodiment, methods for activating a sirtuin protein comprise using an activating compound that is a flavanone compound of formula 2:

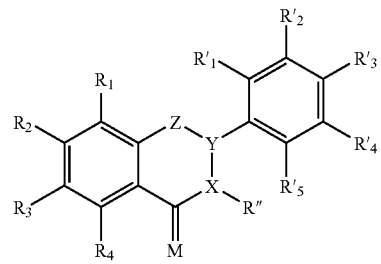

wherein, independently for each occurrence,

R₁, R₂, R₃, R₄, R'₁, R'₂, R'₃, R'₄, R'₅, and R" represent H, alkyl, aryl, heteroaryl, aralkyl, alkaryl, heteroaralkyl, halide, NO₂, SR, OR, N(R)₂, or carboxyl;

R represents H, alkyl, aryl, heteroaryl, aralkyl, —SO₃H, monosaccharide, oligosaccharide, glycofuranosyl, glycopyranosyl, glucuronosyl, or glucuronide;

M represents H₂, O, NR, or S;

Z represents CR, O, NR, or S;

X represents CR or N; and

Y represents CR or N.

In a further embodiment, the methods comprise a compound of formula 2 and the attendant definitions, wherein X and Y are both CH. In a further embodiment, the methods comprise a compound of formula 2 and the attendant definitions, wherein M is O. In a further embodiment, the methods comprise a compound of formula 2 and the attendant definitions, wherein M is H₂. In a further embodiment, the methods comprise a compound of formula 2 and the attendant definitions, wherein Z is O. In a further embodiment, the methods comprise a compound of formula 2 and the attendant definitions, wherein R" is H. In a further embodiment, the methods comprise a compound of formula 2 and the attendant definitions, wherein R" is OH. In a further embodiment, the methods comprise a compound of formula 2 and the attendant definitions, wherein R" is an alkoxycarbonyl. In a further embodiment, the methods comprise a compound of formula 2 and the attendant definitions, wherein R₁ is

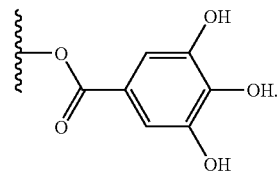 [SMILES: *OC(=O)c1cc(O)c(O)c(O)c1]

In a further embodiment, the methods comprise a compound of formula 2 and the attendant definitions, wherein R₁, R₂, R₃, R₄, R'₁, R'₂, R'₃, R'₄, R'₅ and R" are H. In a further embodiment, the methods comprise a compound of formula 2 and the attendant definitions, wherein R₂, R₄, and R'₃ are OH. In a further embodiment, the methods comprise a compound of formula 2 and the attendant definitions, wherein R₄, R'₂, R'₃, and R" are OH. In a further embodiment, the methods comprise a compound of formula 2 and the attendant definitions, wherein $R_2$, $R_4$, $R'_2$, $R'_3$, and R" are OH. In a further embodiment, the methods comprise a compound of formula 2 and the attendant definitions, wherein $R_2$, $R_4$, $R'_2$, $R'_3$, $R'_4$, and R" are OH.

In a further embodiment, the methods comprise a compound of formula 2 and the attendant definitions, wherein X and Y are CH; M is O; Z and O; R" is H; and $R_1$, $R_2$, $R_3$, $R_4$, $R'_1$, $R'_2$, $R'_3$, $R'_4$, $R'_5$ and R" are H (flavanone). In a further embodiment, the methods comprise a compound of formula 2 and the attendant definitions, wherein X and Y are CH; M is O; Z and O; R" is H; $R_2$, $R_4$, and $R'_3$ are OH; and $R_1$, $R_3$, $R'_1$, $R'_2$, $R'_4$, and $R'_5$ are H (naringenin). In a further embodiment, the methods comprise a compound of formula 2 and the attendant definitions, wherein X and Y are CH; M is O; Z and O; R" is OH; $R_2$, $R_4$, $R'_2$, and $R'_3$ are OH; and $R_1$, $R_3$, $R'_1$, $R'_4$, and $R'_5$ are H (3,5,7,3',4'-pentahydroxyflavanone). In a further embodiment, the methods comprise a compound of formula 2 and the attendant definitions, wherein X and Y are CH; M is $H_2$; Z and O; R" is OH; $R_2$, $R_4$, $R'_2$, and $R'_3$, are OH; and $R_1$, $R_3$, $R'_1$, $R'_4$ and $R'_5$ are H (epicatechin). In a further embodiment, the methods comprise a compound of formula 2 and the attendant definitions, wherein X and Y are CH; M is $H_2$; Z and O; R" is OH; $R_2$, $R_4$, $R'_2$, $R'_3$, and $R'_4$ are OH; and $R_1$, $R_3$, $R'_1$, and $R'_5$ are H (gallocatechin). In a further embodiment, the methods comprise a compound of formula 2 and the attendant definitions, wherein X and Y are CH; M is $H_2$; Z and O; R" is $R_2$, $R_4$, $R'_2$, $R'_3$, $R'_4$, and R" are OH; and $R_1$, $R_3$, $R'_1$, and $R'_5$ are H (epigallocatechin gallate).

In another embodiment, methods for activating a sirtuin protein comprise using an activating compound that is an isoflavanone compound of formula 3:

3 wherein, independently for each occurrence, $R_1$, $R_2$, $R_3$, $R_4$, $R'_1$, $R'_2$, $R'_3$, $R'_4$, $R'_5$, and $R'_1$ represent H, alkyl, aryl, heteroaryl, aralkyl, alkaryl, heteroaralkyl, halide, $NO_2$, SR, OR, $N(R)_2$, or carboxyl;

R represents H, alkyl, aryl, heteroaryl, aralkyl, —$SO_3H$, monosaccharide, oligosaccharide, glycofuranosyl, glycopyranosyl, glucuronosyl, or glucuronide;

M represents $H_2$, O, NR, or S;

Z represents $C(R)_2$, O, NR, or S;

X represents CR or N; and

Y represents CR or N.

In another embodiment, methods for activating a sirtuin protein comprise using an activating compound that is a flavone compound of formula 4:

4 wherein, independently for each occurrence, $R_1$, $R_2$, $R_3$, $R_4$, $R'_1$, $R'_2$, $R'_3$, $R'_4$, and $R'_5$, represent H, alkyl, aryl, heteroaryl, aralkyl, alkaryl, heteroaralkyl, halide, $NO_2$, SR, OR, $N(R)_2$, or carboxyl;

R represents H, alkyl, aryl, heteroaryl, aralkyl, —$SO_3H$, monosaccharide, oligosaccharide, glycofuranosyl, glycopyranosyl, glucuronosyl, or glucuronide;

M represents $H_2$, O, NR, or S;

Z represents CR, O, NR, or S; and

X represents CR" or N, wherein

R" is H, alkyl, aryl, heteroaryl, alkaryl, heteroaralkyl, halide, $NO_2$, SR, OR, $N(R)_2$, or carboxyl.

In a further embodiment, the methods comprise a compound of formula 4 and the attendant definitions, wherein X is C. In a further embodiment, the methods comprise a compound of formula 4 and the attendant definitions, wherein X is CR. In a further embodiment, the methods comprise a compound of formula 4 and the attendant definitions, wherein Z is O. In a further embodiment, the methods comprise a compound of formula 4 and the attendant definitions, wherein M is O. In a further embodiment, the methods comprise a compound of formula 4 and the attendant definitions, wherein R" is H. In a further embodiment, the methods comprise a compound of formula 4 and the attendant definitions, wherein R" is OH. In a further embodiment, the methods comprise a compound of formula 4 and the attendant definitions, wherein $R_1$, $R_2$, $R_3$, $R_4$, $R'_1$, $R'_2$, $R'_3$, $R'_4$, and $R'_5$ are H. In a further embodiment, the methods comprise a compound of formula 4 and the attendant definitions, wherein $R_2$, $R'_2$, and $R'_3$ are OH. In a further embodiment, the methods comprise a compound of formula 4 and the attendant definitions, wherein $R_2$, $R_4$, $R'_2$, $R'_3$, and $R'_4$ are OH. In a further embodiment, the methods comprise a compound of formula 4 and the attendant definitions, wherein $R_2$, $R_4$, $R'_2$, and $R'_3$ are OH. In a further embodiment, the methods comprise a compound of formula 4 and the attendant definitions, wherein $R_3$, $R'_2$, and $R'_3$ are OH. In a further embodiment, the methods comprise a compound of formula 4 and the attendant definitions, wherein $R_2$, $R_4$, $R'_2$, and $R'_3$ are OH. In a further embodiment, the methods comprise a compound of formula 4 and the attendant definitions, wherein $R_2$, $R'_2$, $R'_3$, and $R'_4$ are OH. In a further embodiment, the methods comprise a compound of formula 4 and the attendant definitions, wherein $R_2$, $R_4$, and $R'_3$ are OH. In a further embodiment, the methods comprise a compound of formula 4 and the attendant definitions, wherein $R_2$, $R_3$, $R_4$, and $R'_3$ are OH. In a further embodiment, the methods comprise a compound of formula 4 and the attendant definitions, wherein $R_2$, $R_4$, and $R'_3$ are OH. In a further embodiment, the methods comprise a compound of formula 4 and the attendant definitions, wherein $R_3$, $R'_1$, and $R'_3$ are OH. In a further embodiment, the methods comprise a compound of formula 4 and the attendant definitions, wherein $R_2$ and $R'_3$ are OH. In a further embodiment, the methods comprise a compound of formula 4 and the attendant definitions, wherein $R_1$, $R_2$, $R'_2$, and $R'_3$ are OH. In a further embodiment, the methods comprise a compound of formula 4 and the attendant definitions, wherein $R_3$, $R'_1$, and $R'_2$ are OH. In a further embodiment, the methods comprise a compound of formula 4 and the attendant definitions, wherein $R'_3$ is OH. In a further embodiment, the methods comprise a compound of formula 4 and the attendant definitions, wherein $R_4$ and $R'_3$ are OH. In a further embodiment, the methods comprise a compound of formula 4 and the attendant definitions, wherein $R_2$ and $R_4$ are OH. In a further embodiment, the methods comprise a compound of formula 4 and the attendant definitions, wherein $R_2$, $R_4$, $R'_1$, and $R'_3$ are OH. In a further embodiment, the methods comprise a compound of formula 4 and the attendant definitions, wherein $R_4$ is OH. In a further embodiment, the methods comprise a compound of formula 4 and the attendant definitions, wherein $R_2$, $R_4$, $R'_2$, $R'_3$, and $R'_4$ are OH. In a further embodiment, the methods comprise a compound of formula 4 and the attendant definitions, wherein $R_2$, $R'_2$, $R'_3$, and $R'_4$ are OH. In a further embodiment, the methods comprise a compound of formula 4 and the attendant definitions, wherein $R_1$, $R_2$, $R_4$, $R'_2$, and $R'_3$ are OH.

In a further embodiment, the methods comprise a compound of formula 4 and the attendant definitions, wherein X is CH; Z is O; M is O; and $R_1$, $R_2$, $R_3$, $R_4$, $R'_1$, $R'_2$, $R'_3$, $R'_4$, and $R'_5$ are H (flavone). In a further embodiment, the methods comprise a compound of formula 4 and the attendant definitions, wherein X is COH; Z is O; M is O; $R_2$, $R'_2$, and $R'_3$ are OH; and $R_1$, $R_3$, $R_4$, $R'_1$, $R'_4$, and $R'_5$ are H (fisetin). In a further embodiment, the methods comprise a compound of formula 4 and the attendant definitions, wherein X is CH; Z is O; M is O; $R_2$, $R_4$, $R'_2$, $R'_3$, and $R'_4$ are OH; and $R_1$, $R_3$, $R'_1$, and $R'_5$ are H (5,7,3',4',5'-pentahydroxyflavone). In a further embodiment, the methods comprise a compound of formula 4 and the attendant definitions, wherein X is CH; Z is O; M is O; $R_2$, $R_4$, $R'_2$, and $R'_3$ are OH; and $R_1$, $R_3$, $R'_1$, $R'_4$, and $R'_5$ are H (luteolin). In a further embodiment, the methods comprise a compound of formula 4 and the attendant definitions, wherein X is COH; Z is O; M is O; $R_3$, $R'_2$, and $R'_3$ are OH; and $R_1$, $R_2$, $R_4$, $R'_1$, $R'_4$, and $R'_5$ are H (3,6,3',4'-tetrahydroxyflavone). In a further embodiment, the methods comprise a compound of formula 4 and the attendant definitions, wherein X is COH; Z is O; M is O; $R_2$, $R_4$, $R'_2$, and $R'_3$ are OH; and $R_1$, $R_3$, $R'_1$, $R'_4$, and $R'_5$ are H (quercetin). In a further embodiment, the methods comprise a compound of formula 4 and the attendant definitions, wherein X is CH; Z is O; M is O; $R_2$, $R'_2$, $R'_3$, and $R'_4$ are OH; and $R_1$, $R_3$, $R_4$, $R'_1$, and $R'_5$ are H. In a further embodiment, the methods comprise a compound of formula 4 and the attendant definitions, wherein X is COH; Z is O; M is O; $R_2$, $R_4$, and $R'_3$ are OH; and $R_1$, $R_3$, $R'_1$, $R'_2$, $R'_4$, and $R'_5$ are H. In a further embodiment, the methods comprise a compound of formula 4 and the attendant definitions, wherein X is CH; Z is O; M is O; $R_2$, $R_3$, $R_4$, and $R'_3$ are OH; and $R_1$, $R'_1$, $R'_2$, $R'_4$, and $R'_5$ are H. In a further embodiment, the methods comprise a compound of formula 4 and the attendant definitions, wherein X is CH; Z is O; M is O; $R_2$, $R_4$, and $R'_3$ are OH; and $R_1$, $R_3$, $R'_1$, $R'_2$, $R'_4$, and $R'_5$ are H. In a further embodiment, the methods comprise a compound of formula 4 and the attendant definitions, wherein X is COH; Z is O; M is O; $R_3$, $R'_1$, and $R'_3$ are OH; and $R_1$, $R_2$, $R'_2$, $R'_4$, and $R'_5$ are H. In a further embodiment, the methods comprise a compound of formula 4 and the attendant definitions, wherein X is CH; Z is O; M is O; $R_2$ and $R'_3$ are OH; and $R_1$, $R_3$, $R_4$, $R'_1$, $R'_2$, $R'_4$, and $R'_5$ are H. In a further embodiment, the methods comprise a compound of formula 4 and the attendant definitions, wherein X is COH; Z is O; M is O; $R_1$, $R_2$, $R'_2$, and $R'_3$ are OH; and $R_1$, $R_2$, $R_4$, $R'_3$, $R'_4$, and $R'_5$ are H. In a further embodiment, the methods comprise a compound of formula 4 and the attendant definitions, wherein X is COH; Z is O; M is O; $R_3$, $R'_1$, and $R'_2$ are OH; and $R_1$, $R_2$, $R_4$; $R'_3$, $R'_4$, and $R'_5$ are H. In a further embodiment, the methods comprise a compound of formula 4 and the attendant definitions, wherein X is CH; Z is O; M is O; $R'_3$ is OH; and $R_1$, $R_2$, $R_3$, $R_4$, $R'_1$, $R'_2$, $R'_4$, and $R'_5$ are H. In a further embodiment, the methods comprise a compound of formula 4 and the attendant definitions, wherein X is CH; Z is O; M is O; $R_4$ and $R'_3$ are OH; and $R_1$, $R_2$, $R_3$, $R'_1$, $R'_2$, $R'_4$, and $R'_5$ are H. In a further embodiment, the methods comprise a compound of formula 4 and the attendant definitions, wherein X is CH; Z is O; M is O; $R_2$ and $R_4$ are OH; and $R_1$, $R_3$, $R'_1$, $R'_2$, $R'_3$, $R'_4$, and $R'_5$ are H. In a further embodiment, the methods comprise a compound of formula 4 and the attendant definitions, wherein X is COH; Z is O; M is O; $R_2$, $R_4$, $R'_1$, and $R'_3$ are OH; and $R_1$, $R_3$, $R'_2$, $R'_4$, and $R'_5$ are H. In a further embodiment, the methods comprise a compound of formula 4 and the attendant definitions, wherein X is CH; Z is O; M is O; $R_4$ is OH; and $R_1$, $R_2$, $R_3$, $R'_1$, $R'_2$, $R'_3$, $R'_4$, and $R'_5$ are H. In a further embodiment, the methods comprise a compound of formula 4 and the attendant definitions, wherein X is COH; Z is O; M is O; $R_2$, $R_4$, $R'_2$, $R'_3$, and $R'_4$ are OH; and $R_1$, $R_3$, $R'_1$, and $R'_5$ are H. In a further embodiment, the methods comprise a compound of formula 4 and the attendant definitions, wherein X is COH; Z is O; M is O; $R_2$, $R'_2$, $R'_3$, and $R'_4$ are OH; and $R_1$, $R_3$, $R_4$, $R'_1$, and $R'_5$ are H. In a further embodiment, the methods comprise a compound of formula 4 and the attendant definitions, wherein X is COH; Z is O; M is O; $R_1$, $R_2$, $R_4$, $R'_2$, and $R'_3$ are OH; and $R_3$, $R'_1$, $R'_4$, and $R'_5$ are H.

In another embodiment, methods for activating a sirtuin protein comprise using an activating compound that is an isoflavone compound of formula 5:

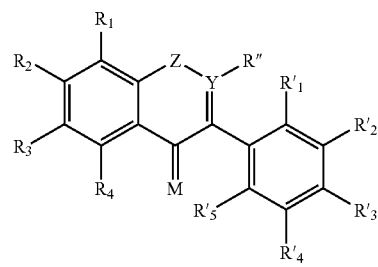

5 wherein, independently for each occurrence, $R_1$, $R_2$, $R_3$, $R_4$, $R'_1$, $R'_2$, $R'_3$, $R'_4$, and $R'_5$, represent H, alkyl, aryl, heteroaryl, aralkyl, alkaryl, heteroaralkyl, halide, $NO_2$, SR, OR, $N(R)_2$, or carboxyl;

R represents H, alkyl, aryl, heteroaryl, aralkyl, —$SO_3H$, monosaccharide, oligosaccharide, glycofuranosyl, glycopyranosyl, glucuronosyl, or glucuronide;

M represents $H_2$, O, NR, or S;

Z represents $C(R)_2$, O, NR, or S; and

Y represents CR" or N, wherein

R" represents H, alkyl, aryl, heteroaryl, alkaryl, heteroaralkyl, halide, $NO_2$, SR, OR, $N(R)_2$, or carboxyl.

In a further embodiment, the methods comprise a compound of formula 5 and the attendant definitions, wherein Y is CR". In a further embodiment, the methods comprise a compound of formula 5 and the attendant definitions, wherein Y is CH. In a further embodiment, the methods comprise a compound of formula 5 and the attendant definitions, wherein Z is O. In a further embodiment, the methods comprise a compound of formula 5 and the attendant definitions, wherein M is O. In a further embodiment, the methods comprise a compound of formula 5 and the attendant definitions, wherein $R_2$ and $R'_3$ are OH. In a further embodiment, the methods comprise a compound of formula 5 and the attendant definitions, wherein $R_2$, $R_4$, and $R'_3$ are OH.

In a further embodiment, the methods comprise a compound of formula 5 and the attendant definitions, wherein Y is CH; Z is O; M is O; $R_2$ and $R'_3$ are OH; and $R_1$, $R_3$, $R_4$, $R'_1$, $R'_2$, $R'_4$, and $R'_5$ are H. In a further embodiment, the methods comprise a compound of formula 5 and the attendant definitions, wherein Y is CH; Z is O; M is O; $R_2$, $R_4$, and $R'_3$ are OH; and $R_1$, $R_3$, $R'_1$, $R'_2$, $R'_4$, and $R'_5$ are H.

In another embodiment, methods for activating a sirtuin protein comprise using an activating compound that is an anthocyanidin compound of formula 6:

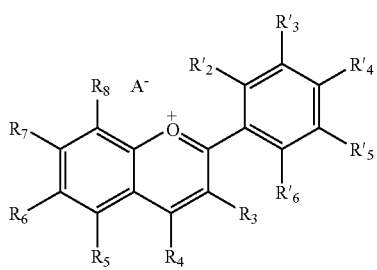

6 wherein, independently for each occurrence, $R_3$, $R_4$, $R_5$, $R_6$, $R_7$, $R_8$, $R'_2$, $R'_3$, $R'_4$, $R'_5$, and $R'_6$ represent H, alkyl, aryl, heteroaryl, aralkyl, alkaryl, heteroaralkyl, halide, $NO_2$, SR, OR, $N(R)_2$, or carboxyl;

R represents H, alkyl, aryl, heteroaryl, aralkyl, —$SO_3H$, monosaccharide, oligosaccharide, glycofuranosyl, glycopyranosyl, glucuronosyl, or glucuronide; and $A^-$ represents an anion selected from the following: $Cl^-$, $Br^-$, or $I^-$.

In a further embodiment, the methods comprise a compound of formula 6 and the attendant definitions, wherein $A^-$ is $Cl^-$. In a further embodiment, the methods comprise a compound of formula 6 and the attendant definitions, wherein $R_3$, $R_5$, $R_7$, and $R'_4$ are OH. In a further embodiment, the methods comprise a compound of formula 6 and the attendant definitions, wherein $R_3$, $R_5$, $R_7$, $R'_3$, and $R'_4$ are OH. In a further embodiment, the methods comprise a compound of formula 6 and the attendant definitions, wherein $R_3$, $R_5$, $R_7$, $R'_3$, $R'_4$, and $R'_5$ are OH.

In a further embodiment, the methods comprise a compound of formula 6 and the attendant definitions, wherein $A^-$ is $Cl^-$; $R_3$, $R_5$, $R_7$, and $R'_4$ are OH; and $R_4$, $R_6$, $R_8$, $R'_2$, $R'_3$, $R'_5$, and $R'_6$ are H. In a further embodiment, the methods comprise a compound of formula 6 and the attendant definitions, wherein $A^-$ is $Cl^-$; $R_3$, $R_5$, $R_7$, $R'_3$, and $R'_4$ are OH; and $R_4$, $R_6$, $R_8$, $R'_2$, $R'_5$, and $R'_6$ are H. In a further embodiment, the methods comprise a compound of formula 6 and the attendant definitions, wherein $A^-$ is $Cl^-$; $R_3$, $R_5$, $R_7$, $R'_3$, $R'_4$, and $R'_5$ are OH; and $R_4$, $R_6$, $R_8$, $R'_2$, and $R'_6$ are H.

Methods for activating a sirtuin protein may also comprise using a stilbene, chalcone, or flavone compound represented by formula 7:

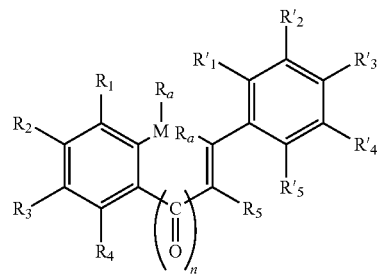

7 wherein, independently for each occurrence:

M is absent or O;

$R_1$, $R_2$, $R_3$, $R_4$, $R_5$, $R'_1$, $R'_2$, $R'_3$, $R'_4$, and $R'_5$ represent H, alkyl, aryl, heteroaryl, aralkyl, alkaryl, heteroaralkyl, halide, $NO_2$, SR, OR, $N(R)_2$, or carboxyl;

$R_a$ represents H or the two instances of $R_a$ form a bond;

R represents H, alkyl, aryl, heteroaryl, aralkyl, —$SO_3H$, monosaccharide, oligosaccharide, glycofuranosyl, glycopyranosyl, glucuronosyl, or glucuronide; and n is 0 or 1.

In a further embodiment, the methods comprise an activating compound represented by formula 7 and the attendant definitions, wherein n is 0. In a further embodiment, the methods comprise an activating compound represented by formula 7 and the attendant definitions, wherein n is 1. In a further embodiment, the methods comprise an activating compound represented by formula 7 and the attendant definitions, wherein M is absent. In a further embodiment, the methods comprise an activating compound represented by formula 7 and the attendant definitions, wherein M is O. In a further embodiment, the methods comprise an activating compound represented by formula 7 and the attendant definitions, wherein $R_a$ is H. In a further embodiment, the methods comprise an activating compound represented by formula 7 and the attendant definitions, wherein M is O and the two $R_a$ form a bond.

In a further embodiment, the methods comprise an activating compound represented by formula 7 and the attendant definitions, wherein $R_5$ is H. In a further embodiment, the methods comprise an activating compound represented by formula 7 and the attendant definitions, wherein $R_5$ is OH. In a further embodiment, the methods comprise an activating compound represented by formula 7 and the attendant definitions, wherein $R_1$, $R_3$, and $R'_3$ are OH. In a further embodiment, the methods comprise an activating compound represented by formula 7 and the attendant definitions, wherein $R_2$, $R_4$, $R'_2$, and $R'_3$ are OH. In a further embodiment, the methods comprise an activating compound represented by formula 7 and the attendant definitions, wherein $R_2$, $R'_2$, and $R'_3$ are OH. In a further embodiment, the methods comprise an activating compound represented by formula 7 and the attendant definitions, wherein $R_2$ and $R_4$ are OH.

In a further embodiment, the methods include contacting a cell with an activating compound represented by formula 7 and the attendant definitions, wherein n is O; M is absent; $R_a$ is H; $R_5$ is H; $R_1$, $R_3$, and $R'_3$ are OH; and $R_2$, $R_4$, $R'_1$, $R'_2$, $R'_4$, and $R'_5$ are H. In a further embodiment, the methods comprise an activating compound represented by formula 7 and the attendant definitions, wherein n is 1; M is absent; $R_a$ is H; $R_5$ is H; $R_2$, $R_4$, $R'_2$, and $R'_3$ are OH; and $R_1$, $R_3$, $R'_1$, $R'_4$, and $R'_5$ are H. In a further embodiment, the methods comprise an activating compound represented by formula 7 and the attendant definitions, wherein n is 1; M is O; the two $R_a$ form a bond; $R_5$ is OH; $R_2$, $R'_2$, and $R'_3$ are OH; and $R_1$, $R_3$, $R_4$, $R'_1$, $R'_4$, and $R'_5$ are H.

Other compounds for activating sirtuin deacetylase protein family members include compounds having a formula selected from the group consisting of formulas 8-25 and 30 set forth below:

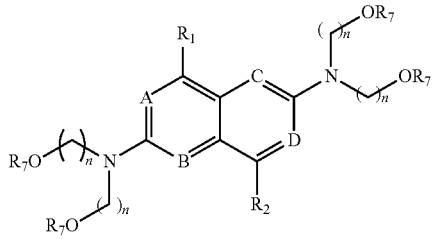
8 wherein, independently for each occurrence:
$R_1$ and $R_2$ represent H, aryl, heterocycle, or small alkyl;
$R_7$ represents H, alkyl, aryl, heteroaryl, aralkyl, —SO$_3$H, monosaccharide, oligosaccharide, glycofuranosyl, glycopyranosyl, glucuronosyl, or glucuronide;
A, B, C, and D represent $CR_1$ or N; and
n is 0, 1, 2, or 3;

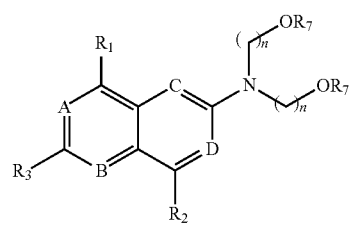
9 wherein, independently for each occurrence:
$R_1$ and $R_2$ represent H, aryl, heterocycle, or small alkyl;
$R_3$ represents small alkyl;
$R_7$ represents H, alkyl, aryl, heteroaryl, aralkyl, —SO$_3$H, monosaccharide, oligosaccharide, glycofuranosyl, glycopyranosyl, glucuronosyl, or glucuronide;
A, B, C, and D represent $CR_1$ or N; and
n is 0, 1, 2, or 3;

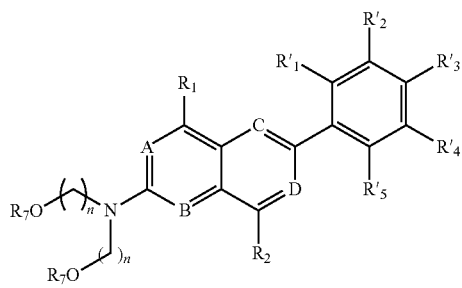
10 wherein, independently for each occurrence,
$R_1$ and $R_2$ represent H, aryl, heterocycle, or small alkyl;
$R'_1$, $R'_2$, $R'_3$, $R'_4$, and $R'_5$ represent H or $OR_7$;
$R_7$ represents H, alkyl, aryl, heteroaryl, aralkyl, —SO$_3$H, monosaccharide, oligosaccharide, glycofuranosyl, glycopyranosyl, glucuronosyl, or glucuronide;
A, B, C, and D represent $CR_1$ or N; and
n is 0, 1, 2, or 3;

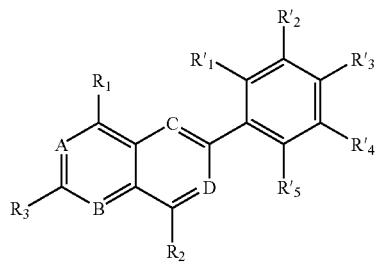
11 wherein, independently for each occurrence:
$R_1$ and $R_2$ represent H, aryl, heterocycle, or small alkyl;
$R_3$ represents small alkyl;
$R'_1$, $R'_2$, $R'_3$, $R'_4$, and $R'_5$ represent H or $OR_7$;
$R_7$ represents H, alkyl, aryl, heteroaryl, aralkyl, —SO$_3$H, monosaccharide, oligosaccharide, glycofuranosyl, glycopyranosyl, glucuronosyl, or glucuronide;
A, B, C, and D represent $CR_1$ or N; and
n is 0, 1, 2, or 3;

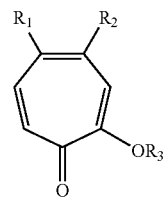
12 wherein, independently for each occurrence:
$R_1$ and $R_2$ represent H, aryl, or alkenyl; and
$R_7$ represents H, —SO$_3$H, monosaccharide, oligosaccharide, glycofuranosyl, glycopyranosyl, glucuronosyl, or glucuronide;

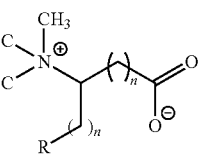
13 wherein, independently for each occurrence:
R represents heterocycle or aryl; and
n is 0 to 10 inclusive;

14

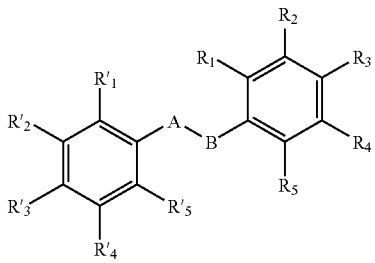

wherein, independently for each occurrence:

$R_1$, $R_2$, $R_3$, $R_4$, $R_5$, $R'_1$, $R'_2$, $R'_3$, $R'_4$, and $R'_5$ represents H, halogen, $NO_2$, SH, SR, OH, OR, NRR', alkyl, aryl or carboxy;

R represents H, alkyl, aryl, heteroaryl, aralkyl, —$SO_3H$, monosaccharide, oligosaccharide, glycofuranosyl, glycopyranosyl, glucuronosyl, or glucuronide;

R' represents H, alkyl, aryl, heteroaryl, aralkyl, —$SO_3H$, monosaccharide, oligosaccharide, glycofuranosyl, glycopyranosyl, glucuronosyl, or glucuronide; and A-B represents ethene, ethyne, amide, sulfonamide, diazo, alkyl, ether, alkyl amine, alkyl sulfide, hydroxyamine, or hydrazine;

15

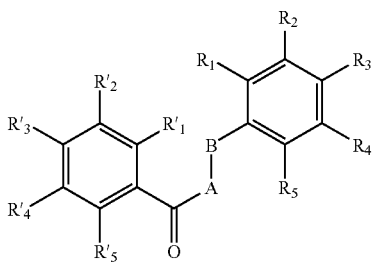

wherein, independently for each occurrence:

$R_1$, $R_2$, $R_3$, $R_4$, $R_5$, $R'_1$, $R'_2$, $R'_3$, $R'_4$, and $R'_5$ represents H, halogen, $NO_2$, SH, SR, OH, OR, NRR', alkyl, aryl or carboxy;

R represents H, alkyl, aryl, heteroaryl, aralkyl, —$SO_3H$, monosaccharide, oligosaccharide, glycofuranosyl, glycopyranosyl, glucuronosyl, or glucuronide;

R' represents H, alkyl, aryl, heteroaryl, aralkyl, —$SO_3H$, monosaccharide, oligosaccharide, glycofuranosyl, glycopyranosyl, glucuronosyl, or glucuronide; and A-B represents ethene, ethyne, amide, sulfonamide, diazo, alkyl, ether, alkyl amine, alkyl sulfide, hydroxyamine, or hydrazine;

16

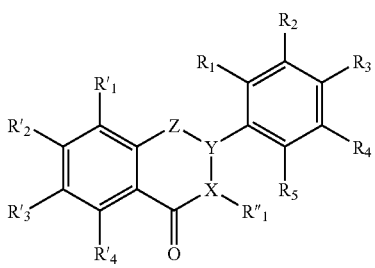

wherein, independently for each occurrence:

$R_1$, $R_2$, $R_3$, $R_4$, $R_5$, $R'_1$, $R'_2$, $R'_3$, $R'_4$, and $R'_5$ represents H, halogen, $NO_2$, SH, SR, OH, OR, NRR', alkyl, aryl or carboxy;

R represents H, alkyl, aryl, heteroaryl, aralkyl, —$SO_3H$, monosaccharide, oligosaccharide, glycofuranosyl, glycopyranosyl, glucuronosyl, or glucuronide;

R' represents H, alkyl, aryl, heteroaryl, aralkyl, —$SO_3H$, monosaccharide, oligosaccharide, glycofuranosyl, glycopyranosyl, glucuronosyl, or glucuronide;

X represents $CR_8$ or N;

Y represents $CR_8$ or N;

Z represents O, S, $C(R_8)_2$, or $NR_8$; and $R_8$ represents alkyl, aryl or aralkyl;

17

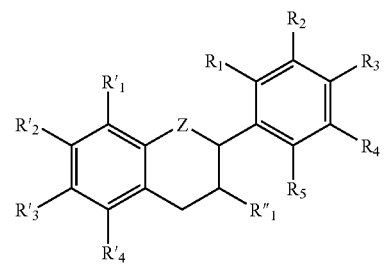

wherein, independently for each occurrence:

$R_1$, $R_2$, $R_3$, $R_4$, $R_5$, $R'_1$, $R'_2$, $R'_3$, $R'_4$, and $R'_5$ represents H, halogen, $NO_2$, SH, SR, OH, OR, NRR', alkyl, aryl or carboxy;

R represents H, alkyl, aryl, heteroaryl, aralkyl, —$SO_3H$, monosaccharide, oligosaccharide, glycofuranosyl, glycopyranosyl, glucuronosyl, or glucuronide;

R' represents H, alkyl, aryl, heteroaryl, aralkyl, —$SO_3H$, monosaccharide, oligosaccharide, glycofuranosyl, glycopyranosyl, glucuronosyl, or glucuronide;

X represents $CR_8$ or N;

Y represents $CR_8$ or N;

Z represents O, S, $C(R_8)_2$, or $NR_8$; and $R_8$ represents alkyl, aryl or aralkyl;

18

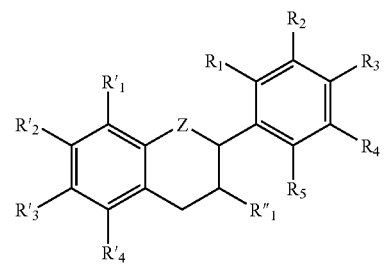

wherein, independently for each occurrence:

$R_1$, $R_2$, $R_3$, $R_4$, $R_5$, $R'_1$, $R'_2$, $R'_3$, $R'_4$, and $R'_5$ represents H, halogen, $NO_2$, SH, SR, OH, OR, NRR', alkyl, aryl or carboxy;

R represents H, alkyl, aryl, heteroaryl, aralkyl, —$SO_3H$, monosaccharide, oligosaccharide, glycofuranosyl, glycopyranosyl, glucuronosyl, or glucuronide;

R' represents H, alkyl, aryl, heteroaryl, aralkyl, —$SO_3H$, monosaccharide, oligosaccharide, glycofuranosyl, glycopyranosyl, glucuronosyl, or glucuronide;

Z represents O, S, C(R$_8$)$_2$, or NR$_8$; and
R$_8$ represents alkyl, aryl or aralkyl;

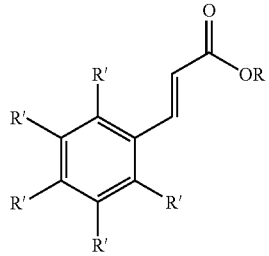

19 wherein, independently for each occurrence:
R is H, alkyl, aryl, heterocycyl, heteroaryl, aralkyl, —SO$_3$H, monosaccharide, oligosaccharide, glycofuranosyl, glycopyranosyl, glucuronosyl, or glucuronide; and
R' is H, halogen, NO$_2$, SR, OR, NR$_2$, alkyl, aryl, or carboxy;

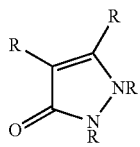

20 wherein, independently for each occurrence:
R is H, alkyl, aryl, heterocycyl, heteroaryl, aralkyl, —SO$_3$H, monosaccharide, oligosaccharide, glycofuranosyl, glycopyranosyl, glucuronosyl, or glucuronide;

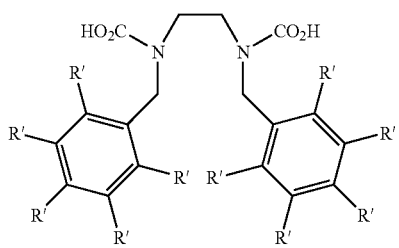

21 wherein, independently for each occurrence:
R' is H, halogen, NO$_2$, SR, OR, NR$_2$, alkyl, aryl, aralkyl, or carboxy; and
R is H, alkyl, aryl, heterocycyl, heteroaryl, aralkyl, —SO$_3$H, monosaccharide, oligosaccharide, glycofuranosyl, glycopyranosyl, glucuronosyl, or glucuronide;

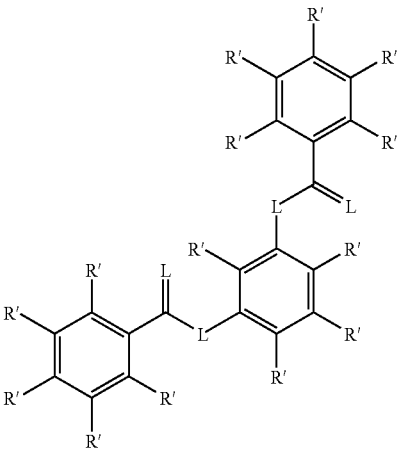

22 wherein, independently for each occurrence:
L represents CR$_2$, O, NR, or S;
R represents H, alkyl, aryl, aralkyl, heteroaralkyl, —SO$_3$H, monosaccharide, oligosaccharide, glycofuranosyl, glycopyranosyl, glucuronosyl, or glucuronide; and
R' represents H, halogen, NO$_2$, SR, OR, NR$_2$, alkyl, aryl, aralkyl, or carboxy;

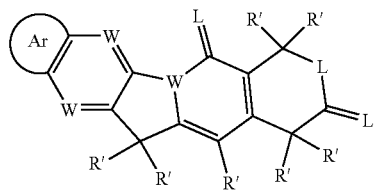

23 wherein, independently for each occurrence:
L represents CR$_2$, O, NR, or S;
W represents CR or N;
R represents H, alkyl, aryl, aralkyl, heteroaralkyl, —SO$_3$H, monosaccharide, oligosaccharide, glycofuranosyl, glycopyranosyl, glucuronosyl, or glucuronide; and
Ar represents a fused aryl or heteroaryl ring; and
R' represents H, halogen, NO$_2$, SR, OR, NR$_2$, alkyl, aryl, aralkyl, or carboxy;

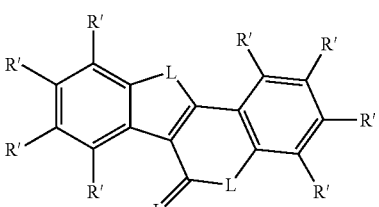

24 wherein, independently for each occurrence:
L represents CR$_2$, O, NR, or S;
R represents H, alkyl, aryl, aralkyl, heteroaralkyl, —SO$_3$H, monosaccharide, oligosaccharide, glycofuranosyl, glycopyranosyl, glucuronosyl, or glucuronide; and
R' represents H, halogen, NO$_2$, SR, OR, NR$_2$, alkyl, aryl, aralkyl, or carboxy;

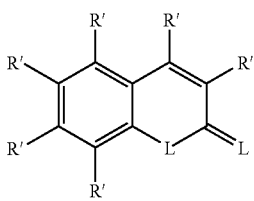

wherein, independently for each occurrence:

L represents $CR_2$, O, NR, or S;

R represents H, alkyl, aryl, aralkyl, heteroaralkyl, —$SO_3H$, monosaccharide, oligosaccharide, glycofuranosyl, glycopyranosyl, glucuronosyl, or glucuronide; and R' represents H, halogen, $NO_2$, SR, OR, $NR_2$, alkyl, aryl, aralkyl, or carboxy.

Methods for activating a sirtuin protein may also comprise using a stilbene, chalcone, or flavone compound represented by formula 30:

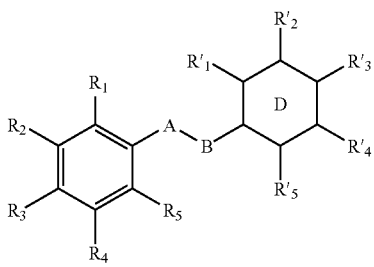

wherein, independently for each occurrence:

D is a phenyl or cyclohexyl group;

$R_1$, $R_2$, $R_3$, $R_4$, $R_5$, $R'_1$, $R'_2$, $R'_3$, $R'_4$, and $R'_5$ represent H, alkyl, aryl, heteroaryl, alkaryl, heteroaralkyl, halide, $NO_2$, SR, OR, $N(R)_2$, carboxyl, azide, ether; or any two adjacent $R_1$, $R_2$, $R_3$, $R_4$, $R_5$, $R'_1$, $R'_2$, $R'_3$, $R'_4$, or $R'_5$ groups taken together form a fused benzene or cyclohexyl group;

R represents H, alkyl, aryl, aralkyl, —$SO_3H$, monosaccharide, oligosaccharide, glycofuranosyl, glycopyranosyl, glucuronosyl, or glucuronide; and A-B represents an ethylene, ethenylene, or imine group;

provided that when A-B is ethenylene, D is phenyl, and $R'_3$ is H: $R_3$ is not OH when $R_1$, $R_2$, $R_4$, and $R_5$ are H; and $R_2$ and $R_4$ are not OMe when $R_1$, $R_3$, and $R_5$ are H; and $R_3$ is not OMe when $R_1$, $R_2$, $R_4$, and $R_5$ are H.

In a further embodiment, the methods include contacting a cell with an activating compound represented by formula 30 and the attendant definitions, wherein D is a phenyl group.

In a further embodiment, the methods include contacting a cell with an activating compound represented by formula 30 and the attendant definitions, wherein A-B is an ethenylene or imine group.

In a further embodiment, the methods include contacting a cell with an activating compound represented by formula 30 and the attendant definitions, wherein A-B is an ethenylene group.

In a further embodiment, the methods include contacting a cell with an activating compound represented by formula 30 and the attendant definitions, wherein $R_2$ is OH.

In a further embodiment, the methods include contacting a cell with an activating compound represented by formula 30 and the attendant definitions, wherein $R_4$ is OH In a further embodiment, the methods include contacting a cell with an activating compound represented by formula 30 and the attendant definitions, wherein $R_2$ and $R_4$ are OH.

In a further embodiment, the methods include contacting a cell with an activating compound represented by formula 30 and the attendant definitions, wherein D is a phenyl group; and A-B is an ethenylene group.

In a further embodiment, the methods include contacting a cell with an activating compound represented by formula 30 and the attendant definitions, wherein D is a phenyl group; A-B is an ethenylene group; and $R_2$ and $R_4$ are OH.

In a further embodiment, the methods include contacting a cell with an activating compound represented by formula 30 and the attendant definitions, wherein A-B is ethenylene; D is a phenyl ring; $R_2$ and $R_4$ are OH; and $R'_3$ is Cl.

In a further embodiment, the methods include contacting a cell with an activating compound represented by formula 30 and the attendant definitions, wherein A-B is ethenylene; D is a phenyl ring; $R_2$ and $R_4$ are OH; and $R'_3$ is OH.

In a further embodiment, the methods include contacting a cell with an activating compound represented by formula 30 and the attendant definitions, wherein A-B is ethenylene; D is a phenyl ring; $R_2$ and $R_4$ are OH; and $R'_3$ is H.

In a further embodiment, the methods include contacting a cell with an activating compound represented by formula 30 and the attendant definitions, wherein A-B is ethenylene; D is a phenyl ring; $R_2$ and $R_4$ are OH; and $R'_3$ is $CH_2CH_3$.

In a further embodiment, the methods include contacting a cell with an activating compound represented by formula 30 and the attendant definitions, wherein A-B is ethenylene; D is a phenyl ring; $R_2$ and $R_4$ are OH; and $R'_3$ is F.

In a further embodiment, the methods include contacting a cell with an activating compound represented by formula 30 and the attendant definitions, wherein A-B is ethenylene; D is a phenyl ring; $R_2$ and $R_4$ are OH; and $R'_3$ is Me.

In a further embodiment, the methods include contacting a cell with an activating compound represented by formula 30 and the attendant definitions, wherein A-B is ethenylene; D is a phenyl ring; $R_2$ and $R_4$ are OH; and $R'_3$ is an azide.

In a further embodiment, the methods include contacting a cell with an activating compound represented by formula 30 and the attendant definitions, wherein A-B is ethenylene; D is a phenyl ring; $R_2$ and $R_4$ are OH; and $R'_3$ is SMe.

In a further embodiment, the methods include contacting a cell with an activating compound represented by formula 30 and the attendant definitions, wherein A-B is ethenylene; D is a phenyl ring; $R_2$ and $R_4$ are OH; and $R'_3$ is $NO_2$.

In a further embodiment, the methods include contacting a cell with an activating compound represented by formula 30 and the attendant definitions, wherein A-B is ethenylene; D is a phenyl ring; $R_2$ and $R_4$ are OH; and $R'_3$ is $CH(CH_3)_2$.

In a further embodiment, the methods include contacting a cell with an activating compound represented by formula 30 and the attendant definitions, wherein A-B is ethenylene; D is a phenyl ring; $R_2$ and $R_4$ are OH; and $R'_3$ is OMe.

In a further embodiment, the methods include contacting a cell with an activating compound represented by formula 30 and the attendant definitions, wherein A-B is ethenylene; D is a phenyl ring; $R_2$ and $R_4$ are OH; $R'_2$ is OH; and $R'_3$ is OMe.

In a further embodiment, the methods include contacting a cell with an activating compound represented by formula 30 and the attendant definitions, wherein A-B is ethenylene; D is a phenyl ring; $R_2$ is OH; $R_4$ is carboxyl; and $R'_3$ is OH.

In a further embodiment, the methods include contacting a cell with an activating compound represented by formula 30 and the attendant definitions, wherein A-B is ethenylene; D is a phenyl ring; $R_2$ and $R_4$ are OH; and $R'_3$ is carboxyl.

In a further embodiment, the methods include contacting a cell with an activating compound represented by formula 30 and the attendant definitions, wherein A-B is ethenylene; D is a phenyl ring; $R_2$ and $R_4$ are OH; and $R'_3$ and $R'_4$ taken together form a fused benzene ring.

In a further embodiment, the methods include contacting a cell with an activating compound represented by formula 30 and the attendant definitions, wherein A-B is ethenylene; D is a phenyl ring; and $R_4$ is OH.

In a further embodiment, the methods include contacting a cell with an activating compound represented by formula 30 and the attendant definitions, wherein A-B is ethenylene; D is a phenyl ring; $R_2$ and $R_4$ are $OCH_2OCH_3$; and $R'_3$ is SMe.

In a further embodiment, the methods include contacting a cell with an activating compound represented by formula 30 and the attendant definitions, wherein A-B is ethenylene; D is a phenyl ring; $R_2$ and $R_4$ are OH; and $R'_3$ is carboxyl.

In a further embodiment, the methods include contacting a cell with an activating compound represented by formula 30 and the attendant definitions, wherein A-B is ethenylene; D is a cyclohexyl ring; and $R_2$ and $R_4$ are OH.

In a further embodiment, the methods include contacting a cell with an activating compound represented by formula 30 and the attendant definitions, wherein A-B is ethenylene; D is a phenyl ring; and $R_3$ and $R_4$ are OMe.

In a further embodiment, the methods include contacting a cell with an activating compound represented by formula 30 and the attendant definitions, wherein A-B is ethenylene; D is a phenyl ring; $R_2$ and $R_4$ are OH; and $R'_3$ is OH.

In another embodiment, methods for activating a sirtuin protein comprise using an activating compound of formula 32:

wherein, independently for each occurrence,

R is H, or a substituted or unsubstituted alkyl, aryl, aralkyl, heterocyclyl, heterocyclylalkyl, heteroaryl, or heteroaralkyl; and $R_1$ and $R_2$ are a substituted or unsubstituted alkyl, aryl, aralkyl, heterocyclyl, heterocyclylalkyl, heteroaryl, or heteroaralkyl.

In a further embodiment, the methods comprise a compound of formula 32 and the attendant definitions wherein R is H.

In a further embodiment, the methods comprise a compound of formula 32 and the attendant definitions wherein $R_1$ is 3-hydroxyphenyl.

In a further embodiment, the methods comprise a compound of formula 32 and the attendant definitions wherein $R_2$ is methyl.

In a further embodiment, the methods comprise a compound of formula 32 and the attendant definitions wherein R is H and $R_1$ is 3-hydroxyphenyl.

In a further embodiment, the methods comprise a compound of formula 32 and the attendant definitions wherein R is H, $R_1$ is 3-hydroxyphenyl, and $R_2$ is methyl.

In another embodiment, methods for activating a sirtuin protein comprise using an activating compound of formula 33:

wherein, independently for each occurrence:

R is H, or a substituted or unsubstituted alkyl, alkenyl, or alkynyl;

$R_1$ and $R_2$ are a substituted or unsubstituted alkyl, aryl, aralkyl, heterocyclyl, heterocyclylalkyl, heteroaryl, or heteroaralkyl; and L is O, S, or NR.

In a further embodiment, the methods comprise a compound of formula 33 and the attendant definitions wherein R is alkynyl.

In a further embodiment, the methods comprise a compound of formula 33 and the attendant definitions wherein $R_1$ is 2,6-dichlorophenyl.

In a further embodiment, the methods comprise a compound of formula 33 and the attendant definitions wherein $R_2$ is methyl.

In a further embodiment, the methods comprise a compound of formula 33 and the attendant definitions wherein L is O.

In a further embodiment, the methods comprise a compound of formula 33 and the attendant definitions wherein R is alkynyl and $R_1$ is 2,6-dichlorophenyl.

In a further embodiment, the methods comprise a compound of formula 33 and the attendant definitions wherein R is alkynyl, $R_1$ is 2,6-dichlorophenyl, and $R_2$ is methyl.

In a further embodiment, the methods comprise a compound of formula 33 and the attendant definitions wherein R is alkynyl, $R_1$ is 2,6-dichlorophenyl, $R_2$ is methyl, and L is O.

In another embodiment, methods for activating a sirtuin protein comprise using an activating compound of formula 34:

wherein, independently for each occurrence:

R, $R_1$, and $R_2$ are H, or a substituted or unsubstituted alkyl, aryl, aralkyl, heterocyclyl, heterocyclylalkyl, heteroaryl, or heteroaralkyl; and n is an integer from 0 to 5 inclusive.

In a further embodiment, the methods comprise a compound of formula 34 and the attendant definitions wherein R is 3,5-dichloro-2-hydroxyphenyl.

In a further embodiment, the methods comprise a compound of formula 34 and the attendant definitions wherein $R_1$ is H.

In a further embodiment, the methods comprise a compound of formula 34 and the attendant definitions wherein $R_2$ is H.

In a further embodiment, the methods comprise a compound of formula 34 and the attendant definitions wherein n is 1.

In a further embodiment, the methods comprise a compound of formula 34 and the attendant definitions wherein R is 3,5-dichloro-2-hydroxyphenyl and $R_1$ is H.

In a further embodiment, the methods comprise a compound of formula 34 and the attendant definitions wherein R is 3,5-dichloro-2-hydroxyphenyl, $R_1$ is H, and $R_2$ is H.

In a further embodiment, the methods comprise a compound of formula 34 and the attendant definitions wherein R is 3,5-dichloro-2-hydroxyphenyl, $R_1$ is H, $R_2$ is H, and n is 1.

In another embodiment, methods for activating a sirtuin protein comprise using an activating compound of formula 35:

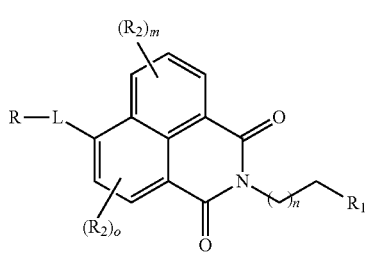

35 wherein, independently for each occurrence:

R is H or a substituted or unsubstituted alkyl, aryl, aralkyl, heterocyclyl, heterocyclylalkyl, heteroaryl, or heteroaralkyl;

$R_1$ is a substituted or unsubstituted alkyl, aryl, aralkyl, heterocyclyl, heterocyclylalkyl, heteroaryl, or heteroaralkyl;

$R_2$ is hydroxy, amino, cyano, halide, $OR_3$, ether, ester, amido, ketone, carboxylic acid, nitro, or a substituted or unsubstituted alkyl, aryl, aralkyl, heterocyclyl, heterocyclylalkyl, heteroaryl, heteroaralkyl;

$R_3$ is alkyl, —$SO_3H$, monosaccharide, oligosaccharide, glycofuranosyl, glycopyranosyl, glucuronosyl, or glucuronide;

L is O, NR, or S;

m is an integer from 0 to 3 inclusive;

n is an integer from 0 to 5 inclusive; and o is an integer from 0 to 2 inclusive.

In a further embodiment, the methods comprise a compound of formula 35 and the attendant definitions wherein R is phenyl.

In a further embodiment, the methods comprise a compound of formula 35 and the attendant definitions wherein $R_1$ is pyridine.

In a further embodiment, the methods comprise a compound of formula 35 and the attendant definitions wherein L is S.

In a further embodiment, the methods comprise a compound of formula 35 and the attendant definitions wherein m is 0.

In a further embodiment, the methods comprise a compound of formula 35 and the attendant definitions wherein n is 1.

In a further embodiment, the methods comprise a compound of formula 35 and the attendant definitions wherein o is 0.

In a further embodiment, the methods comprise a compound of formula 35 and the attendant definitions wherein R is phenyl and $R_1$ is pyridine.

In a further embodiment, the methods comprise a compound of formula 35 and the attendant definitions wherein R is phenyl, $R_1$ is pyridine, and L is S.

In a further embodiment, the methods comprise a compound of formula 35 and the attendant definitions wherein R is phenyl, $R_1$ is pyridine, L is S, and m is 0.

In a further embodiment, the methods comprise a compound of formula 35 and the attendant definitions wherein R is phenyl, $R_1$ is pyridine, L is S, m is 0, and n is 1.

In a further embodiment, the methods comprise a compound of formula 35 and the attendant definitions wherein R is phenyl, $R_1$ is pyridine, L is S, m is 0, n is 1, and o is 0.

In another embodiment, methods for activating a sirtuin protein comprise using an activating compound of formula 36:

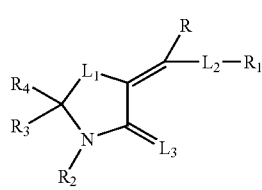

36 wherein, independently for each occurrence:

R, $R_3$, and $R_4$ are H, hydroxy, amino, cyano, halide, $OR_5$, ether, ester, amido, ketone, carboxylic acid, nitro, or a substituted or unsubstituted alkyl, aryl, aralkyl, heterocyclyl, heterocyclylalkyl, heteroaryl, heteroaralkyl;

$R_5$ is alkyl, —$SO_3H$, monosaccharide, oligosaccharide, glycofuranosyl, glycopyranosyl, glucuronosyl, or glucuronide;

$R_1$ and $R_2$ are H or a substituted or unsubstituted alkyl, aryl, aralkyl, heterocyclyl, heterocyclylalkyl, heteroaryl, heteroaralkyl;

$L_1$ is O, $NR_1$, S, $C(R)_2$, or $SO_2$; and $L_2$ and $L_3$ are O, $NR_1$, S, or $C(R)_2$.

In a further embodiment, the methods comprise a compound of formula 36 and the attendant definitions wherein R is H.

In a further embodiment, the methods comprise a compound of formula 36 and the attendant definitions wherein $R_1$ is 4-chlorophenyl.

In a further embodiment, the methods comprise a compound of formula 36 and the attendant definitions wherein $R_2$ is 4-chlorophenyl.

In a further embodiment, the methods comprise a compound of formula 36 and the attendant definitions wherein $R_3$ is H.

In a further embodiment, the methods comprise a compound of formula 36 and the attendant definitions wherein $R_4$ is H.

In a further embodiment, the methods comprise a compound of formula 36 and the attendant definitions wherein $L_1$ is $SO_2$.

In a further embodiment, the methods comprise a compound of formula 36 and the attendant definitions wherein $L_2$ is NH.

In a further embodiment, the methods comprise a compound of formula 36 and the attendant definitions wherein $L_3$ is O.

In a further embodiment, the methods comprise a compound of formula 36 and the attendant definitions wherein R is H and $R_1$ is 4-chlorophenyl.

In a further embodiment, the methods comprise a compound of formula 36 and the attendant definitions wherein R is H, $R_1$ is 4-chlorophenyl, and $R_2$ is 4-chlorophenyl.

In a further embodiment, the methods comprise a compound of formula 36 and the attendant definitions wherein R is H, R₁ is 4-chlorophenyl, R₂ is 4-chlorophenyl, and R₃ is H.

In a further embodiment, the methods comprise a compound of formula 36 and the attendant definitions wherein R is H, R₁ is 4-chlorophenyl, R₂ is 4-chlorophenyl, R₃ is H, and R₄ is H.

In a further embodiment, the methods comprise a compound of formula 36 and the attendant definitions wherein R is H, R₁ is 4-chlorophenyl, R₂ is 4-chlorophenyl, R₃ is H, R₄ is H, and L₁ is SO₂.

In a further embodiment, the methods comprise a compound of formula 36 and the attendant definitions wherein R is H, R₁ is 4-chlorophenyl, R₂ is 4-chlorophenyl, R₃ is H, R₄ is H, L₁ is SO₂, and L₂ is NH.

In a further embodiment, the methods comprise a compound of formula 36 and the attendant definitions wherein R is H, R₁ is 4-chlorophenyl, R₂ is 4-chlorophenyl, R₃ is H, R₄ is H, L₁ is SO₂, L₂ is NH, and L₃ is O.

In another embodiment, methods for activating a sirtuin protein comprise using an activating compound of formula 37:

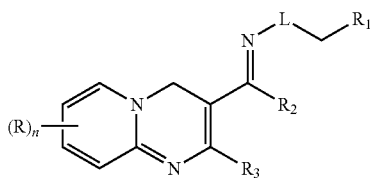

wherein, independently for each occurrence:

R is hydroxy, amino, cyano, halide, OR₄, ether, ester, amido, ketone, carboxylic acid, nitro, or a substituted or unsubstituted alkyl, aryl, aralkyl, heterocyclyl, heterocyclylalkyl, heteroaryl, heteroaralkyl;

R₁ is H or a substituted or unsubstituted alkyl, aryl, aralkyl, heterocyclyl, heterocyclylalkyl, heteroaryl, heteroaralkyl;

R₂ and R₃ are H or a substituted or unsubstituted alkyl, aryl, aralkyl, heterocyclyl, heterocyclylalkyl, heteroaryl, heteroaralkyl;

R₄ is alkyl, —SO₃H, monosaccharide, oligosaccharide, glycofuranosyl, glycopyranosyl, glucuronosyl, or glucuronide;

L is O, NR₁, or S; and n is an integer from 0 to 4 inclusive.

In a further embodiment, the methods comprise a compound of formula 37 and the attendant definitions wherein R is methyl.

In a further embodiment, the methods comprise a compound of formula 37 and the attendant definitions wherein n is 1.

In a further embodiment, the methods comprise a compound of formula 37 and the attendant definitions wherein R₁ is 3-fluorophenyl.

In a further embodiment, the methods comprise a compound of formula 37 and the attendant definitions wherein R₂ is H.

In a further embodiment, the methods comprise a compound of formula 37 and the attendant definitions wherein R₃ is 4-chlorophenyl.

In a further embodiment, the methods comprise a compound of formula 37 and the attendant definitions wherein L is O.

In a further embodiment, the methods comprise a compound of formula 37 and the attendant definitions wherein R is methyl and n is 1.

In a further embodiment, the methods comprise a compound of formula 37 and the attendant definitions wherein R is methyl, n is 1, and R₁ is 3-fluorophenyl.

In a further embodiment, the methods comprise a compound of formula 37 and the attendant definitions wherein R is methyl, n is 1, R₁ is 3-fluorophenyl, and R₂ is H.

In a further embodiment, the methods comprise a compound of formula 37 and the attendant definitions wherein R is methyl, n is 1, R₁ is 3-fluorophenyl, R₂ is H, and R₃ is 4-chlorophenyl.

In another embodiment, methods for activating a sirtuin protein comprise using an activating compound of formula 38:

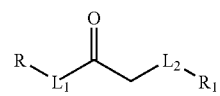

wherein, independently for each occurrence:

R and R₁ are H or a substituted or unsubstituted alkyl, aryl, aralkyl, heterocyclyl, heterocyclylalkyl, heteroaryl, or heteroaralkyl; and L₁ and L₂ are O, NR, or S.

In a further embodiment, the methods comprise a compound of formula 38 and the attendant definitions wherein R is 3-methoxyphenyl.

In a further embodiment, the methods comprise a compound of formula 38 and the attendant definitions wherein R₁ is 4-t-butylphenyl.

In a further embodiment, the methods comprise a compound of formula 38 and the attendant definitions wherein L₁ is NH.

In a further embodiment, the methods comprise a compound of formula 38 and the attendant definitions wherein L₂ is O.

In a further embodiment, the methods comprise a compound of formula 38 and the attendant definitions wherein R is 3-methoxyphenyl and R₁ is 4-t-butylphenyl.

In a further embodiment, the methods comprise a compound of formula 38 and the attendant definitions wherein R is 3-methoxyphenyl, R₁ is 4-t-butylphenyl, and L₁ is NH.

In a further embodiment, the methods comprise a compound of formula 38 and the attendant definitions wherein R is 3-methoxyphenyl, R₁ is 4-t-butylphenyl, L₁ is NH, and L₂ is O.

In another embodiment, methods for activating a sirtuin protein comprise using an activating compound of formula 39:

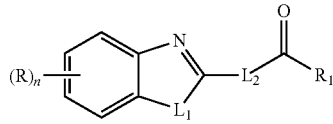

wherein, independently for each occurrence:

R is H, hydroxy, amino, cyano, halide, OR₂, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_1$ is H or a substituted or unsubstituted alkyl, aryl, alkaryl, heterocyclyl, heterocyclylalkyl, heteroaryl, or heteroaralkyl;

$R_2$ is alkyl, —$SO_3H$, monosaccharide, oligosaccharide, glycofuranosyl, glycopyranosyl, glucuronosyl, or glucuronide;

$L_1$ and $L_2$ are O, NR, or S; and n is an integer from 0 to 4 inclusive.

In a further embodiment, the methods comprise a compound of formula 39 and the attendant definitions wherein R is methyl.

In a further embodiment, the methods comprise a compound of formula 39 and the attendant definitions wherein n is 1.

In a further embodiment, the methods comprise a compound of formula 39 and the attendant definitions wherein $R_1$ is 3,4,5-trimethoxyphenyl.

In a further embodiment, the methods comprise a compound of formula 39 and the attendant definitions wherein $L_1$ is S.

In a further embodiment, the methods comprise a compound of formula 39 and the attendant definitions wherein $L_2$ is NH.

In a further embodiment, the methods comprise a compound of formula 39 and the attendant definitions wherein R is methyl and n is 1.

In a further embodiment, the methods comprise a compound of formula 39 and the attendant definitions wherein R is methyl, n is 1, and $R_1$ is 3,4,5-trimethoxyphenyl.

In a further embodiment, the methods comprise a compound of formula 39 and the attendant definitions wherein R is methyl, n is 1, $R_1$ is 3,4,5-trimethoxyphenyl, and $L_1$ is S.

In a further embodiment, the methods comprise a compound of formula 39 and the attendant definitions wherein R is methyl, n is 1, $R_1$ is 3,4,5-trimethoxyphenyl, $L_1$ is S, and $L_2$ is NH.

In another embodiment, methods for activating a sirtuin protein comprise using an activating compound of formula 40:

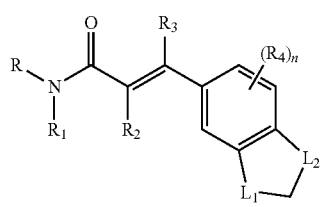

wherein, independently for each occurrence:

R, $R_1$, $R_2$, $R_3$ are H or a substituted or unsubstituted alkyl, aryl, alkaryl, heterocyclyl, heterocyclylalkyl, heteroaryl, or heteroaralkyl;

$R_4$ is hydroxy, amino, cyano, halide, $OR_5$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_5$ is alkyl, —$SO_3H$, monosaccharide, oligosaccharide, glycofuranosyl, glycopyranosyl, glucuronosyl, or glucuronide;

$L_1$ and $L_2$ are O, NR, or S; and n is an integer from 0 to 3 inclusive.

In a further embodiment, the methods comprise a compound of formula 40 and the attendant definitions wherein R is H.

In a further embodiment, the methods comprise a compound of formula 40 and the attendant definitions wherein $R_1$ is perfluorophenyl.

In a further embodiment, the methods comprise a compound of formula 40 and the attendant definitions wherein $R_2$ is H.

In a further embodiment, the methods comprise a compound of formula 40 and the attendant definitions wherein $R_3$ is H.

In a further embodiment, the methods comprise a compound of formula 40 and the attendant definitions wherein $L_1$ is O.

In a further embodiment, the methods comprise a compound of formula 40 and the attendant definitions wherein $L_2$ is O.

In a further embodiment, the methods comprise a compound of formula 40 and the attendant definitions wherein n is 0.

In a further embodiment, the methods comprise a compound of formula 40 and the attendant definitions wherein R is H and $R_1$ is perfluorophenyl.

In a further embodiment, the methods comprise a compound of formula 40 and the attendant definitions wherein R is H, $R_1$ is perfluorophenyl, and $R_2$ is H.

In a further embodiment, the methods comprise a compound of formula 40 and the attendant definitions R is H, $R_1$ is perfluorophenyl, $R_2$ is H, and $R_3$ is H.

In a further embodiment, the methods comprise a compound of formula 40 and the attendant definitions wherein R is H, $R_1$ is perfluorophenyl, $R_2$ is H, $R_3$ is H, and $L_1$ is O.

In a further embodiment, the methods comprise a compound of formula 40 and the attendant definitions wherein R is H, $R_K$ is perfluorophenyl, $R_2$ is H, $R_3$ is H, $L_1$ is O, and $L_2$ is O.

In a further embodiment, the methods comprise a compound of formula 40 and the attendant definitions wherein R is H, $R_1$ is perfluorophenyl, $R_2$ is H, $R_3$ is H, $L_1$ is O, $L_2$ is O, and n is 0.

In another embodiment, methods for activating a sirtuin protein comprise using an activating compound of formula 41:

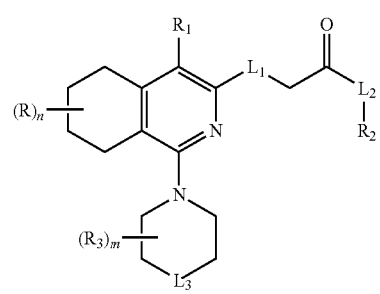

wherein, independently for each occurrence:

R, $R_1$, and $R_3$ are hydroxy, amino, cyano, halide, $OR_4$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_2$ is H or a substituted or unsubstituted alkyl, aryl, aralkyl, heterocyclyl, heterocyclylalkyl, heteroaryl, or heteroaralkyl;

$R_4$ is alkyl, —$SO_3H$, monosaccharide, oligosaccharide, glycofuranosyl, glycopyranosyl, glucuronosyl, or glucuronide;

$L_1$, $L_2$, and $L_3$ are O, $NR_2$, or S; and m and n are integers from 0 to 8 inclusive.

In a further embodiment, the methods comprise a compound of formula 41 and the attendant definitions wherein n is 0.

In a further embodiment, the methods comprise a compound of formula 41 and the attendant definitions wherein $R_1$ is cyano.

In a further embodiment, the methods comprise a compound of formula 41 and the attendant definitions wherein $R_2$ is ethyl.

In a further embodiment, the methods comprise a compound of formula 41 and the attendant definitions wherein m is 0.

In a further embodiment, the methods comprise a compound of formula 41 and the attendant definitions wherein $L_1$ is S.

In a further embodiment, the methods comprise a compound of formula 41 and the attendant definitions wherein $L_2$ is O.

In a further embodiment, the methods comprise a compound of formula 41 and the attendant definitions wherein $L_3$ is O.

In a further embodiment, the methods comprise a compound of formula 41 and the attendant definitions wherein n is 0 and $R_1$ is cyano.

In a further embodiment, the methods comprise a compound of formula 41 and the attendant definitions wherein n is 0, $R_1$ is cyano, and $R_2$ is ethyl.

In a further embodiment, the methods comprise a compound of formula 41 and the attendant definitions wherein n is 0, $R_1$ is cyano, $R_2$ is ethyl, and m is 0.

In a further embodiment, the methods comprise a compound of formula 41 and the attendant definitions wherein n is 0, $R_1$ is cyano, $R_2$ is ethyl, m is 0, and $L_1$ is S.

In a further embodiment, the methods comprise a compound of formula 41 and the attendant definitions wherein n is 0, $R_1$ is cyano, $R_2$ is ethyl, m is 0, $L_1$ is S, and $L_2$ is O.

In a further embodiment, the methods comprise a compound of formula 41 and the attendant definitions wherein n is 0, $R_1$ is cyano, $R_2$ is ethyl, m is 0, $L_1$ is S, $L_2$ is O, and $L_3$ is O.

In another embodiment, methods for activating a sirtuin protein comprise using an activating compound of formula 42:

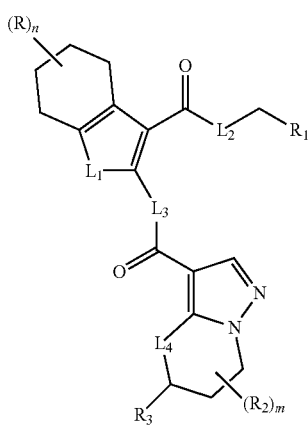

wherein, independently for each occurrence:

R and $R_2$ are H, hydroxy, amino, cyano, halide, $OR_4$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_1$ and $R_3$ are H or a substituted or unsubstituted alkyl, aryl, aralkyl, heterocyclyl, heterocyclylalkyl, heteroaryl, or heteroaralkyl;

$R_4$ is alkyl, —$SO_3H$, monosaccharide, oligosaccharide, glycofuranosyl, glycopyranosyl, glucuronosyl, or glucuronide;

$L_1$, $L_2$, $L_3$, and $L_4$ are O, $NR_1$, or S;

m is an integer from 0 to 6 inclusive; and n is an integer from 0 to 8 inclusive.

In a further embodiment, the methods comprise a compound of formula 42 and the attendant definitions wherein n is 0.

In a further embodiment, the methods comprise a compound of formula 42 and the attendant definitions wherein $R_1$ is methyl.

In a further embodiment, the methods comprise a compound of formula 42 and the attendant definitions wherein $R_2$ is $CF_3$ and m is 1.

In a further embodiment, the methods comprise a compound of formula 42 and the attendant definitions wherein $R_3$ is 4-methylphenyl.

In a further embodiment, the methods comprise a compound of formula 42 and the attendant definitions wherein $L_1$ is S.

In a further embodiment, the methods comprise a compound of formula 42 and the attendant definitions wherein $L_2$ is O.

In a further embodiment, the methods comprise a compound of formula 42 and the attendant definitions wherein $L_3$ is $NR_1$.

In a further embodiment, the methods comprise a compound of formula 42 and the attendant definitions wherein $L_4$ is $NR_1$.

In a further embodiment, the methods comprise a compound of formula 42 and the attendant definitions wherein n is 0 and $R_1$ is methyl.

In a further embodiment, the methods comprise a compound of formula 42 and the attendant definitions wherein n is 0, $R_1$ is methyl, $R_2$ is $CF_3$, and m is 1.

In a further embodiment, the methods comprise a compound of formula 42 and the attendant definitions wherein n is 0, $R_1$ is methyl, $R_2$ is $CF_3$, m is 1; and $R_3$ is 4-methylphenyl.

In a further embodiment, the methods comprise a compound of formula 42 and the attendant definitions wherein n is 0, $R_1$ is methyl, $R_2$ is $CF_3$, m is 1; $R_3$ is 4-methylphenyl; and $L_1$ is S.

In a further embodiment, the methods comprise a compound of formula 42 and the attendant definitions wherein n is 0, $R_1$ is methyl, $R_2$ is $CF_3$, m is 1; $R_3$ is 4-methylphenyl; $L_1$ is S, and $L_2$ is O.

In a further embodiment, the methods comprise a compound of formula 42 and the attendant definitions wherein n is 0, $R_1$ is methyl, $R_2$ is $CF_3$, m is 1; $R_3$ is 4-methylphenyl; $L_1$ is S, $L_2$ is O; and $L_3$ is $NR_1$.

In a further embodiment, the methods comprise a compound of formula 42 and the attendant definitions wherein n is 0, $R_1$ is methyl, $R_2$ is $CF_3$, m is 1; $R_3$ is 4-methylphenyl; $L_1$ is S, $L_2$ is O; $L_3$ is $NR_1$, and $L_4$ is $NR_1$.

In another embodiment, methods for activating a sirtuin protein comprise using an activating compound of formula 43:

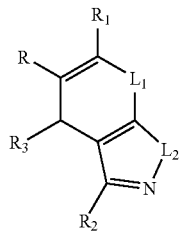

43 wherein, independently for each occurrence:

R and $R_1$ are hydroxy, amino, cyano, halide, $OR_4$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_2$ and $R_3$ are H or a substituted or unsubstituted alkyl, aryl, aralkyl, heterocyclyl, heterocyclylalkyl, heteroaryl, or heteroaralkyl;

$R_4$ is alkyl, —$SO_3H$, monosaccharide, oligosaccharide, glycofuranosyl, glycopyranosyl, glucuronosyl, or glucuronide; and $L_1$ and $L_2$ are O, $NR_2$, or S.

In a further embodiment, the methods comprise a compound of formula 43 and the attendant definitions wherein R is cyano.

In a further embodiment, the methods comprise a compound of formula 43 and the attendant definitions wherein $R_1$ is $NH_2$.

In a further embodiment, the methods comprise a compound of formula 43 and the attendant definitions wherein $R_2$ is 4-bromophenyl.

In a further embodiment, the methods comprise a compound of formula 43 and the attendant definitions wherein $R_3$ is 3-hydroxy-4-methoxyphenyl.

In a further embodiment, the methods comprise a compound of formula 43 and the attendant definitions wherein $L_1$ is O.

In a further embodiment, the methods comprise a compound of formula 43 and the attendant definitions wherein $L_2$ is $NR_2$.

In a further embodiment, the methods comprise a compound of formula 43 and the attendant definitions wherein R is cyano and $R_1$ is $NH_2$.

In a further embodiment, the methods comprise a compound of formula 43 and the attendant definitions wherein R is cyano, $R_1$ is $NH_2$, and $R_2$ is 4-bromophenyl.

In a further embodiment, the methods comprise a compound of formula 43 and the attendant definitions wherein R is cyano, $R_1$ is $NH_2$, $R_2$ is 4-bromophenyl, and $R_3$ is 3-hydroxy-4-methoxyphenyl.

In a further embodiment, the methods comprise a compound of formula 43 and the attendant definitions wherein R is cyano, $R_1$ is $NH_2$, $R_2$ is 4-bromophenyl, $R_3$ is 3-hydroxy-4-methoxyphenyl, and $L_1$ is O.

In a further embodiment, the methods comprise a compound of formula 43 and the attendant definitions wherein R is cyano, $R_1$ is $NH_2$, $R_2$ is 4-bromophenyl, $R_3$ is 3-hydroxy-4-methoxyphenyl, $L_1$ is O, and $L_2$ is $NR_2$.

In another embodiment, methods for activating a sirtuin protein comprise using an activating compound of formula 44:

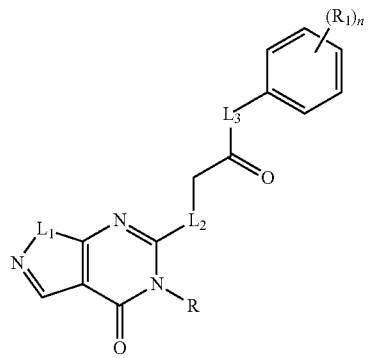

44 wherein, independently for each occurrence:

R is H or a substituted or unsubstituted alkyl, aryl, aralkyl, heterocyclyl, heterocyclylalkyl, heteroaryl, or heteroaralkyl;

$R_1$ is hydroxy, amino, cyano, halide, $OR_2$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_2$ is alkyl, —$SO_3H$, monosaccharide, oligosaccharide, glycofuranosyl, glycopyranosyl, glucuronosyl, or glucuronide;

$L_1$, $L_2$, and $L_3$ are O, NR, or S; and n is an integer from 0 to 5 inclusive.

In a further embodiment, the methods comprise a compound of formula 44 and the attendant definitions wherein R is 3-trifluoromethylphenyl.

In a further embodiment, the methods comprise a compound of formula 44 and the attendant definitions wherein $R_1$ is $C(O)OCH_3$.

In a further embodiment, the methods comprise a compound of formula 44 and the attendant definitions wherein $L_1$ is NR.

In a further embodiment, the methods comprise a compound of formula 44 and the attendant definitions wherein $L_2$ is S.

In a further embodiment, the methods comprise a compound of formula 44 and the attendant definitions wherein $L_3$ is NR.

In a further embodiment, the methods comprise a compound of formula 44 and the attendant definitions wherein n is 2.

In a further embodiment, the methods comprise a compound of formula 44 and the attendant definitions wherein R is 3-trifluoromethylphenyl and $R_1$ is $C(O)OCH_3$.

In a further embodiment, the methods comprise a compound of formula 44 and the attendant definitions wherein R is 3-trifluoromethylphenyl, $R_1$ is $C(O)OCH_3$, and $L_1$ is NR.

In a further embodiment, the methods comprise a compound of formula 44 and the attendant definitions wherein R is 3-trifluoromethylphenyl, $R_1$ is $C(O)OCH_3$, $L_1$ is NR, and $L_2$ is S.

In a further embodiment, the methods comprise a compound of formula 44 and the attendant definitions wherein R is 3-trifluoromethylphenyl, $R_1$ is $C(O)OCH_3$, $L_1$ is NR, $L_2$ is S, and $L_3$ is NR.

In a further embodiment, the methods comprise a compound of formula 44 and the attendant definitions wherein R is 3-trifluoromethylphenyl, $R_1$ is $C(O)OCH_3$, $L_1$ is NR, $L_2$ is S, $L_3$ is NR, and n is 2.

In another embodiment, methods for activating a sirtuin protein comprise using an activating compound of formula 45:

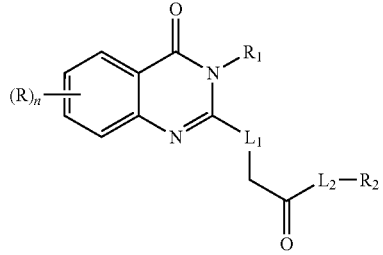

45 wherein, independently for each occurrence:

R is hydroxy, amino, cyano, halide, $OR_3$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_1$ and $R_2$ are H or a substituted or unsubstituted alkyl, aryl, aralkyl, heterocyclyl, heterocyclylalkyl, heteroaryl, or heteroaralkyl;

$R_3$ is alkyl, —$SO_3H$, monosaccharide, oligosaccharide, glycofuranosyl, glycopyranosyl, glucuronosyl, or glucuronide;

$L_1$ and $L_2$ are O, $NR_1$, or S; and n is an integer from 0 to 4 inclusive.

In a further embodiment, the methods comprise a compound of formula 45 and the attendant definitions wherein n is 0.

In a further embodiment, the methods comprise a compound of formula 45 and the attendant definitions wherein $R_1$ is 2-tetrahydrofuranylmethyl.

In a further embodiment, the methods comprise a compound of formula 45 and the attendant definitions wherein $R_2$ is —$CH_2CH_2C_6H_4SO_2NH_2$.

In a further embodiment, the methods comprise a compound of formula 45 and the attendant definitions wherein $L_1$ is S.

In a further embodiment, the methods comprise a compound of formula 45 and the attendant definitions wherein $L_2$ is $NR_1$.

In a further embodiment, the methods comprise a compound of formula 45 and the attendant definitions wherein n is 0 and $R_1$ is 2-tetrahydrofuranylmethyl.

In a further embodiment, the methods comprise a compound of formula 45 and the attendant definitions wherein n is 0, $R_1$ is 2-tetrahydrofuranylmethyl, and $R_2$ is —$CH_2CH_2C_6H_4SO_2NH_2$.

In a further embodiment, the methods comprise a compound of formula 45 and the attendant definitions wherein n is 0, $R_1$ is 2-tetrahydrofuranylmethyl, $R_2$ is —$CH_2CH_2C_6H_4SO_2NH_2$, and $L_1$ is S.

In a further embodiment, the methods comprise a compound of formula 45 and the attendant definitions wherein n is 0, $R_1$ is 2-tetrahydrofuranylmethyl, $R_2$ is —$CH_2CH_2C_6H_4SO_2NH_2$, $L_1$ is S, and $L_2$ is $NR_1$.

In another embodiment, methods for activating a sirtuin protein comprise using an activating compound of formula 46:

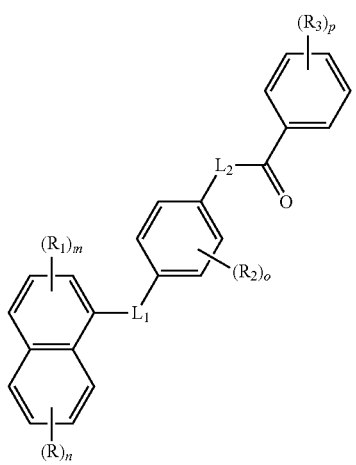

46 wherein, independently for each occurrence:

R, $R_1$, $R_2$, and $R_3$ are hydroxy, amino, cyano, halide, $OR_5$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_5$ is alkyl, —$SO_3H$, monosaccharide, oligosaccharide, glycofuranosyl, glycopyranosyl, glucuronosyl, or glucuronide;

$L_1$ and $L_2$ are O, $NR_4$, or S;

$R_4$ is H or a substituted or unsubstituted alkyl, aryl, aralkyl, heterocyclyl, heterocyclylalkyl, heteroaryl, or heteroaralkyl;

n is an integer from 0 to 4 inclusive;

m is an integer from 0 to 3 inclusive;

o is an integer from 0 to 4 inclusive; and p is an integer from 0 to 5 inclusive.

In a further embodiment, the methods comprise a compound of formula 46 and the attendant definitions wherein n is 0.

In a further embodiment, the methods comprise a compound of formula 46 and the attendant definitions wherein m is 1.

In a further embodiment, the methods comprise a compound of formula 46 and the attendant definitions wherein $R_1$ is Cl.

In a further embodiment, the methods comprise a compound of formula 46 and the attendant definitions wherein o is 1.

In a further embodiment, the methods comprise a compound of formula 46 and the attendant definitions wherein $R_2$ is Cl.

In a further embodiment, the methods comprise a compound of formula 46 and the attendant definitions wherein p is 3.

In a further embodiment, the methods comprise a compound of formula 46 and the attendant definitions wherein $R_3$ is OH or I.

In a further embodiment, the methods comprise a compound of formula 46 and the attendant definitions wherein n is 0 and m is 1.

In a further embodiment, the methods comprise a compound of formula 46 and the attendant definitions wherein n is 0, m is 1, and o is 1.

In a further embodiment, the methods comprise a compound of formula 46 and the attendant definitions wherein n is 0, m is 1, o is 1, and $R_1$ is Cl.

In a further embodiment, the methods comprise a compound of formula 46 and the attendant definitions wherein n is 0, m is 1, o is 1, $R_1$ is Cl, and p is 3.

In a further embodiment, the methods comprise a compound of formula 46 and the attendant definitions wherein n is 0, m is 1, o is 1, $R_1$ is Cl, p is 3, and $R_2$ is OH or I.

In another embodiment, methods for activating a sirtuin protein comprise using an activating compound of formula 47:

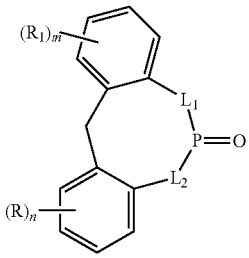

47 wherein, independently for each occurrence:

R and $R_1$ are hydroxy, amino, cyano, halide, $OR_5$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$L_1$ and $L_2$ are O, $NR_4$, or S;

$R_4$ is H or a substituted or unsubstituted alkyl, aryl, aralkyl, heterocyclyl, heterocyclylalkyl, heteroaryl, or heteroaralkyl;

$R_5$ is alkyl, —$SO_3H$, monosaccharide, oligosaccharide, glycofuranosyl, glycopyranosyl, glucuronosyl, or glucuronide; and m and n are integers from 0 to 4 inclusive.

In a further embodiment, the methods comprise a compound of formula 47 and the attendant definitions wherein n is 2.

In a further embodiment, the methods comprise a compound of formula 47 and the attendant definitions wherein R is methyl or t-butyl.

In a further embodiment, the methods comprise a compound of formula 47 and the attendant definitions wherein m is 2.

In a further embodiment, the methods comprise a compound of formula 47 and the attendant definitions wherein $R_1$ is methyl or t-butyl.

In a further embodiment, the methods comprise a compound of formula 47 and the attendant definitions wherein $L_1$ is O.

In a further embodiment, the methods comprise a compound of formula 47 and the attendant definitions wherein $L_2$ is O.

In a further embodiment, the methods comprise a compound of formula 47 and the attendant definitions wherein n is 2 and R is methyl or t-butyl.

In a further embodiment, the methods comprise a compound of formula 47 and the attendant definitions wherein n is 2, R is methyl or t-butyl, and m is 2.

In a further embodiment, the methods comprise a compound of formula 47 and the attendant definitions wherein n is 2, R is methyl or t-butyl, m is 2, and $R_1$ is methyl or t-butyl.

In a further embodiment, the methods comprise a compound of formula 47 and the attendant definitions wherein n is 2, R is methyl or t-butyl, m is 2, $R_1$ is methyl or t-butyl, and $L_1$ is O.

In a further embodiment, the methods comprise a compound of formula 47 and the attendant definitions wherein n is 2, R is methyl or t-butyl, m is 2, $R_1$ is methyl or t-butyl, $L_1$ is O, and $L_2$ is O.

In another embodiment, methods for activating a sirtuin protein comprise using an activating compound of formula 48:

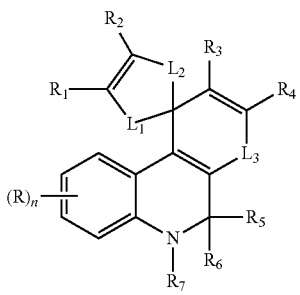

48 wherein, independently for each occurrence:

R, $R_1$, $R_2$, $R_3$, $R_4$, $R_5$, and $R_6$ are hydroxy, amino, cyano, halide, $OR_8$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_7$ is H or a substituted or unsubstituted alkyl, acyl, aryl, aralkyl, heterocyclyl, heterocyclylalkyl, heteroaryl, or heteroaralkyl;

$R_8$ is alkyl, —$SO_3H$, monosaccharide, oligosaccharide, glycofuranosyl, glycopyranosyl, glucuronosyl, or glucuronide;

$L_1$, $L_2$, and $L_3$ are O, $NR_7$, or S and n is an integer from 0 to 4 inclusive.

In a further embodiment, the methods comprise a compound of formula 48 and the attendant definitions wherein n is 1.

In a further embodiment, the methods comprise a compound of formula 48 and the attendant definitions wherein R is methyl.

In a further embodiment, the methods comprise a compound of formula 48 and the attendant definitions wherein $R_1$ is $C(O)OCH_3$.

In a further embodiment, the methods comprise a compound of formula 48 and the attendant definitions wherein $R_2$ is $C(O)OCH_3$.

In a further embodiment, the methods comprise a compound of formula 48 and the attendant definitions wherein $R_3$ is $C(O)OCH_3$.

In a further embodiment, the methods comprise a compound of formula 48 and the attendant definitions wherein $R_4$ is $C(O)OCH_3$.

In a further embodiment, the methods comprise a compound of formula 48 and the attendant definitions wherein $R_5$ is methyl.

In a further embodiment, the methods comprise a compound of formula 48 and the attendant definitions wherein $R_6$ is methyl.

In a further embodiment, the methods comprise a compound of formula 48 and the attendant definitions wherein $R_7$ is $C(O)CF_3$.

In a further embodiment, the methods comprise a compound of formula 48 and the attendant definitions wherein $L_1$ is S.

In a further embodiment, the methods comprise a compound of formula 48 and the attendant definitions wherein $L_2$ is S.

In a further embodiment, the methods comprise a compound of formula 48 and the attendant definitions wherein $L_3$ is S.

In a further embodiment, the methods comprise a compound of formula 48 and the attendant definitions wherein n is 1 and R is methyl.

In a further embodiment, the methods comprise a compound of formula 48 and the attendant definitions wherein n is 1, R is methyl, and $R_1$ is $C(O)OCH_3$.

In a further embodiment, the methods comprise a compound of formula 48 and the attendant definitions wherein n is 1, R is methyl, $R_1$ is $C(O)OCH_3$, and $R_2$ is $C(O)OCH_3$.

In a further embodiment, the methods comprise a compound of formula 48 and the attendant definitions wherein n is 1, R is methyl, $R_1$ is $C(O)OCH_3$, $R_2$ is $C(O)OCH_3$, and $R_3$ is $C(O)OCH_3$.

In a further embodiment, the methods comprise a compound of formula 48 and the attendant definitions wherein n is 1, R is methyl, $R_1$ is $C(O)OCH_3$, $R_2$ is $C(O)OCH_3$, $R_3$ is $C(O)OCH_3$, and $R_4$ is $C(O)OCH_3$.

In a further embodiment, the methods comprise a compound of formula 48 and the attendant definitions wherein n is 1, R is methyl, $R_1$ is $C(O)OCH_3$, $R_2$ is $C(O)OCH_3$, $R_3$ is $C(O)OCH_3$, $R_4$ is $C(O)OCH_3$, and $R_5$ is methyl.

In a further embodiment, the methods comprise a compound of formula 48 and the attendant definitions wherein n is 1, R is methyl, $R_1$ is $C(O)OCH_3$, $R_2$ is $C(O)OCH_3$, $R_3$ is $C(O)OCH_3$, $R_4$ is $C(O)OCH_3$, $R_5$ is methyl, and $R_6$ is methyl.

In a further embodiment, the methods comprise a compound of formula 48 and the attendant definitions wherein n is 1, R is methyl, $R_1$ is $C(O)OCH_3$, $R_2$ is $C(O)OCH_3$, $R_3$ is $C(O)OCH_3$, $R_4$ is $C(O)OCH_3$, $R_5$ is methyl, $R_6$ is methyl, and $R_7$ is $C(O)CF_3$.

In a further embodiment, the methods comprise a compound of formula 48 and the attendant definitions wherein n is 1, R is methyl, $R_1$ is $C(O)OCH_3$, $R_2$ is $C(O)OCH_3$, $R_3$ is $C(O)OCH_3$, $R_4$ is $C(O)OCH_3$, $R_5$ is methyl, $R_6$ is methyl, $R_7$ is $C(O)CF_3$, and $L_1$ is S.

In a further embodiment, the methods comprise a compound of formula 48 and the attendant definitions wherein n is 1, R is methyl, $R_1$ is $C(O)OCH_3$, $R_2$ is $C(O)OCH_3$, $R_3$ is $C(O)OCH_3$, $R_4$ is $C(O)OCH_3$, $R_5$ is methyl, $R_6$ is methyl, $R_7$ is $C(O)CF_3$, $L_1$ is S, and $L_2$ is S.

In a further embodiment, the methods comprise a compound of formula 48 and the attendant definitions wherein n is 1, R is methyl, $R_1$ is $C(O)OCH_3$, $R_2$ is $C(O)OCH_3$, $R_3$ is $C(O)OCH_3$, $R_4$ is $C(O)OCH_3$, $R_5$ is methyl, $R_6$ is methyl, $R_7$ is $C(O)CF_3$, $L_1$ is S, $L_2$ is S, and $L_3$ is S.

In another embodiment, methods for activating a sirtuin protein comprise using an activating compound of formula 49:

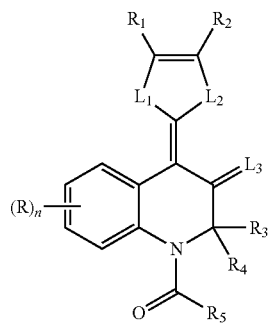

49 wherein, independently for each occurrence:

R, $R_1$, $R_2$, $R_3$, $R_4$, and $R_5$ are hydroxy, amino, cyano, halide, $OR_7$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$L_1$, $L_2$, and $L_3$ are O, $NR_6$, or S;

$R_6$ is H or a substituted or unsubstituted alkyl, aryl, aralkyl, heterocyclyl, heterocyclylalkyl, heteroaryl, or heteroaralkyl;

$R_7$ is alkyl, —$SO_3H$, monosaccharide, oligosaccharide, glycofuranosyl, glycopyranosyl, glucuronosyl, or glucuronide; and n is an integer from 0 to 4 inclusive.

In a further embodiment, the methods comprise a compound of formula 49 and the attendant definitions wherein n is 1.

In a further embodiment, the methods comprise a compound of formula 49 and the attendant definitions wherein R is methyl.

In a further embodiment, the methods comprise a compound of formula 49 and the attendant definitions wherein $R_1$ is $C(O)OCH_3$.

In a further embodiment, the methods comprise a compound of formula 49 and the attendant definitions wherein $R_2$ is $C(O)OCH_3$.

In a further embodiment, the methods comprise a compound of formula 49 and the attendant definitions wherein $R_3$ is methyl.

In a further embodiment, the methods comprise a compound of formula 49 and the attendant definitions wherein $R_4$ is methyl.

In a further embodiment, the methods comprise a compound of formula 49 and the attendant definitions wherein $R_5$ is $CH_2CH(CH_3)_2$.

In a further embodiment, the methods comprise a compound of formula 49 and the attendant definitions wherein $L_1$ is S.

In a further embodiment, the methods comprise a compound of formula 49 and the attendant definitions wherein $L_2$ is S.

In a further embodiment, the methods comprise a compound of formula 49 and the attendant definitions wherein $L_3$ is S.

In a further embodiment, the methods comprise a compound of formula 49 and the attendant definitions wherein n is 1 and R is methyl.

In a further embodiment, the methods comprise a compound of formula 49 and the attendant definitions wherein n is 1, R is methyl, and $R_1$ is $C(O)OCH_3$.

In a further embodiment, the methods comprise a compound of formula 49 and the attendant definitions wherein n is 1, R is methyl, $R_1$ is $C(O)OCH_3$, and $R_2$ is $C(O)OCH_3$.

In a further embodiment, the methods comprise a compound of formula 49 and the attendant definitions wherein n is 1, R is methyl, $R_1$ is $C(O)OCH_3$, $R_2$ is $C(O)OCH_3$, and $R_3$ is methyl.

In a further embodiment, the methods comprise a compound of formula 49 and the attendant definitions wherein n is 1, R is methyl, $R_1$ is $C(O)OCH_3$, $R_2$ is $C(O)OCH_3$, $R_3$ is methyl, and $R_4$ is methyl.

In a further embodiment, the methods comprise a compound of formula 49 and the attendant definitions wherein n is 1, R is methyl, $R_1$ is $C(O)OCH_3$, $R_2$ is $C(O)OCH_3$, $R_3$ is methyl, $R_4$ is methyl, and $R_5$ is $CH_2CH(CH_3)_2$.

In a further embodiment, the methods comprise a compound of formula 49 and the attendant definitions wherein n is 1, R is methyl, $R_1$ is $C(O)OCH_3$, $R_2$ is $C(O)OCH_3$, $R_3$ is methyl, $R_4$ is methyl, $R_5$ is $CH_2CH(CH_3)_2$, and $L_1$ is S.

In a further embodiment, the methods comprise a compound of formula 49 and the attendant definitions wherein n is 1, R is methyl, $R_1$ is C(O)OCH$_3$, $R_2$ is C(O)OCH$_3$, $R_3$ is methyl, $R_4$ is methyl, $R_5$ is CH$_2$CH(CH$_3$)$_2$, and $L_1$ is S.

In a further embodiment, the methods comprise a compound of formula 49 and the attendant definitions wherein n is 1, R is methyl, $R_1$ is C(O)OCH$_3$, $R_2$ is C(O)OCH$_3$, $R_3$ is methyl, $R_4$ is methyl, $R_5$ is CH$_2$CH(CH$_3$)$_2$, $L_1$ is S, and $L_2$ is S.

In a further embodiment, the methods comprise a compound of formula 49 and the attendant definitions wherein n is 1, R is methyl, $R_1$ is C(O)OCH$_3$, $R_2$ is C(O)OCH$_3$, $R_3$ is methyl, $R_4$ is methyl, $R_5$ is CH$_2$CH(CH$_3$)$_2$, $L_1$ is S, and $L_2$ is S.

In a further embodiment, the methods comprise a compound of formula 49 and the attendant definitions wherein n is 1, R is methyl, $R_1$ is C(O)OCH$_3$, $R_2$ is C(O)OCH$_3$, $R_3$ is methyl, $R_4$ is methyl, $R_5$ is CH$_2$CH(CH$_3$)$_2$, $L_1$ is S, $L_2$ is S, and $L_3$ is S.

In another embodiment, methods for activating a sirtuin protein comprise using an activating compound of formula 50:

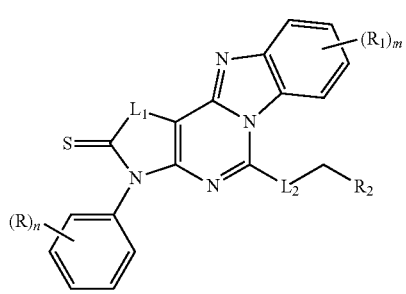

wherein, independently for each occurrence:

R and $R_1$ are hydroxy, amino, cyano, halide, OR$_4$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_2$ is H, hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_4$ is alkyl, —SO$_3$H, monosaccharide, oligosaccharide, glycofuranosyl, glycopyranosyl, glucuronosyl, or glucuronide;

$L_1$ and $L_2$ are O, NR$_3$, or S;

$R_3$ is H or a substituted or unsubstituted alkyl, aryl, aralkyl, heterocyclyl, heterocyclylalkyl, heteroaryl, or heteroaralkyl;

n is an integer from 0 to 5 inclusive; and m is an integer from 0 to 4 inclusive.

In a further embodiment, the methods comprise a compound of formula 50 and the attendant definitions wherein n is 1.

In a further embodiment, the methods comprise a compound of formula 50 and the attendant definitions wherein R is CO$_2$Et.

In a further embodiment, the methods comprise a compound of formula 50 and the attendant definitions wherein m is 0.

In a further embodiment, the methods comprise a compound of formula 50 and the attendant definitions wherein $R_2$ is cyano.

In a further embodiment, the methods comprise a compound of formula 50 and the attendant definitions wherein $L_1$ is S.

In a further embodiment, the methods comprise a compound of formula 50 and the attendant definitions wherein $L_2$ is S.

In a further embodiment, the methods comprise a compound of formula 50 and the attendant definitions wherein n is 1 and R is CO$_2$Et.

In a further embodiment, the methods comprise a compound of formula 50 and the attendant definitions wherein n is 1, R is CO$_2$Et, and m is 0.

In a further embodiment, the methods comprise a compound of formula 50 and the attendant definitions wherein n is 1, R is CO$_2$Et, m is 0, and $R_2$ is cyano.

In a further embodiment, the methods comprise a compound of formula 50 and the attendant definitions wherein n is 1, R is CO$_2$Et, m is 0, $R_2$ is cyano, and $L_1$ is S.

In a further embodiment, the methods comprise a compound of formula 50 and the attendant definitions wherein n is 1, R is CO$_2$Et, m is 0, $R_2$ is cyano, $L_1$ is S, and $L_2$ is S.

In another embodiment, methods for activating a sirtuin protein comprise using an activating compound of formula 51:

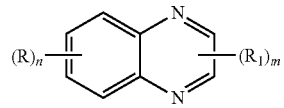

wherein, independently for each occurrence:

R and $R_1$ are hydroxy, amino, cyano, halide, OR$_2$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_2$ is alkyl, —SO$_3$H, monosaccharide, oligosaccharide, glycofuranosyl, glycopyranosyl, glucuronosyl, or glucuronide;

n is an integer from 0 to 4 inclusive; and m is an integer from 0 to 2 inclusive.

In a further embodiment, the methods comprise a compound of formula 51 and the attendant definitions wherein n is 2.

In a further embodiment, the methods comprise a compound of formula 51 and the attendant definitions wherein R is Cl or trifluoromethyl.

In a further embodiment, the methods comprise a compound of formula 51 and the attendant definitions wherein m is 2.

In a further embodiment, the methods comprise a compound of formula 51 and the attendant definitions wherein $R_1$ is phenyl.

In a further embodiment, the methods comprise a compound of formula 51 and the attendant definitions wherein n is 2 and R is Cl or trifluoromethyl.

In a further embodiment, the methods comprise a compound of formula 51 and the attendant definitions wherein n is 2, R is Cl or trifluoromethyl, and m is 2.

In a further embodiment, the methods comprise a compound of formula 51 and the attendant definitions wherein n is 2, R is Cl or trifluoromethyl, m is 2, and $R_1$ is phenyl.

In a further embodiment, the methods comprise a compound of formula 51 and the attendant definitions wherein n is 1.

In a further embodiment, the methods comprise a compound of formula 51 and the attendant definitions wherein R is F.

In a further embodiment, the methods comprise a compound of formula 51 and the attendant definitions wherein $R_1$ is 4-methylphenyl.

In a further embodiment, the methods comprise a compound of formula 51 and the attendant definitions wherein n is 1 and R is F.

In a further embodiment, the methods comprise a compound of formula 51 and the attendant definitions wherein n is 1, R is F, and m is 2.

In a further embodiment, the methods comprise a compound of formula 51 and the attendant definitions wherein n is 1, R is F, m is 2, and $R_1$ is 4-methylphenyl.

In another embodiment, methods for activating a sirtuin protein comprise using an activating compound of formula 52:

52 wherein, independently for each occurrence:

R is H or a substituted or unsubstituted alkyl, aryl, aralkyl, heterocyclyl, heterocyclylalkyl, heteroaryl, or heteroaralkyl;

$R_1$ and $R_6$ are hydroxy, amino, cyano, halide, $OR_7$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_2$ is alkylene, alkenylene, or alkynylene;

$R_3$, $R_4$, and $R_5$ are H, hydroxy, amino, cyano, halide, $OR_7$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_7$ is alkyl, —$SO_3H$, monosaccharide, oligosaccharide, glycofuranosyl, glycopyranosyl, glucuronosyl, or glucuronide;

$L_1$, $L_2$, and $L_3$ are O, NR, or S;

n and p are integers from 0 to 3 inclusive; and m and o are integers from 0 to 2 inclusive.

In a further embodiment, the methods comprise a compound of formula 52 and the attendant definitions wherein R is $CH_2CH_2OH$.

In a further embodiment, the methods comprise a compound of formula 52 and the attendant definitions wherein n is 1.

In a further embodiment, the methods comprise a compound of formula 52 and the attendant definitions wherein $R_1$ is I.

In a further embodiment, the methods comprise a compound of formula 52 and the attendant definitions wherein $R_2$ is alkynylene.

In a further embodiment, the methods comprise a compound of formula 52 and the attendant definitions wherein m is 1.

In a further embodiment, the methods comprise a compound of formula 52 and the attendant definitions wherein $R_3$ is OH.

In a further embodiment, the methods comprise a compound of formula 52 and the attendant definitions wherein $R_4$ is C(O)OEt.

In a further embodiment, the methods comprise a compound of formula 52 and the attendant definitions wherein o is 1.

In a further embodiment, the methods comprise a compound of formula 52 and the attendant definitions wherein $R_5$ is OH.

In a further embodiment, the methods comprise a compound of formula 52 and the attendant definitions wherein p is 0.

In a further embodiment, the methods comprise a compound of formula 52 and the attendant definitions wherein $L_1$ is NH.

In a further embodiment, the methods comprise a compound of formula 52 and the attendant definitions wherein $L_2$ is O.

In a further embodiment, the methods comprise a compound of formula 52 and the attendant definitions wherein $L_3$ is O.

In a further embodiment, the methods comprise a compound of formula 52 and the attendant definitions wherein R is $CH_2CH_2OH$ and n is 1.

In a further embodiment, the methods comprise a compound of formula 52 and the attendant definitions wherein R is $CH_2CH_2OH$, n is 1, and $R_1$ is I.

In a further embodiment, the methods comprise a compound of formula 52 and the attendant definitions wherein R is $CH_2CH_2OH$, n is 1, $R_1$ is I, and $R_2$ is alkynylene.

In a further embodiment, the methods comprise a compound of formula 52 and the attendant definitions wherein R is $CH_2CH_2OH$, n is 1, $R_1$ is I, $R_2$ is alkynylene, and m is 1.

In a further embodiment, the methods comprise a compound of formula 52 and the attendant definitions wherein R is $CH_2CH_2OH$, n is 1, $R_1$ is I, $R_2$ is alkynylene, m is 1, and $R_3$ is OH.

In a further embodiment, the methods comprise a compound of formula 52 and the attendant definitions wherein R is $CH_2CH_2OH$, n is 1, $R_1$ is I, $R_2$ is alkynylene, m is 1, $R_3$ is OH, and $R_4$ is C(O)OEt.

In a further embodiment, the methods comprise a compound of formula 52 and the attendant definitions wherein R is $CH_2CH_2OH$, n is 1, $R_1$ is I, $R_2$ is alkynylene, m is 1, $R_3$ is OH, $R_4$ is C(O)OEt, and o is 1.

In a further embodiment, the methods comprise a compound of formula 52 and the attendant definitions wherein R is $CH_2CH_2OH$, n is 1, $R_1$ is I, $R_2$ is alkynylene, m is 1, $R_3$ is OH, $R_4$ is C(O)OEt, o is 1, and $R_5$ is OH.

In a further embodiment, the methods comprise a compound of formula 52 and the attendant definitions wherein R is $CH_2CH_2OH$, n is 1, $R_1$ is I, $R_2$ is alkynylene, m is 1, $R_3$ is OH, $R_4$ is C(O)OEt, o is 1, $R_5$ is OH, and p is 0.

In a further embodiment, the methods comprise a compound of formula 52 and the attendant definitions wherein R is $CH_2CH_2OH$, n is 1, $R_1$ is I, $R_2$ is alkynylene, m is 1, $R_3$ is OH, $R_4$ is C(O)OEt, o is 1, $R_5$ is OH, p is 0, and $L_1$ is NH.

In a further embodiment, the methods comprise a compound of formula 52 and the attendant definitions wherein R is $CH_2CH_2OH$, n is 1, $R_1$ is I, $R_2$ is alkynylene, m is 1, $R_3$ is OH, $R_4$ is C(O)OEt, o is 1, $R_5$ is OH, p is 0, $L_1$ is NH, and $L_2$ is O.

In a further embodiment, the methods comprise a compound of formula 52 and the attendant definitions wherein R is CH$_2$CH$_2$OH, n is 1, R$_1$ is I, R$_2$ is alkynylene, m is 1, R$_3$ is OH, R$_4$ is C(O)OEt, o is 1, R$_5$ is OH, p is 0, L$_1$ is NH, L$_2$ is O, and L$_3$ is O.

In another embodiment, methods for activating a sirtuin protein comprise using an activating compound of formula 53:

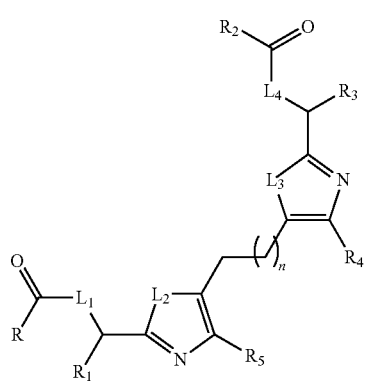

wherein, independently for each occurrence:

R, R$_1$, R$_2$, R$_3$, R$_4$, and R$_5$ are H, hydroxy, amino, cyano, halide, OR$_7$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

L$_1$, L$_2$, L$_3$, and L$_4$ are O, NR$_6$, or S;

R$_6$ is and H, or a substituted or unsubstituted alkyl, aryl, aralkyl, heterocyclyl, heterocyclylalkyl, heteroaryl, or heteroaralkyl;

R$_7$ is alkyl, —SO$_3$H, monosaccharide, oligosaccharide, glycofuranosyl, glycopyranosyl, glucuronosyl, or glucuronide; and n is an integer from 0 to 5 inclusive.

In a further embodiment, the methods comprise a compound of formula 53 and the attendant definitions wherein R is O-t-butyl.

In a further embodiment, the methods comprise a compound of formula 53 and the attendant definitions wherein R$_1$ is t-butyl.

In a further embodiment, the methods comprise a compound of formula 53 and the attendant definitions wherein R$_2$ is O-t-butyl.

In a further embodiment, the methods comprise a compound of formula 53 and the attendant definitions wherein R$_3$ is t-butyl.

In a further embodiment, the methods comprise a compound of formula 53 and the attendant definitions wherein R$_4$ is C(O)OMe.

In a further embodiment, the methods comprise a compound of formula 53 and the attendant definitions wherein R$_5$ is C(O)OMe.

In a further embodiment, the methods comprise a compound of formula 53 and the attendant definitions wherein L$_1$ is NH.

In a further embodiment, the methods comprise a compound of formula 53 and the attendant definitions wherein L$_2$ is O.

In a further embodiment, the methods comprise a compound of formula 53 and the attendant definitions wherein L$_3$ is O.

In a further embodiment, the methods comprise a compound of formula 53 and the attendant definitions wherein L$_4$ is NH.

In a further embodiment, the methods comprise a compound of formula 53 and the attendant definitions wherein n is 1.

In a further embodiment, the methods comprise a compound of formula 53 and the attendant definitions wherein R is O-t-butyl and R$_1$ is t-butyl.

In a further embodiment, the methods comprise a compound of formula 53 and the attendant definitions wherein R is O-t-butyl, R$_1$ is t-butyl, and R$_2$ is O-t-butyl.

In a further embodiment, the methods comprise a compound of formula 53 and the attendant definitions wherein R is O-t-butyl, R$_1$ is t-butyl, R$_2$ is O-t-butyl, and R$_3$ is t-butyl.

In a further embodiment, the methods comprise a compound of formula 53 and the attendant definitions wherein R is O-t-butyl, R$_1$ is t-butyl, R$_2$ is O-t-butyl, R$_3$ is t-butyl, and R$_4$ is C(O)OMe.

In a further embodiment, the methods comprise a compound of formula 53 and the attendant definitions wherein R is O-t-butyl, R$_1$ is t-butyl, R$_2$ is O-t-butyl, R$_3$ is t-butyl, R$_4$ is C(O)OMe, and R$_5$ is C(O)OMe.

In a further embodiment, the methods comprise a compound of formula 53 and the attendant definitions wherein R is O-t-butyl, R$_1$ is t-butyl, R$_2$ is O-t-butyl, R$_3$ is t-butyl, R$_4$ is C(O)OMe, R$_5$ is C(O)OMe, and L$_1$ is NH.

In a further embodiment, the methods comprise a compound of formula 53 and the attendant definitions wherein R is O-t-butyl, R$_1$ is t-butyl, R$_2$ is O-t-butyl, R$_3$ is t-butyl, R$_4$ is C(O)OMe, R$_5$ is C(O)OMe, L$_1$ is NH, and L$_2$ is O.

In a further embodiment, the methods comprise a compound of formula 53 and the attendant definitions wherein R is O-t-butyl, R$_1$ is t-butyl, R$_2$ is O-t-butyl, R$_3$ is t-butyl, R$_4$ is C(O)OMe, R$_5$ is C(O)OMe, L$_1$ is NH, L$_2$ is O, and L$_3$ is O.

In a further embodiment, the methods comprise a compound of formula 53 and the attendant definitions wherein R is O-t-butyl, R$_1$ is t-butyl, R$_2$ is O-t-butyl, R$_3$ is t-butyl, R$_4$ is C(O)OMe, R$_5$ is C(O)OMe, L$_1$ is NH, L$_2$ is O, L$_3$ is O, and L$_4$ is NH.

In a further embodiment, the methods comprise a compound of formula 53 and the attendant definitions wherein R is O-t-butyl, R$_1$ is t-butyl, R$_2$ is O-t-butyl, R$_3$ is t-butyl, R$_4$ is C(O)OMe, R$_5$ is C(O)OMe, L$_1$ is NH, L$_2$ is O, L$_3$ is O, L$_4$ is NH, and n is 1.

In another embodiment, methods for activating a sirtuin protein comprise using an activating compound of formula 54:

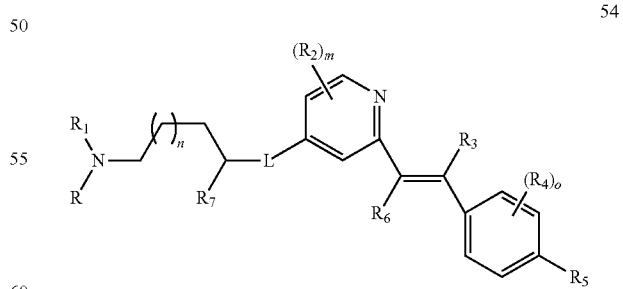

wherein, independently for each occurrence:

R and R$_1$ are H or a substituted or unsubstituted alkyl, aryl, aralkyl, heterocyclyl, heterocyclylalkyl, heteroaryl, or heteroaralkyl;

R$_2$, R$_4$, and R$_5$ are hydroxy, amino, cyano, halide, OR$_8$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_3$, $R_6$, and $R_7$ are H, hydroxy, amino, cyano, halide, $OR_8$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_8$ is alkyl, —$SO_3H$, monosaccharide, oligosaccharide, glycofuranosyl, glycopyranosyl, glucuronosyl, or glucuronide;

L is O, NR, or S;

n and o are integers from 0 to 4 inclusive; and m is an integer from 0 to 3 inclusive.

In a further embodiment, the methods comprise a compound of formula 54 and the attendant definitions wherein R is ethyl.

In a further embodiment, the methods comprise a compound of formula 54 and the attendant definitions wherein $R_1$ is ethyl.

In a further embodiment, the methods comprise a compound of formula 54 and the attendant definitions wherein m is 0.

In a further embodiment, the methods comprise a compound of formula 54 and the attendant definitions wherein $R_3$ is H.

In a further embodiment, the methods comprise a compound of formula 54 and the attendant definitions wherein o is 0.

In a further embodiment, the methods comprise a compound of formula 54 and the attendant definitions wherein $R_5$ is Cl.

In a further embodiment, the methods comprise a compound of formula 54 and the attendant definitions wherein $R_6$ is H.

In a further embodiment, the methods comprise a compound of formula 54 and the attendant definitions wherein $R_7$ is methyl.

In a further embodiment, the methods comprise a compound of formula 54 and the attendant definitions wherein L is NH.

In a further embodiment, the methods comprise a compound of formula 54 and the attendant definitions wherein n is 1.

In a further embodiment, the methods comprise a compound of formula 54 and the attendant definitions wherein R is ethyl and $R_1$ is ethyl.

In a further embodiment, the methods comprise a compound of formula 54 and the attendant definitions wherein R is ethyl, $R_1$ is ethyl, and m is 0.

In a further embodiment, the methods comprise a compound of formula 54 and the attendant definitions wherein R is ethyl, $R_1$ is ethyl, m is 0, and $R_3$ is H.

In a further embodiment, the methods comprise a compound of formula 54 and the attendant definitions wherein R is ethyl, $R_1$ is ethyl, m is 0, $R_3$ is H, and o is 0.

In a further embodiment, the methods comprise a compound of formula 54 and the attendant definitions wherein R is ethyl, $R_1$ is ethyl, m is 0, $R_3$ is H, o is 0, and $R_5$ is Cl.

In a further embodiment, the methods comprise a compound of formula 54 and the attendant definitions wherein R is ethyl, $R_1$ is ethyl, m is 0, $R_3$ is H, o is 0, $R_5$ is Cl, and $R_6$ is H.

In a further embodiment, the methods comprise a compound of formula 54 and the attendant definitions wherein R is ethyl, $R_1$ is ethyl, m is 0, $R_3$ is H, o is 0, $R_5$ is Cl, $R_6$ is H, and $R_7$ is methyl.

In a further embodiment, the methods comprise a compound of formula 54 and the attendant definitions wherein R is ethyl, $R_1$ is ethyl, m is 0, $R_3$ is H, o is 0, $R_5$ is Cl, $R_6$ is H, $R_7$ is methyl, and L is NH.

In a further embodiment, the methods comprise a compound of formula 54 and the attendant definitions wherein R is ethyl, $R_1$ is ethyl, m is 0, $R_3$ is H, o is 0, $R_5$ is Cl, $R_6$ is H, $R_7$ is methyl, L is NH, and n is 1.

In another embodiment, methods for activating a sirtuin protein comprise using an activating compound of formula 55:

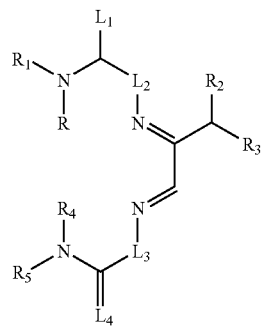

55 wherein, independently for each occurrence:

R, $R_1$, $R_4$, and $R_5$ are H or a substituted or unsubstituted alkyl, aryl, aralkyl, heterocyclyl, heterocyclylalkyl, heteroaryl, or heteroaralkyl;

$R_2$ and $R_3$ are H, hydroxy, amino, cyano, halide, $OR_6$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_6$ is alkyl, —$SO_3H$, monosaccharide, oligosaccharide, glycofuranosyl, glycopyranosyl, glucuronosyl, or glucuronide; and $L_1$, $L_2$, $L_3$, and $L_4$ are O, NR, or S.

In a further embodiment, the methods comprise a compound of formula 55 and the attendant definitions wherein R is H.

In a further embodiment, the methods comprise a compound of formula 55 and the attendant definitions wherein $R_1$ is H.

In a further embodiment, the methods comprise a compound of formula 55 and the attendant definitions wherein $R_2$ is OEt.

In a further embodiment, the methods comprise a compound of formula 55 and the attendant definitions wherein $R_3$ is methyl.

In a further embodiment, the methods comprise a compound of formula 55 and the attendant definitions wherein $R_4$ is H.

In a further embodiment, the methods comprise a compound of formula 55 and the attendant definitions wherein $R_5$ is H.

In a further embodiment, the methods comprise a compound of formula 55 and the attendant definitions wherein $L_1$ is S.

In a further embodiment, the methods comprise a compound of formula 55 and the attendant definitions wherein $L_2$ is NH.

In a further embodiment, the methods comprise a compound of formula 55 and the attendant definitions wherein $L_3$ is NH.

In a further embodiment, the methods comprise a compound of formula 55 and the attendant definitions wherein $L_4$ is S.

In a further embodiment, the methods comprise a compound of formula 55 and the attendant definitions wherein R is H and $R_1$ is H.

In a further embodiment, the methods comprise a compound of formula 55 and the attendant definitions wherein R is H, $R_1$ is H, and $R_2$ is OEt.

In a further embodiment, the methods comprise a compound of formula 55 and the attendant definitions wherein R is H, $R_1$ is H, $R_2$ is OEt, and $R_3$ is methyl.

In a further embodiment, the methods comprise a compound of formula 55 and the attendant definitions wherein R is H, $R_1$ is H, $R_2$ is OEt, $R_3$ is methyl, and $R_4$ is H.

In a further embodiment, the methods comprise a compound of formula 55 and the attendant definitions wherein R is H, $R_1$ is H, $R_2$ is OEt, $R_3$ is methyl, $R_4$ is H, and $R_5$ is H.

In a further embodiment, the methods comprise a compound of formula 55 and the attendant definitions wherein R is H, $R_1$ is H, $R_2$ is OEt, $R_3$ is methyl, $R_4$ is H, $R_5$ is H, and $L_1$ is S.

In a further embodiment, the methods comprise a compound of formula 55 and the attendant definitions wherein R is H, $R_1$ is H, $R_2$ is OEt, $R_3$ is methyl, $R_4$ is H, $R_5$ is H, $L_1$ is S, and $L_2$ is NH.

In a further embodiment, the methods comprise a compound of formula 55 and the attendant definitions wherein R is H, $R_1$ is H, $R_2$ is OEt, $R_3$ is methyl, $R_4$ is H, $R_5$ is H, $L_1$ is S, $L_2$ is NH, and $L_3$ is NH.

In a further embodiment, the methods comprise a compound of formula 55 and the attendant definitions wherein R is H, $R_1$ is H, $R_2$ is OEt, $R_3$ is methyl, $R_4$ is H, $R_5$ is H, $L_1$ is S, $L_2$ is NH, $L_3$ is NH, and $L_4$ is S.

In another embodiment, methods for activating a sirtuin protein comprise using an activating compound of formula 56:

wherein, independently for each occurrence:

R and $R_1$ are hydroxy, amino, cyano, halide, $OR_3$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_3$ is alkyl, $-SO_3H$, monosaccharide, oligosaccharide, glycofuranosyl, glycopyranosyl, glucuronosyl, or glucuronide;

$L_1$, $L_2$, and $L_3$ are O, $NR_2$, or S;

$R_2$ is H or a substituted or unsubstituted alkyl, aryl, aralkyl, heterocyclyl, heterocyclylalkyl, heteroaryl, or heteroaralkyl;

n is an integer from 0 to 4 inclusive; and m is an integer from 0 to 5 inclusive.

In a further embodiment, the methods comprise a compound of formula 56 and the attendant definitions wherein n is 0.

In a further embodiment, the methods comprise a compound of formula 56 and the attendant definitions wherein m is 0.

In a further embodiment, the methods comprise a compound of formula 56 and the attendant definitions wherein $L_1$ is NH.

In a further embodiment, the methods comprise a compound of formula 56 and the attendant definitions wherein $L_2$ is S.

In a further embodiment, the methods comprise a compound of formula 56 and the attendant definitions wherein $L_3$ is S.

In a further embodiment, the methods comprise a compound of formula 56 and the attendant definitions wherein m is 0 and n is 0.

In a further embodiment, the methods comprise a compound of formula 56 and the attendant definitions wherein m is 0, n is 0, and $L_1$ is NH.

In a further embodiment, the methods comprise a compound of formula 56 and the attendant definitions wherein m is 0, n is 0, $L_1$ is NH, and $L_2$ is S.

In a further embodiment, the methods comprise a compound of formula 56 and the attendant definitions wherein m is 0, n is 0, $L_1$ is NH, $L_2$ is S, and $L_3$ is S.

In another embodiment, methods for activating a sirtuin protein comprise using an activating compound of formula 57:

wherein, independently for each occurrence:

R, $R_1$, $R_2$, and $R_3$ are hydroxy, amino, cyano, halide, $OR_4$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_3$ is alkyl, $-SO_3H$, monosaccharide, oligosaccharide, glycofuranosyl, glycopyranosyl, glucuronosyl, or glucuronide;

A is alkylene, alkenylene, or alkynylene;

n is an integer from 0 to 8 inclusive;

m is an integer from 0 to 3 inclusive;

o is an integer from 0 to 6 inclusive; and p is an integer from 0 to 4 inclusive.

In a further embodiment, the methods comprise a compound of formula 57 and the attendant definitions wherein n is 2.

In a further embodiment, the methods comprise a compound of formula 57 and the attendant definitions wherein R is OH or methyl.

In a further embodiment, the methods comprise a compound of formula 57 and the attendant definitions wherein m is 1.

In a further embodiment, the methods comprise a compound of formula 57 and the attendant definitions wherein $R_1$ is methyl.

In a further embodiment, the methods comprise a compound of formula 57 and the attendant definitions wherein o is 1.

In a further embodiment, the methods comprise a compound of formula 57 and the attendant definitions wherein $R_2$ is $C(O)CH_3$.

In a further embodiment, the methods comprise a compound of formula 57 and the attendant definitions wherein p is 2.

In a further embodiment, the methods comprise a compound of formula 57 and the attendant definitions wherein $R_3$ is $CO_2H$.

In a further embodiment, the methods comprise a compound of formula 57 and the attendant definitions wherein A is alkenylene.

In a further embodiment, the methods comprise a compound of formula 57 and the attendant definitions wherein n is 2 and R is OH or methyl.

In a further embodiment, the methods comprise a compound of formula 57 and the attendant definitions wherein n is 2, R is OH or methyl, and m is 1.

In a further embodiment, the methods comprise a compound of formula 57 and the attendant definitions wherein n is 2, R is OH or methyl, m is 1, and $R_1$ is methyl.

In a further embodiment, the methods comprise a compound of formula 57 and the attendant definitions wherein n is 2, R is OH or methyl, m is 1, $R_1$ is methyl, and o is 1.

In a further embodiment, the methods comprise a compound of formula 57 and the attendant definitions wherein n is 2, R is OH or methyl, m is 1, $R_1$ is methyl, o is 1, and $R_2$ is $C(O)CH_3$.

In a further embodiment, the methods comprise a compound of formula 57 and the attendant definitions wherein n is 2, R is OH or methyl, m is 1, $R_1$ is methyl, o is 1, $R_2$ is $C(O)CH_3$, and p is 2.

In a further embodiment, the methods comprise a compound of formula 57 and the attendant definitions wherein n is 2, R is OH or methyl, m is 1, $R_1$ is methyl, o is 1, $R_2$ is $C(O)CH_3$, p is 2, and $R_3$ is $CO_2H$.

In a further embodiment, the methods comprise a compound of formula 57 and the attendant definitions wherein n is 2, R is OH or methyl, m is 1, $R_1$ is methyl, o is 1, $R_2$ is $C(O)CH_3$, p is 2, $R_3$ is $CO_2H$, and A is alkenylene.

In another embodiment, methods for activating a sirtuin protein comprise using an activating compound of formula 58:

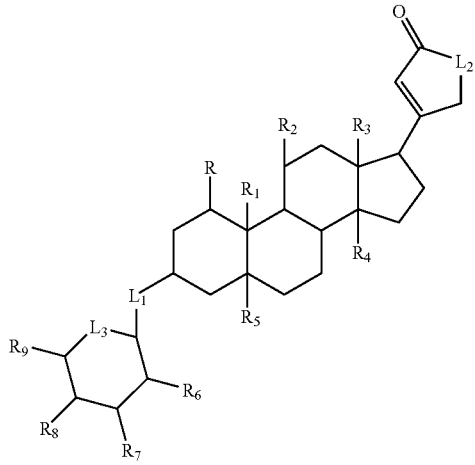

58 wherein, independently for each occurrence:

R, $R_1$, $R_2$, $R_3$, $R_4$, $R_5$, $R_6$, $R_7$, $R_8$, and $R_9$ are hydroxy, amino, cyano, halide, $OR'_1$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_{11}$ is alkyl, —$SO_3H$, monosaccharide, oligosaccharide, glycofuranosyl, glycopyranosyl, glucuronosyl, or glucuronide;

$L_1$, $L_2$, and $L_3$ are O, $NR_{10}$, or S; and $R_{10}$ is H or a substituted or unsubstituted alkyl, aryl, aralkyl, heterocyclyl, heterocyclylalkyl, heteroaryl, or heteroaralkyl.

In a further embodiment, the methods comprise a compound of formula 58 and the attendant definitions wherein R is OH.

In a further embodiment, the methods comprise a compound of formula 58 and the attendant definitions wherein $R_1$ is $CH_2OH$.

In a further embodiment, the methods comprise a compound of formula 58 and the attendant definitions wherein $R_2$ is OH.

In a further embodiment, the methods comprise a compound of formula 58 and the attendant definitions wherein $R_3$ is methyl.

In a further embodiment, the methods comprise a compound of formula 58 and the attendant definitions wherein $R_4$ is OH.

In a further embodiment, the methods comprise a compound of formula 58 and the attendant definitions wherein $R_5$ is OH.

In a further embodiment, the methods comprise a compound of formula 58 and the attendant definitions wherein $R_6$ is OH.

In a further embodiment, the methods comprise a compound of formula 58 and the attendant definitions wherein $R_7$ is OH.

In a further embodiment, the methods comprise a compound of formula 58 and the attendant definitions wherein $R_8$ is OH.

In a further embodiment, the methods comprise a compound of formula 58 and the attendant definitions wherein $R_9$ is methyl.

In a further embodiment, the methods comprise a compound of formula 58 and the attendant definitions wherein $L_1$ is O.

In a further embodiment, the methods comprise a compound of formula 58 and the attendant definitions wherein $L_2$ is O.

In a further embodiment, the methods comprise a compound of formula 58 and the attendant definitions wherein $L_3$ is O.

In a further embodiment, the methods comprise a compound of formula 58 and the attendant definitions wherein R is OH and $R_1$ is $CH_2OH$.

In a further embodiment, the methods comprise a compound of formula 58 and the attendant definitions wherein R is OH, $R_1$ is $CH_2OH$, and $R_2$ is OH.

In a further embodiment, the methods comprise a compound of formula 58 and the attendant definitions wherein R is OH, $R_1$ is $CH_2OH$, $R_2$ is OH, and $R_3$ is methyl.

In a further embodiment, the methods comprise a compound of formula 58 and the attendant definitions wherein R is OH, $R_1$ is $CH_2OH$, $R_2$ is OH, $R_3$ is methyl, and $R_4$ is OH.

In a further embodiment, the methods comprise a compound of formula 58 and the attendant definitions wherein R is OH, $R_1$ is $CH_2OH$, $R_2$ is OH, $R_3$ is methyl, $R_4$ is OH, and $R_5$ is OH.

In a further embodiment, the methods comprise a compound of formula 58 and the attendant definitions wherein R is OH, $R_1$ is $CH_2OH$, $R_2$ is OH, $R_3$ is methyl, $R_4$ is OH, $R_5$ is OH, and $R_6$ is OH.

In a further embodiment, the methods comprise a compound of formula 58 and the attendant definitions wherein R is OH, $R_1$ is $CH_2OH$, $R_2$ is OH, $R_3$ is methyl, $R_4$ is OH, $R_5$ is OH, $R_6$ is OH, and $R_7$ is OH.

In a further embodiment, the methods comprise a compound of formula 58 and the attendant definitions wherein R is OH, $R_1$ is $CH_2OH$, $R_2$ is OH, $R_3$ is methyl, $R_4$ is OH, $R_5$ is OH, $R_6$ is OH, $R_7$ is OH, and $R_8$ is OH.

In a further embodiment, the methods comprise a compound of formula 58 and the attendant definitions wherein R is OH, $R_1$ is $CH_2OH$, $R_2$ is OH, $R_3$ is methyl, $R_4$ is OH, $R_5$ is OH, $R_6$ is OH, $R_7$ is OH, $R_8$ is OH, and $R_9$ is methyl.

In a further embodiment, the methods comprise a compound of formula 58 and the attendant definitions wherein R is OH, $R_1$ is $CH_2OH$, $R_2$ is OH, $R_3$ is methyl, $R_4$ is OH, $R_5$ is OH, $R_6$ is OH, $R_7$ is OH, $R_8$ is OH, $R_9$ is methyl, and $L_1$ is O.

In a further embodiment, the methods comprise a compound of formula 58 and the attendant definitions wherein R is OH, $R_1$ is $CH_2OH$, $R_2$ is OH, $R_3$ is methyl, $R_4$ is OH, $R_5$ is OH, $R_6$ is OH, $R_7$ is OH, $R_8$ is OH, $R_9$ is methyl, $L_1$ is O, and $L_2$ is O.

In a further embodiment, the methods comprise a compound of formula 58 and the attendant definitions wherein R is OH, $R_1$ is $CH_2OH$, $R_2$ is OH, $R_3$ is methyl, $R_4$ is OH, $R_5$ is OH, $R_6$ is OH, $R_7$ is OH, $R_8$ is OH, $R_9$ is methyl, $L_1$ is O, $L_2$ is O, and $L_3$ is O.

In another embodiment, methods for activating a sirtuin protein comprise using an activating compound of formula 59:

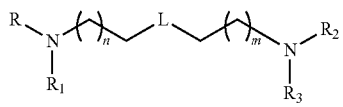

wherein, independently for each occurrence:

R, $R_1$, $R_2$, and $R_3$ are H or a substituted or unsubstituted alkyl, aryl, aralkyl, heterocyclyl, heterocyclylalkyl, heteroaryl, or heteroaralkyl;

L is O, NR, S, or Se; and n and m are integers from 0 to 5 inclusive.

In a further embodiment, the methods comprise a compound of formula 59 and the attendant definitions wherein R is H.

In a further embodiment, the methods comprise a compound of formula 59 and the attendant definitions wherein $R_1$ is H.

In a further embodiment, the methods comprise a compound of formula 59 and the attendant definitions wherein $R_2$ is H.

In a further embodiment, the methods comprise a compound of formula 59 and the attendant definitions wherein $R_3$ is H.

In a further embodiment, the methods comprise a compound of formula 59 and the attendant definitions wherein L is Se.

In a further embodiment, the methods comprise a compound of formula 59 and the attendant definitions wherein n is 1.

In a further embodiment, the methods comprise a compound of formula 59 and the attendant definitions wherein m is 1.

In a further embodiment, the methods comprise a compound of formula 59 and the attendant definitions wherein R is H and $R_1$ is H.

In a further embodiment, the methods comprise a compound of formula 59 and the attendant definitions wherein R is H, $R_1$ is H, and $R_2$ is H.

In a further embodiment, the methods comprise a compound of formula 59 and the attendant definitions wherein R is H, $R_1$ is H, $R_2$ is H, and $R_3$ is H.

In a further embodiment, the methods comprise a compound of formula 59 and the attendant definitions wherein R is H, $R_1$ is H, $R_2$ is H, $R_3$ is H, and L is Se.

In a further embodiment, the methods comprise a compound of formula 59 and the attendant definitions wherein R is H, $R_1$ is H, $R_2$ is H, $R_3$ is H, L is Se, and n is 1.

In a further embodiment, the methods comprise a compound of formula 59 and the attendant definitions wherein R is H, $R_1$ is H, $R_2$ is H, $R_3$ is H, L is Se, n is 1, and m is 1.

In another embodiment, methods for activating a sirtuin protein comprise using an activating compound of formula 60:

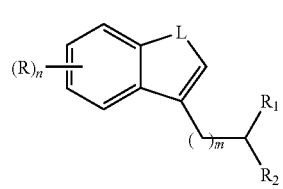

wherein, independently for each occurrence:

R is hydroxy, amino, cyano, halide, $OR_4$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_1$ and $R_2$ are H, hydroxy, amino, cyano, halide, $OR_4$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_4$ is alkyl, $-SO_3H$, monosaccharide, oligosaccharide, glycofuranosyl, glycopyranosyl, glucuronosyl, or glucuronide;

L is O, $NR_3$, S, or $SO_2$;

$R_3$ is H or a substituted or unsubstituted alkyl, aryl, aralkyl, heterocyclyl, heterocyclylalkyl, heteroaryl, or heteroaralkyl;

n is an integer from 0 to 4 inclusive; and m is an integer from 1 to 5 inclusive.

In a further embodiment, the methods comprise a compound of formula 60 and the attendant definitions wherein n is 1.

In a further embodiment, the methods comprise a compound of formula 60 and the attendant definitions wherein R is Cl.

In a further embodiment, the methods comprise a compound of formula 60 and the attendant definitions wherein $R_1$ is $NH_2$.

In a further embodiment, the methods comprise a compound of formula 60 and the attendant definitions wherein $R_2$ is $CO_2H$.

In a further embodiment, the methods comprise a compound of formula 60 and the attendant definitions wherein L is $SO_2$.

In a further embodiment, the methods comprise a compound of formula 60 and the attendant definitions wherein m is 1.

In a further embodiment, the methods comprise a compound of formula 60 and the attendant definitions wherein n is 1 and R is Cl.

In a further embodiment, the methods comprise a compound of formula 60 and the attendant definitions wherein n is 1, R is Cl, and $R_1$ is $NH_2$.

In a further embodiment, the methods comprise a compound of formula 60 and the attendant definitions wherein n is 1, R is Cl, $R_1$ is $NH_2$, and $R_2$ is $CO_2H$.

In a further embodiment, the methods comprise a compound of formula 60 and the attendant definitions wherein n is 1, R is Cl, $R_1$ is $NH_2$, $R_2$ is $CO_2H$, and L is $SO_2$.

In a further embodiment, the methods comprise a compound of formula 60 and the attendant definitions wherein n is 1, R is Cl, $R_1$ is $NH_2$, $R_2$ is $CO_2H$, L is $SO_2$, and m is 1.

In another embodiment, methods for activating a sirtuin protein comprise using an activating compound of formula 61:

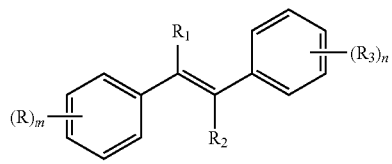

wherein, independently for each occurrence:

R, $R_1$, $R_2$, and $R_3$ are H, hydroxy, amino, cyano, halide, $OR_4$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_4$ is alkyl, —$SO_3H$, monosaccharide, oligosaccharide, glycofuranosyl, glycopyranosyl, glucuronosyl, or glucuronide; and n and m are integers from 0 to 5 inclusive.

In a further embodiment, the methods comprise a compound of formula 61 and the attendant definitions wherein n is 2.

In a further embodiment, the methods comprise a compound of formula 61 and the attendant definitions wherein R is 3-hydroxy and 5-hydroxy.

In a further embodiment, the methods comprise a compound of formula 61 and the attendant definitions wherein $R_1$ is H.

In a further embodiment, the methods comprise a compound of formula 61 and the attendant definitions wherein $R_2$ is H.

In a further embodiment, the methods comprise a compound of formula 61 and the attendant definitions wherein m is 0.

In a further embodiment, the methods comprise a compound of formula 61 and the attendant definitions wherein m is 1.

In a further embodiment, the methods comprise a compound of formula 61 and the attendant definitions wherein $R_3$ is 4-hydroxy.

In a further embodiment, the methods comprise a compound of formula 61 and the attendant definitions wherein $R_3$ is 4-methoxy.

In a further embodiment, the methods comprise a compound of formula 61 and the attendant definitions wherein n is 2 and R is 3-hydroxy and 5-hydroxy.

In a further embodiment, the methods comprise a compound of formula 61 and the attendant definitions wherein n is 2, R is 3-hydroxy and 5-hydroxy, and $R_1$ is H.

In a further embodiment, the methods comprise a compound of formula 61 and the attendant definitions wherein n is 2, R is 3-hydroxy and 5-hydroxy, $R_1$ is H, and $R_2$ is H.

In a further embodiment, the methods comprise a compound of formula 61 and the attendant definitions wherein n is 2, R is 3-hydroxy and 5-hydroxy, $R_1$ is H, $R_2$ is H, and m is 0.

In a further embodiment, the methods comprise a compound of formula 61 and the attendant definitions wherein n is 2, R is 3-hydroxy and 5-hydroxy, $R_1$ is H, $R_2$ is H, and m is 1.

In a further embodiment, the methods comprise a compound of formula 61 and the attendant definitions wherein n is 2, R is 3-hydroxy and 5-hydroxy, $R_1$ is H, $R_2$ is H, m is 1, and $R_3$ is 4-hydroxy.

In a further embodiment, the methods comprise a compound of formula 61 and the attendant definitions wherein n is 2, R is 3-hydroxy and 5-hydroxy, $R_1$ is H, $R_2$ is H, m is 1, and $R_3$ is 4-methoxy.

In another embodiment, methods for activating a sirtuin protein comprise using an activating compound of formula 62:

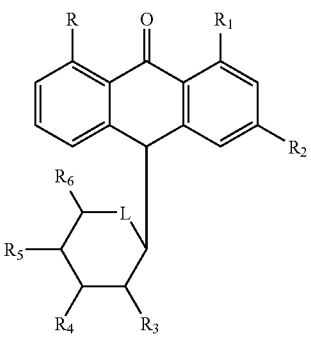

wherein, independently for each occurrence:

R, $R_1$, $R_2$, $R_3$, $R_4$, $R_5$, and $R_6$ are H, hydroxy, amino, cyano, $OR_8$, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

R8 is alkyl, —$SO_3H$, monosaccharide, oligosaccharide, glycofuranosyl, glycopyranosyl, glucuronosyl, or glucuronide;

L is O, $NR_7$, or S; and $R_7$ is H or a substituted or unsubstituted alkyl, aryl, aralkyl, heterocyclyl, heterocyclylalkyl, heteroaryl, or heteroaralkyl.

In a further embodiment, the methods comprise a compound of formula 62 and the attendant definitions wherein R is OH.

In a further embodiment, the methods comprise a compound of formula 62 and the attendant definitions wherein $R_1$ is OH.

In a further embodiment, the methods comprise a compound of formula 62 and the attendant definitions wherein $R_2$ is $CH_2OH$.

In a further embodiment, the methods comprise a compound of formula 62 and the attendant definitions wherein $R_3$ is OH.

In a further embodiment, the methods comprise a compound of formula 62 and the attendant definitions wherein $R_4$ is OH.

In a further embodiment, the methods comprise a compound of formula 62 and the attendant definitions wherein $R_5$ is OH.

In a further embodiment, the methods comprise a compound of formula 62 and the attendant definitions wherein $R_6$ is $CH_2OH$.

In a further embodiment, the methods comprise a compound of formula 62 and the attendant definitions wherein L is O.

In a further embodiment, the methods comprise a compound of formula 62 and the attendant definitions wherein R is OH and $R_1$ is OH.

In a further embodiment, the methods comprise a compound of formula 62 and the attendant definitions wherein R is OH, $R_1$ is OH, and $R_2$ is $CH_2OH$.

In a further embodiment, the methods comprise a compound of formula 62 and the attendant definitions wherein R is OH, $R_1$ is OH, $R_2$ is $CH_2OH$, and $R_3$ is OH.

In a further embodiment, the methods comprise a compound of formula 62 and the attendant definitions wherein R is OH, $R_1$ is OH, $R_2$ is $CH_2OH$, $R_3$ is OH, and $R_4$ is OH.

In a further embodiment, the methods comprise a compound of formula 62 and the attendant definitions wherein R is OH, $R_1$ is OH, $R_2$ is $CH_2OH$, $R_3$ is OH, $R_4$ is OH, and $R_5$ is OH.

In a further embodiment, the methods comprise a compound of formula 62 and the attendant definitions wherein R is OH, $R_1$ is OH, $R_2$ is $CH_2OH$, $R_3$ is OH, $R_4$ is OH, $R_5$ is OH, and $R_6$ is $CH_2OH$.

In a further embodiment, the methods comprise a compound of formula 62 and the attendant definitions wherein R is OH, $R_1$ is OH, $R_2$ is $CH_2OH$, $R_3$ is OH, $R_4$ is OH, $R_5$ is OH, $R_6$ is $CH_2OH$, and L is O.

In another embodiment, methods for activating a sirtuin protein comprise using an activating compound of formula 63:

wherein, independently for each occurrence:

R, $R_1$, and $R_2$ are H, hydroxy, amino, cyano, halide, $OR_3$, ether, ester, amido, ketone, carboxylic acid, nitro, or a substituted or unsubstituted alkyl, aryl, aralkyl, heterocyclyl, heterocyclylalkyl, heteroaryl, or heteroaralkyl; and $R_3$ is alkyl, —$SO_3H$, monosaccharide, oligosaccharide, glycofuranosyl, glycopyranosyl, glucuronosyl, or glucuronide.

In a further embodiment, the methods comprise a compound of formula 63 and the attendant definitions wherein R is $CO_2H$.

In a further embodiment, the methods comprise a compound of formula 63 and the attendant definitions wherein $R_1$ is ethyl.

In a further embodiment, the methods comprise a compound of formula 63 and the attendant definitions wherein $R_2$ is N-1-pyrrolidine.

In a further embodiment, the methods comprise a compound of formula 63 and the attendant definitions wherein R is $CO_2H$ and $R_1$ is ethyl.

In a further embodiment, the methods comprise a compound of formula 63 and the attendant definitions wherein R is $CO_2H$ and $R_2$ is N-1-pyrrolidine.

In a further embodiment, the methods comprise a compound of formula 63 and the attendant definitions wherein $R_1$ is ethyl and $R_2$ is N-1-pyrrolidine.

In a further embodiment, the methods comprise a compound of formula 63 and the attendant definitions wherein R is $CO_2H$, $R_1$ is ethyl, and $R_2$ is N-1-pyrrolidine.

In another embodiment, methods for activating a sirtuin protein comprise using an activating compound of formula 64:

wherein, independently for each occurrence:

R, $R_1$, $R_2$, $R_3$, $R_4$, $R_5$, $R_6$, and $R_7$ are H, hydroxy, amino, cyano, halide, $OR_9$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_9$ is alkyl, —$SO_3H$, monosaccharide, oligosaccharide, glycofuranosyl, glycopyranosyl, glucuronosyl, or glucuronide;

$L_1$, $L_2$, and $L_3$ are $CH_2$, O, $NR_8$, or S; and $R_8$ is H or a substituted or unsubstituted alkyl, aryl, aralkyl, heterocyclyl, heterocyclylalkyl, heteroaryl, or heteroaralkyl.

In a further embodiment, the methods comprise a compound of formula 64 and the attendant definitions wherein R is Cl.

In a further embodiment, the methods comprise a compound of formula 64 and the attendant definitions wherein R is H.

In a further embodiment, the methods comprise a compound of formula 64 and the attendant definitions wherein $R_1$ is OH.

In a further embodiment, the methods comprise a compound of formula 64 and the attendant definitions wherein $R_2$ is $N(Me)_2$.

In a further embodiment, the methods comprise a compound of formula 64 and the attendant definitions wherein $R_3$ is OH.

In a further embodiment, the methods comprise a compound of formula 64 and the attendant definitions wherein $R_4$ is $C(O)NH_2$.

In a further embodiment, the methods comprise a compound of formula 64 and the attendant definitions wherein $R_5$ is OH.

In a further embodiment, the methods comprise a compound of formula 64 and the attendant definitions wherein $R_6$ is OH.

In a further embodiment, the methods comprise a compound of formula 64 and the attendant definitions wherein $R_7$ is OH.

In a further embodiment, the methods comprise a compound of formula 64 and the attendant definitions wherein $L_1$ is $CH_2$.

In a further embodiment, the methods comprise a compound of formula 64 and the attendant definitions wherein $L_2$ is O.

In a further embodiment, the methods comprise a compound of formula 64 and the attendant definitions wherein $L_3$ is O.

In a further embodiment, the methods comprise a compound of formula 64 and the attendant definitions wherein R is Cl and $R_1$ is OH.

In a further embodiment, the methods comprise a compound of formula 64 and the attendant definitions wherein R is Cl, $R_1$ is OH, and $R_2$ is $N(Me)_2$.

In a further embodiment, the methods comprise a compound of formula 64 and the attendant definitions wherein R is Cl, $R_1$ is OH, $R_2$ is $N(Me)_2$, and $R_3$ is OH.

In a further embodiment, the methods comprise a compound of formula 64 and the attendant definitions wherein R is Cl, $R_1$ is OH, $R_2$ is $N(Me)_2$, $R_3$ is OH, and $R_4$ is $C(O)NH_2$.

In a further embodiment, the methods comprise a compound of formula 64 and the attendant definitions wherein R is Cl, $R_1$ is OH, $R_2$ is $N(Me)_2$, $R_3$ is OH, $R_4$ is $C(O)NH_2$, and $R_5$ is OH.

In a further embodiment, the methods comprise a compound of formula 64 and the attendant definitions wherein R is Cl, $R_1$ is OH, $R_2$ is $N(Me)_2$, $R_3$ is OH, $R_4$ is $C(O)NH_2$, $R_5$ is OH, and $R_6$ is OH.

In a further embodiment, the methods comprise a compound of formula 64 and the attendant definitions wherein R is Cl, $R_1$ is OH, $R_2$ is $N(Me)_2$, $R_3$ is OH, $R_4$ is $C(O)NH_2$, $R_5$ is OH, $R_6$ is OH, and $R_7$ is OH.

In a further embodiment, the methods comprise a compound of formula 64 and the attendant definitions wherein R is Cl, $R_1$ is OH, $R_2$ is $N(Me)_2$, $R_3$ is OH, $R_4$ is $C(O)NH_2$, $R_5$ is OH, $R_6$ is OH, $R_7$ is OH, and $L_1$ is $CH_2$.

In a further embodiment, the methods comprise a compound of formula 64 and the attendant definitions wherein R is Cl, $R_1$ is OH, $R_2$ is $N(Me)_2$, $R_3$ is OH, $R_4$ is $C(O)NH_2$, $R_5$ is OH, $R_6$ is OH, $R_7$ is OH, $L_1$ is $CH_2$, and $L_2$ is O.

In a further embodiment, the methods comprise a compound of formula 64 and the attendant definitions wherein R is Cl, $R_1$ is OH, $R_2$ is $N(Me)_2$, $R_3$ is OH, $R_4$ is $C(O)NH_2$, $R_5$ is OH, $R_6$ is OH, $R_7$ is OH, $L_1$ is $CH_2$, $L_2$ is O, and $L_3$ is O.

In a further embodiment, the methods comprise a compound of formula 64 and the attendant definitions wherein R is H and $R_1$ is OH.

In a further embodiment, the methods comprise a compound of formula 64 and the attendant definitions wherein R is H, $R_1$ is OH, and $R_2$ is $N(Me)_2$.

In a further embodiment, the methods comprise a compound of formula 64 and the attendant definitions wherein R is H, $R_1$ is OH, $R_2$ is $N(Me)_2$, and $R_3$ is OH.

In a further embodiment, the methods comprise a compound of formula 64 and the attendant definitions wherein R is H, $R_1$ is OH, $R_2$ is $N(Me)_2$, $R_3$ is OH, and $R_4$ is $C(O)NH_2$.

In a further embodiment, the methods comprise a compound of formula 64 and the attendant definitions wherein R is H, $R_1$ is OH, $R_2$ is $N(Me)_2$, $R_3$ is OH, $R_4$ is $C(O)NH_2$, and $R_5$ is OH.

In a further embodiment, the methods comprise a compound of formula 64 and the attendant definitions wherein R is H, $R_1$ is OH, $R_2$ is $N(Me)_2$, $R_3$ is OH, $R_4$ is $C(O)NH_2$, $R_5$ is OH, and $R_6$ is OH.

In a further embodiment, the methods comprise a compound of formula 64 and the attendant definitions wherein R is H, $R_1$ is OH, $R_2$ is $N(Me)_2$, $R_3$ is OH, $R_4$ is $C(O)NH_2$, $R_5$ is OH, $R_6$ is OH, and $R_7$ is OH.

In a further embodiment, the methods comprise a compound of formula 64 and the attendant definitions wherein R is H, $R_1$ is OH, $R_2$ is $N(Me)_2$, $R_3$ is OH, $R_4$ is $C(O)NH_2$, $R_5$ is OH, $R_6$ is OH, $R_7$ is OH, and $L_1$ is $CH_2$.

In a further embodiment, the methods comprise a compound of formula 64 and the attendant definitions wherein R is H, $R_1$ is OH, $R_2$ is $N(Me)_2$, $R_3$ is OH, $R_4$ is $C(O)NH_2$, $R_5$ is OH, $R_6$ is OH, $R_7$ is OH, $L_1$ is $CH_2$, and $L_2$ is O.

In a further embodiment, the methods comprise a compound of formula 64 and the attendant definitions wherein R is H, $R_1$ is OH, $R_2$ is $N(Me)_2$, $R_3$ is OH, $R_4$ is $C(O)NH_2$, $R_5$ is OH, $R_6$ is OH, $R_7$ is OH, $L_1$ is $CH_2$, $L_2$ is O, and $L_3$ is O.

In another embodiment, methods for activating a sirtuin protein comprise using an activating compound of formula 65:

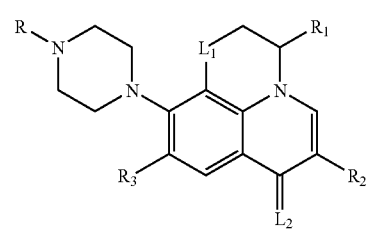

wherein, independently for each occurrence:

R is H or a substituted or unsubstituted alkyl, aryl, aralkyl, heterocyclyl, heterocyclylalkyl, heteroaryl, or heteroaralkyl;

$R_1$, $R_2$, and $R_3$ are hydroxy, amino, cyano, halide, $OR_4$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_4$ is alkyl, —$SO_3H$, monosaccharide, oligosaccharide, glycofuranosyl, glycopyranosyl, glucuronosyl, or glucuronide; and $L_1$ and $L_2$ are O, NR, or S.

In a further embodiment, the methods comprise a compound of formula 65 and the attendant definitions wherein R is methyl.

In a further embodiment, the methods comprise a compound of formula 65 and the attendant definitions wherein $R_1$ is methyl.

In a further embodiment, the methods comprise a compound of formula 65 and the attendant definitions wherein $R_2$ is $CO_2H$.

In a further embodiment, the methods comprise a compound of formula 65 and the attendant definitions wherein $R_3$ is F.

In a further embodiment, the methods comprise a compound of formula 65 and the attendant definitions wherein $L_1$ is O.

In a further embodiment, the methods comprise a compound of formula 65 and the attendant definitions wherein $L_2$ is O.

In a further embodiment, the methods comprise a compound of formula 65 and the attendant definitions wherein R is methyl and $R_1$ is methyl.

In a further embodiment, the methods comprise a compound of formula 65 and the attendant definitions wherein R is methyl, $R_1$ is methyl, and $R_2$ is $CO_2H$.

In a further embodiment, the methods comprise a compound of formula 65 and the attendant definitions wherein R is methyl, $R_1$ is methyl, $R_2$ is $CO_2H$, and $R_3$ is F.

In a further embodiment, the methods comprise a compound of formula 65 and the attendant definitions wherein R is methyl, $R_1$ is methyl, $R_2$ is $CO_2H$, $R_3$ is F, and $L_1$ is O.

In a further embodiment, the methods comprise a compound of formula 65 and the attendant definitions wherein R is methyl, $R_1$ is methyl, $R_2$ is $CO_2H$, $R_3$ is F, $L_1$ is O, and $L_2$ is O.

In another embodiment, exemplary sirtuin-activating compounds are isonicotinamide analogs, such as, for example, the isonicotinamide analogs described in U.S. Pat. Nos. 5,985,848; 6,066,722; 6,228,847; 6,492,347; 6,803,455; and U.S. Patent Publication Nos. 2001/0019823; 2002/0061898; 2002/0132783; 2003/0149261; 2003/0229033; 2003/0096830; 2004/053944; 2004/0110772; and 2004/0181063, the disclosures of which are hereby incorporated by reference in their entirety. In an exemplary embodiment, sirtuin-activating compounds may be an isonicotinamide analog having any of formulas 66-69 below. In one embodiment, a sirtuin-activating compound is an isonicotinamide analog compound of formula 66:

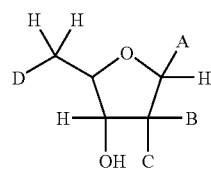

66

Wherein A is a nitrogen-, oxygen-, or sulfur-linked aryl, alkyl, cyclic, or heterocyclic group. The A moieties thus described, optionally have leaving group characteristics. In embodiments encompassed herein, A is further substituted with an electron contributing moiety. B and C are both hydrogen, or one of B or C is a halogen, amino, or thiol group and the other of B or C is hydrogen; and D is a primary alcohol, a hydrogen, or an oxygen, nitrogen, carbon, or sulfur linked to phosphate, a phosphoryl group, a pyrophosphoryl group, or adenosine monophosphate through a phosphodiester or carbon-, nitrogen-, or sulfur-substituted phosphodiester bridge, or to adenosine diphosphate through a phosphodiester or carbon-, nitrogen-, or sulfur-substituted pyrophosphodiester bridge.

In one example, A is a substituted N-linked aryl or heterocyclic group, an O-linked aryl or heterocyclic group having the formula —O—Y, or an S-linked aryl or heterocyclic group having the formula —O—Y; both B and C are hydrogen, or one of B or C is a halogen, amino, or thiol group and the other of B or C is hydrogen; and D is a primary alcohol or hydrogen. Nonlimiting preferred examples of A are set forth below, where each R is H or an electron-contributing moiety and Z is an alkyl, aryl, hydroxyl, OZ' where Z' is an alkyl or aryl, amino, NHZ' where Z' is an alkyl or aryl, or NHZ'Z" where Z' and Z" are independently an alkyl or aryl.

Examples of A include i-xiv below:

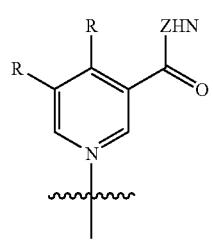

i

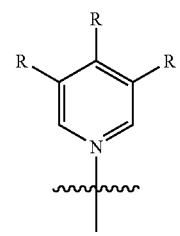

ii

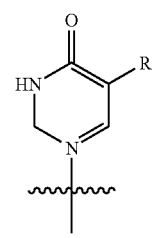

iii

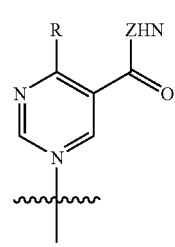

iv

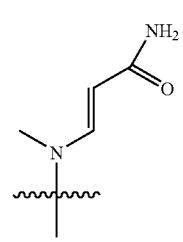

v

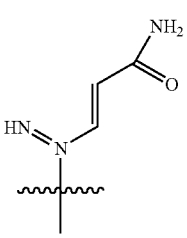

vi

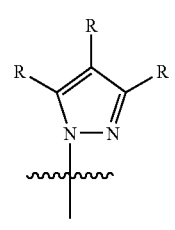

vii

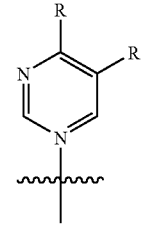

viii ix 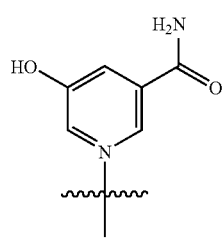
x 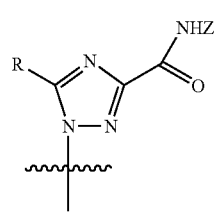
xi 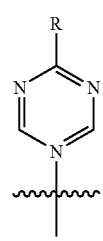
xii 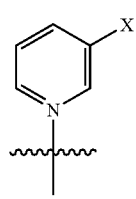
xiii 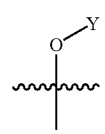
xiv 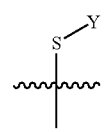
where Y=a group consistent with leaving group function.
Examples of Y include, but are not limited to, xv-xxvii below:
xv 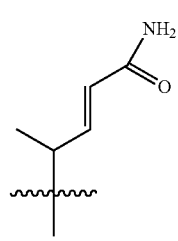
xvi 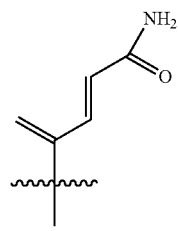
xvii 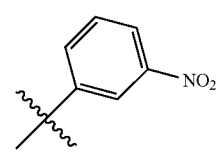
xviii 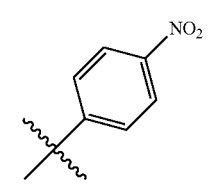
xix 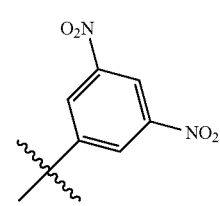
xx 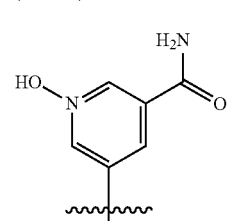
xxi 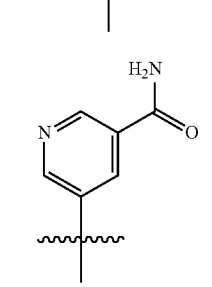
xxii 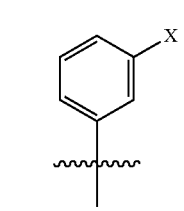
xxiii 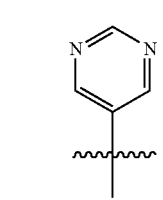

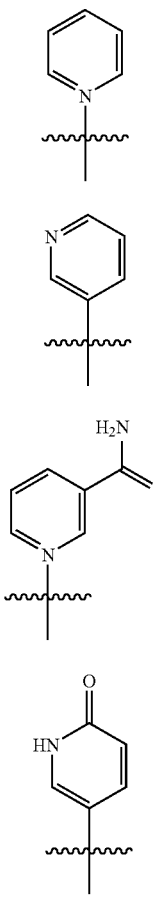

xxiv xxv xxvi xxvii

Wherein, for i-xxvii, X is halogen, thiol, or substituted thiol, amino or substituted amino, oxygen or substituted oxygen, or aryl or alkyl groups or heterocycles.

In certain embodiments, A is a substituted nicotinamide group (i above, where Z is H), a substituted pyrazolo group (vii above), or a substituted 3-carboxamid-imidazolo group (x above, where Z is H). Additionally, both B and C may be hydrogen, or one of B or C is a halogen, amino, or thiol group and the other of B or C is hydrogen; and D is a primary alcohol or hydrogen.

In other embodiments, one of B or C may be halogen, amino, or thiol group when the other of B or C is a hydrogen. Furthermore, D may be a hydrogen or an oxygen, nitrogen, carbon, or sulfur linked to phosphate, a phosphoryl group, a pyrophosphoryl group, or adenosine monophosphate through a phosphodiester or carbon-, nitrogen-, or sulfur-substituted phosphodiester bridge, or to adenosine diphosphate through a phosphodiester or carbon-, nitrogen-, or sulfur-substituted pyrophosphodiester bridge. Analogues of adenosine monophosphate or adenosine diphosphate also can replace the adenosine monophosphate or adenosine diphosphate groups.

In some embodiments, A has two or more electron contributing moieties.

In other embodiments, a sirtuin-activating compound is an isonicotinamide analog compound of formulas 67, 68, or 69 below.

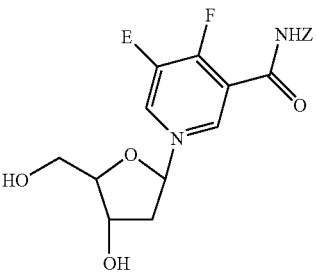

67 wherein Z is an alkyl, aryl, hydroxyl, OZ' where Z' is an alkyl or aryl, amino, NHZ' where Z' is an alkyl or aryl, or NHZ'Z" where Z' and Z" are independently an alkyl or aryl; E and F are independently H, $CH_3$, $OCH_3$, $CH_2CH_3$, $NH_2$, OH, NHCOH, $NHCOCH_3$, $N(CH_3)_2$, $C(CH_3)_2$, an aryl or a C3-C10 alkyl, preferably provided that, when one of E or F is H, the other of E or F is not H;

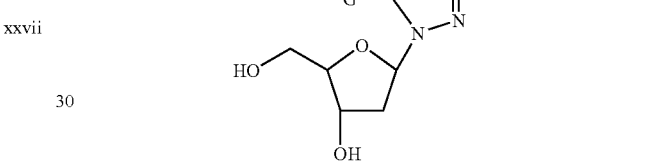

68 wherein G, J or K is CONHZ, Z is an alkyl, aryl, hydroxyl, OZ' where Z' is an alkyl or aryl, amino, NHZ' where Z' is an alkyl or aryl, or NHZ'Z" where Z' and Z" are independently an alkyl or aryl, and the other two of G, J and K is independently $CH_3$, $OCH_3$, $CH_2CH_3$, $NH_2$, OH, NHCOH, $NHCOCH_3$;

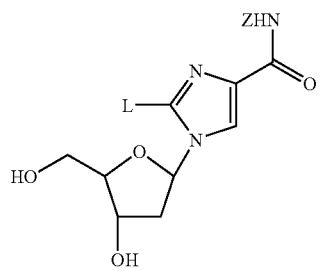

69 wherein Z is an alkyl, aryl, hydroxyl, OZ' where Z' is an alkyl or aryl, amino, NHZ' where Z' is an alkyl or aryl, or NHZ'Z" where Z' and Z" are independently an alkyl or aryl; and L is $CH_3$, $OCH_3$, $CH_2CH_3$, $NH_2$, OH, NHCOH, $NHCOCH_3$.

In an exemplary embodiment, the compound is formula 12 above, wherein E and F are independently H, $CH_3$, $OCH_3$, or OH, preferably provided that, when one of E or F is H, the other of E or F is not H.

In another exemplary embodiment, the compound is β-1'-5-methyl-nicotinamide-2'-deoxyribose, β-D-1'-5-methyl-nico-tinamide-2'-deoxyribofuranoside, β-1'-4,5-dimethyl-nicotinamide-2'-de-oxyribose or β-D-1'-4,5-dimethyl-nicotinamide-2'-deoxyribofuranoside.

In yet another embodiment, the compound is β-1'-5-methyl-nicotinamide-2'-deoxyribose.

Without being bound to any particular mechanism, it is believed that the electron-contributing moiety on A stabilizes the compounds of the invention such that they are less susceptible to hydrolysis from the rest of the compound. This improved chemical stability improves the value of the compound, since it is available for action for longer periods of time in biological systems due to resistance to hydrolytic breakdown. The skilled artisan could envision many electron-contributing moieties that would be expected to serve this stabilizing function. Nonlimiting examples of suitable electron contributing moieties are methyl, ethyl, O-methyl, amino, NMe2, hydroxyl, CMe3, aryl and alkyl groups. Preferably, the electron-contributing moiety is a methyl, ethyl, O-methyl, amino group. In the most preferred embodiments, the electron-contributing moiety is a methyl group.

The compounds of formulas 66-69 are useful both in free form and in the form of salts. The term "pharmaceutically acceptable salts" is intended to apply to non-toxic salts derived from inorganic or organic acids and includes, for example, salts derived from the following acids: hydrochloric, sulfuric, phosphoric, acetic, lactic, fumaric, succinic, tartaric, gluconic, citric, methanesulfonic, and p-toluenesulfonic acids.

Also provided are compounds of formulas 66-69 that are the tautomers, pharmaceutically-acceptable salts, esters, and pro-drugs of the inhibitor compounds disclosed herein.

The biological availability of the compounds of formulas 66-69 can be enhanced by conversion into a pro-drug form. Such a pro-drug can have improved lipophilicity relative to the unconverted compound, and this can result in enhanced membrane permeability. One particularly useful form of pro-drug is an ester derivative. Its utility relies upon the action of one or more of the ubiquitous intracellular lipases to catalyse the hydrolysis of ester groups, to release the active compound at or near its site of action. In one form of pro-drug, one or more hydroxy groups in the compound can be O-acylated, to make an acylate derivative.

Pro-drug forms of a 5-phosphate ester derivative of compounds of formulas 66-69 can also be made. These may be particularly useful, since the anionic nature of the 5-phosphate may limit its ability to cross cellular membranes. Conveniently, such a 5-phosphate derivative can be converted to an uncharged bis(acyloxymethyl) ester derivative. The utility of such a pro-drug relies upon the action of one or more of the ubiquitous intracellular lipases to catalyse the hydrolysis of ester groups, releasing a molecule of formaldehyde and a compound of the present invention at or near its site of action. Specific examples of the utility of, and general methods for making, such acyloxymethyl ester pro-drug forms of phosphorylated carbohydrate derivatives have been described (Kang et al., 1998; Jiang et al., 1998; Li et al., 1997; Kruppa et al., 1997).

In another embodiment, exemplary sirtuin-activating compounds are O-acetyl-ADP-ribose analogs, including 2'-O-acetyl-ADP-ribose and 3'-O-acetyl-ADP-ribose, and analogs thereof. Exemplary O-acetyl-ADP-ribose analogs are described, for example, in U.S. Patent Publication Nos. 2004/0053944; 2002/0061898; and 2003/0149261, the disclosures of which are hereby incorporated by reference in their entirety. In an exemplary embodiment, sirtuin-activating compounds may be an O-acetyl-ADP-ribose analog having any of formulas 70-73 below. In one embodiment, a sirtuin-activating compound is an O-acetyl-ADP-ribose analog compound of formula 70:

70 wherein:
A is selected from N, CH and CR, where R is selected from halogen, optionally substituted alkyl, aralkyl and aryl, OH, NH2, NHR1, NR1R2 and SR3, where R1, R2 and R3 are each optionally substituted alkyl, aralkyl or aryl groups;
B is selected from OH, NH2, NHR4, H and halogen, where R4 is an optionally substituted alkyl, aralkyl or aryl group;
D is selected from OH, NH2, NHR5, H, halogen and SCH3, where R5 is an optionally substituted alkyl, aralkyl or aryl group;
X and Y are independently selected from H, OH and halogen, with the proviso that when one of X and Y is hydroxy or halogen, the other is hydrogen;
Z is OH, or, when X is hydroxy, Z is selected from hydrogen, halogen, hydroxy, SQ and OQ, where Q is an optionally substituted alkyl, aralkyl or aryl group; and
W is OH or H, with the proviso that when W is OH, then A is CR where R is as defined above;
or a tautomer thereof, or a pharmaceutically acceptable salt thereof, or an ester thereof, or a prodrug thereof.

In certain embodiments, when B is NHR4 and/or D is NHR5, then R4 and/or R5 are C1-C4 alkyl.

In other embodiments, when one or more halogens are present they are chosen from chlorine and fluorine.

In another embodiment, when Z is SQ or OQ, Q is C1-C5 alkyl or phenyl.

In an exemplary embodiment, D is H, or when D is other than H, B is OH.

In another embodiment, B is OH, D is H, OH or NH2, X is OH or H, Y is H, most preferably with Z as OH, H, or methylthio, especially OH.

In certain embodiments W is OH, Y is H, X is OH, and A is CR where R is methyl or halogen, preferably fluorine.

In other embodiments, W is H, Y is H, X is OH and A is CH.

In other embodiments, a sirtuin-activating compound is an O-acetyl-ADP-ribose analog compound of formula 71:

71 wherein A, X, Y, Z and R are defined for compounds of formula (15) where first shown above; E is chosen from CO2H or a corresponding salt form, CO2R, CN, CONH2, CONHR or CONR2; and G is chosen from NH2, NHCOR, NHCONHR or NHCSNHR; or a tautomer thereof, or a pharmaceutically acceptable salt thereof, or an ester thereof, or a prodrug thereof.

In certain embodiments, E is CONH2 and G is NH2.

In other embodiments, E is CONH2, G is NH2, X is OH or H, is H, most preferable with Z as OH, H or methylthio, especially OH.

Exemplary sirtuin-activating compounds include the following:
(1S)-1,4-dideoxy-1-C-(4-hydroxypyrrolo[3,2-d]pyrimidin-7-yl)-1,4-imino-D-ribitol
(1S)-1-C-(2-amino-4-hydroxypyrrolo[3,2-d]pyrimidin-7-yl)-1,4-dideoxy-1,4-imino-D-ribitol
(1R)-1-C-(4-hydroxypyrrolo[3,2-d]pyrimidin-7-yl)-1,4-imino-1,2,4-trideoxy-D-erythro-pentitol
(1S)-1-C-(4-hydroxypyrrolo[3,2-d]pyrimidin-7-yl)-1,4-imino-1,4,5-trideoxy-D-ribitol
(1S)-1,4-dideoxy-1-C-(4-hydroxypyrrolo[3,2-d]pyrimidin-7-yl)-1,4-imino-5-methylthio-D-ribitol
(1S)-1,4-dideoxy-1-C-(2,4-dihydroxypyrrolo[3,2-d]pyrimidin-7-yl)-1,4-imino-D-ribitol
(1R)-1-C-(2,4-dihydroxypyrrolo[3,2-d]pyrimidin-7-yl)-1,4-imino-1,2,4-trideoxy-D-erthro-pentitol
(1S)-1-C-(2,4-dihydroxypyrrolo[3,2-d]pyrimidin-7-yl)-1,4-imino-1,4,5-trideoxy-D-ribitol
(1S)-1,4-dideoxy-1-C-(2,4-dihydroxypyrrolo[3,2-d]pyrimidin-7-yl)-1,4-imino-5-ethylthio-D-ribitol
(1R)-1-C-(2-amino-4-hydroxypyrrolo[3,2-d]pyrimidin-7-yl)-1,4-imino-1,2,4-trideoxy-D-erythro-pentitol
(1S)-1-C-(2-amino-4-hydroxypyrrolo[3,2-d]pyrimidin-7-yl)-1,4-imino-1,4,5-trideoxy-D-ribitol
(1S)-1-C-(2-amino-4-hydroxypyrrolo[3,2-d]pyrimidin-7-yl)-1,4-dideoxy-1,4-imino-5-methylthio-D-ribitol
(1S)-1,4-dideoxy-1-C-(7-hydroxypyrazolo[4,3-d]pyrimidin-3-yl)-1,4-imino-D-ribitol
(1R)-1-C-(7-hydroxypyrazolo[4,3-d]pyrimidin-3-yl)-1,4-imino-1,2,4-trideoxy-D-erythro-pentitol
(1S)-1-C-(7-hydroxypyrazolo[4,3-d]pyrimidin-3-yl)-1,4-imino-1,4,5-trideoxy-D-ribitol
(1S)-1,4-dideoxy-1-C-(7-hydroxypyrazolo[4,3-d]pyrimidin-3-yl)-1,4-imino-5-ethylthio-D-ribitol
(1S)-1,4-dideoxy-1-C-(5,7-dihydroxypyrazolo[4,3-d]pyrimidin-3-yl)-1,4-imino-D-ribitol
(1R)-1-C-(5,7-dihydroxypyrazolo[4,3-d]pyrimidin-3-yl)-1,4-imino-1,2,4-trideoxy-D-erythro-pentitol
(1S)-1-C-(5,7-dihydroxypyrazolo[4,3-d]pyrimidin-3-yl)-1,4-imino-1,4,5-trideoxy-D-ribitol
(1S)-1,4-dideoxy-1-C-(5,7-dihydroxypyrazolo[4,3-d]pyrimidin-3-yl)-1,4-imino-5-methylthio-D-ribitol
(1S)-1-C-(5-amino-7-hydroxypyrazolo[4,3-d]pyrimidin-3-yl)-1,4-dideoxy-1,4-imino-D-ribitol
(1R)-1-C—(S-amino-7-hydroxypyrazolo[4,3-d]pyrimidin-3-yl)-1,4-imino-1,2,4-trideoxy-D-erythro-pentitol
(1S)-1-C-(5-amino-7-hydroxypyrazolo[4,3-d]pyrimidin-3-yl)-1,4-imino-1,4,5-trideoxy-D-ribitol
(1S)-1-C-(5-amino-7-hydroxypyrazolo[4,3-d]pyrimidin-3-yl)-1,4-dideoxy-1,4-imino-5-methylthio-D-ribitol
(1S)-1-C-(3-amino-2-carboxamido-4-pyrroyl)-1,4-dideoxy-1,4-imino-D-ribitol.
(1S)-1,4-dideoxy-1-C-(4-hydroxypyrrolo[3,2-d]pyrimidin-7-yl)-1,4-imino-D-ribitol 5-phosphate
(1S)-1-C-(2-amino-4-hydroxypyrrolo[3,2-d]pyrimidin-7-yl)-1,4-imino-D-ribitol 5-phosphate
(1S)-1-C-(3-amino-2-carboxamido-4-pyrrolyl)-1,4-dideoxy-1,4-imino-D-ribitol In yet other embodiments, sirtuin-activating compounds are O-acetyl-ADP-ribose analog compounds of formula 72 and 73, their tautomers and pharmaceutically acceptable salts.

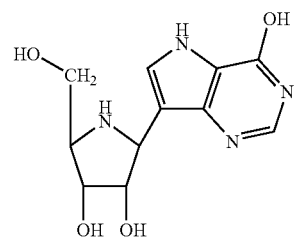

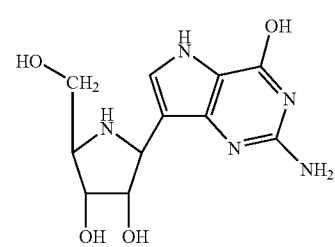

The biological availability of a compound of formula (70) or formula (71) can be enhanced by conversion into a pro-drug form. Such a pro-drug can have improved lipophilicity relative to the compound of formula (70) or formula (71), and this can result in enhanced membrane permeability. One particularly useful form of a pro-drug is an ester derivative. Its utility relies upon the action of one or more of the ubiquitous intracellular lipases to catalyse the hydrolysis of these ester group(s), to release the compound of formula (70) and formula (71) at or near its site of action.

In one form of a prodrug, one or more of the hydroxy groups in a compound of formula (70) or formula (71) can be O-acylated, to make, for example a 5-O-butyrate or a 2,3-di-O-butyrate derivative.

Prodrug forms of 5-phosphate ester derivative of a compounds of formula (70) or formula (71) can also be made and may be particularly useful, since the anionic nature of the 5-phosphate may limit its ability to cross cellular membranes. Conveniently, such a 5-phosphate derivative can be converted to an uncharged bis(acyloxymethyl) ester derivative. The utility of such a pro-drug relies upon the action of one or more of the ubiquitous intracellular lipases to catalyse the hydrolysis of these ester group(s), releasing a molecule of formaldehyde and the compound of formula (70) or formula (71) at or near its site of action.

In an exemplary embodiment, analogs of 2'-AADPR or 3'-AADPR that are designed to have increased stability from esterase action through the use of well-known substitutes for ester oxygen atoms that are subject to esterase attack. The esterase-labile oxygen atoms in 2'-AADPR and 3'-AADPR would be understood to be the ester oxygen linking the acetate group with the ribose, and the ester oxygen between the two phosphorus atoms. As is known in the art, substitution of either or both of these ester oxygen atoms with a CF2, a NH, or a S would be expected to provide a 2'-AADPR or 3'-AADPR analog that is substantially more stable due to increased resistance to esterase action.

Thus, in some embodiments, the invention is directed to analogs 2'-O-acetyl-ADP-ribose or 3'-O-acetyl-ADP-ribose exhibiting increased stability in cells. The preferred analogs comprise a CF2, a NH, or a S instead of the acetyl ester oxygen or the oxygen between two phosphorus atoms. The most preferred substitute is CF2. Replacement of the acetyl ester oxygen is particularly preferred. In other preferred embodiments, both the ester oxygen and the oxygen between the two phosphorus atoms are independently substituted with a CF2, a NH, or a S.

A preferred compound of formula 8 is Dipyridamole; a preferred compound of formula 12 is Hinokitiol; a preferred compound of formula 13 is L-(+)-Ergothioneine; a preferred compound of formula 19 is Caffeic Acid Phenol Ester; a preferred compound of formula 20 is MCI-186 and a preferred compound of formula 21 is HBED. Activating compounds may also be oxidized forms of any of the compounds described herein.

Sirtuin activating compounds are further described, e.g., in Howitz et al. Nature 425:191; WO 04/016726; WO 05/002672; WO 2005/065667 and U.S. 20060025337.

Any other known sirtuin activator may be used in the methods described herein. In particular, sirtuin activators that may be used are described in US applications having publication numbers 20060111435; 20060084085; 20060025337; 20050267023; 20050171027; 20050136537; 20050096256, and PCT applications having publication numbers WO 2007/084861; WO 2007/084857; WO 2007/005453; WO 2006/138418; WO 2006/096780; WO 2006/086454; WO 2006/068656; WO 2006/007411; WO 2005/065667; WO 2005/002672; WO 20051002555; and WO 2004/016726, all of which are specifically incorporated by reference herein. In particular, each and every compound and chemical formula that is set forth in these publications, including the patent applications, is specifically incorporated by reference as if it was specifically described in the instant application. Other sirtuin activators that may be used are described, e.g., in Milne et al. (2007) Nature 450:712; in US applications having publication numbers 20060229265; 20060276393; 20060276416; 20060292099; 20070014833; 20070037809; 20070037827; 20070037865; 20070043050 and PCT applications having publication numbers WO 2007/064902; WO 2007/019417; WO 2007/019416; WO 2007/019346; WO 2007/019345; WO 2007/019344; WO 2007/008548; WO 2006/127987; WO 2006/105440; WO 2006/105403; WO 2006/094248; WO 2006/094246; WO 2006/094239; WO 2006/094237; WO 2006/094236; WO 2006/094235; WO 2006/094233; WO 2006/094210; WO 2006/094209; WO 2006/079021; WO 2006/078941; WO 2006/076681, all of which are specifically incorporated by reference herein. In particular, each and every compound and chemical formula that is set forth in these publications, including the patent applications, is specifically incorporated by reference as if it was specifically described in the instant application. If a compound is described in a document that is incorporated by reference, it should be understood that it is as if the compound has been described herein.

Also included are pharmaceutically acceptable addition salts and complexes of the compounds described herein or incorporated by reference herein, e.g., compounds of formulas 1-25, 30, and 32-73. In cases wherein the compounds may have one or more chiral centers, unless specified, the compounds contemplated herein may be a single stereo isomer or racemic mixtures of stereo isomers.

In cases in which the compounds have unsaturated carbon-carbon double bonds, both the cis (Z) and trans (E) isomers are contemplated herein. In cases wherein the compounds may exist in tautomeric forms, such as keto-enol tautomers, such as

and

each tautomeric form is contemplated as being included within the methods presented herein, whether existing in equilibrium or locked in one form by appropriate substitution with R'. The meaning of any substituent at any one occurrence is independent of its meaning, or any other substituent's meaning, at any other occurrence.

Also included in the methods presented herein are prodrugs of the compounds of formulas 1-25, 30, and 32-73. Prodrugs are considered to be any covalently bonded carriers that release the active parent drug in vivo. Metabolites, such as in vivo degradation products, of the compounds described herein are also included.

Analogs and derivatives of the above-described compounds can also be used for activating a member of the sirtuin protein family. For example, derivatives or analogs may make the compounds more stable or improve their ability to traverse cell membranes or being phagocytosed or pinocytosed. Exemplary derivatives include glycosylated derivatives, as described, e.g., in U.S. Pat. No. 6,361,815 for resveratrol. Other derivatives of resveratrol include cis- and trans-resveratrol and conjugates thereof with a saccharide, such as to form a glucoside (see, e.g., U.S. Pat. No. 6,414,037). Glucoside polydatin, referred to as piceid or resveratrol 3-O-beta-D-glucopyranoside, can also be used. Saccharides to which compounds may be conjugated include glucose, galactose, maltose, lactose and sucrose. Glycosylated stilbenes are further described in Regev-Shoshani et al. Biochemical J. (published on Apr. 16, 2003 as BJ20030141). Other derivatives of compounds described herein are esters, amides and prodrugs. Esters of resveratrol are described, e.g., in U.S. Pat. No. 6,572,882. Resveratrol and derivatives thereof can be prepared as described in the art, e.g., in U.S. Pat. Nos. 6,414,037; 6,361,815; 6,270,780; 6,572,882; and Brandolini et al. (2002) J. Agric. Food. Chem. 50:7407. Derivatives of hydroxyflavones are described, e.g., in U.S. Pat. No. 4,591,600. Resveratrol and other activating compounds can also be obtained commercially, e.g., from Sigma. Other sirtuin activators may be identified as described, e.g., in WO 05/002555.

In certain embodiments, if an activating compound occurs naturally, it may be at least partially isolated from its natural environment prior to use. For example, a plant polyphenol may be isolated from a plant and partially or significantly purified prior to use in the methods described herein. An activating compound may also be prepared synthetically, in which case it would be free of other compounds with which it is naturally associated. In an illustrative embodiment, an activating composition comprises, or an activating compound is associated with, less than about 50%, 10%, 1%, 0.1%, $10^{-2}$% or $10^{-3}$% of a compound with which it is naturally associated.

A sirtuin is activated by a compound when at least one of its biological activities, e.g., deacetylation activity, is higher in the presence of the compound than in its absence. Activation may be by a factor of at least about 10%, 30%, 50%, 100%

(i.e., a factor of two), 3, 10, 30, or 100. The extent of activation can be determined, e.g., by contacting the activated sirtuin with a deacetylation substrate and determining the extent of deacetylation of the substrate, as further described herein. The observation of a lower level of acetylation of the substrate in the presence of a test sirtuin relative to the presence of a non activated control sirtuin indicates that the test sirtuin is activated. Sirtuin proteins may be prepared recombinantly or isolated from cells according to methods known in the art.

Administration may be local, e.g., topical, parenteral, oral, or other depending on the desired result of the administration (as further described herein). Administration may be followed by measuring a factor in the subject or the cell, such as the activity of the sirtuin, of the lifespan or stress resistance of the cell. In an illustrative embodiment, a cell is obtained from a subject following administration of an activating compound to the subject, such as by obtaining a biopsy, and the activity of the sirtuin is determined in the biopsy. The cell may be any cell of the subject, but in cases in which an activating compound is administered locally, the cell is preferably a cell that is located in the vicinity of the site of administration.

Also encompassed are methods comprising administering one or more activating compounds having a formula selected from the group of formulas 1-73. Compounds may be in a pharmaceutical composition, such as a pill or other formulation for oral administration, further described herein. Compositions may also comprise or consist of extracts of plants, red wine or other source of the compounds.

In certain embodiments, a method comprises administering a sirtuin activating compound of a genus of compounds (e.g., having formula I), with the proviso that the genus does not include one or more specific compounds. For example, in certain embodiments, a sirtuin activator compound may be a compound of any one of formulas 1-25, 30 and 32-73 with the proviso that the compound is not resveratrol, a flavone, a flavonoid, a catechin, epicatechin, gallocatechin (or other compound recited in U.S. 2005/0004046) or any of the other compounds specifically recited herein.

A sirtuin activator may be in a form that is naturally occurring, e.g., it can be a naturally occurring compound. It can also be a non-naturally occurring compound. A "form that is naturally occurring" when referring to a compound means a compound that is in a form, e.g., a composition, in which it can be found naturally. For example, since resveratrol can be found in red wine, it is present in red wine in a form that is naturally occurring. A compound is not in a form that is naturally occurring if, e.g., the compound has been purified and separated from at least some of the other molecules that are found with the compound in nature. A "naturally occurring compound" refers to a compound that can be found in nature, i.e., a compound that has not been designed by man. A naturally occurring compound may have been made by man or by nature. For example, resveratrol is a naturally-occurring compound. A "non-naturally occurring compound" is a compound that is not known to exist in nature or that does not occur in nature.

For example, a compound can be taken by subjects as a food or dietary supplement. In one embodiment, such a compound is a component of a multi-vitamin complex. Compounds can also be added to existing formulations that are taken on a daily basis, e.g., statins and aspirin. Compounds may also be used as food additives.

Compounds described herein could also be taken as one component of a multi-drug complex or as a supplement in addition to a multi-drug regimen. In one embodiment, this multi-drug complex or regimen would include drugs or compounds for improving or preventing the decline of a cognitive function.

Compositions or coformulations comprising a sirtuin activator and another agent, e.g., Vitamin B3 analogs, retinoids, alpha-hydroxy acid, ascorbic acid, are also encompassed herein.

In certain embodiments, the subject sirtuin activators, such as SIRT1 activators, do not have any substantial ability to inhibit PI3-kinase, inhibit aldoreductase and/or inhibit tyrosine protein kinases at concentrations (e.g., in vivo) effective for activating the deacetylase activity of the sirtuin, e.g., SIRT1. For instance, in preferred embodiments the sirtuin activator is chosen to have an $EC_{50}$ for activating sirtuin deacetylase activity that is at least 5 fold less than the $EC_{50}$ for inhibition of one or more of aldoreductase and/or tyrosine protein kinases, and even more preferably at least 10 fold, 100 fold or even 1000 fold less.

In certain embodiments, the subject sirtuin activators do not have any substantial ability to transactivate EGFR tyrosine kinase activity at concentrations (e.g., in vivo) effective for activating the deacetylase activity of the sirtuin. For instance, in preferred embodiments the sirtuin activator is chosen to have an $EC_{50}$ for activating sirtuin deacetylase activity that is at least 5 fold less than the $EC_{50}$ for transactivating EGFR tyrosine kinase activity, and even more preferably at least 10 fold, 100 fold or even 1000 fold less.

In certain embodiments, the subject sirtuin activators do not have any substantial ability to cause coronary dilation at concentrations (e.g., in vivo) effective for activating the deacetylase activity of the sirtuin. For instance, in preferred embodiments the sirtuin activator is chosen to have an $EC_{50}$ for activating sirtuin deacetylase activity that is at least 5 fold less than the $EC_{50}$ for coronary dilation, and even more preferably at least 10 fold, 100 fold or even 1000 fold less.

In certain embodiments, the subject sirtuin activators do not have any substantial spasmolytic activity at concentrations (e.g., in vivo) effective for activating the deacetylase activity of the sirtuin. For instance, in preferred embodiments the sirtuin activator is chosen to have an $EC_{50}$ for activating sirtuin deacetylase activity that is at least 5 fold less than the $EC_{50}$ for spasmolytic effects (such as on gastrointestinal muscle), and even more preferably at least 10 fold, 100 fold or even 1000 fold less.

In certain embodiments, the subject sirtuin activators do not have any substantial ability to inhibit hepatic cytochrome P450 1B1 (CYP) at concentrations (e.g., in vivo) effective for activating the deacetylase activity of the sirtuin. For instance, in preferred embodiments the sirtuin activator is chosen to have an $EC_{50}$ for activating sirtuin deacetylase activity that is at least 5 fold less than the $EC_{50}$ for inhibition of P450 1B1, and even more preferably at least 10 fold, 100 fold or even 1000 fold less.

In certain embodiments, the subject sirtuin activators do not have any substantial ability to inhibit nuclear factor-kappaB (NF-κB) at concentrations (e.g., in vivo) effective for activating the deacetylase activity of the sirtuin. For instance, in preferred embodiments the sirtuin activator is chosen to have an $EC_{50}$ for activating sirtuin deacetylase activity that is at least 5 fold less than the $EC_{50}$ for inhibition of NF-κB, and even more preferably at least 10 fold, 100 fold or even 1000 fold less.

In certain embodiments, the subject SIRT1 activators do not have any substantial ability to activate SIRT1 orthologs in lower eukaryotes, particularly yeast or human pathogens, at concentrations (e.g., in vivo) effective for activating the deacetylase activity of human SIRT1. For instance, in preferred embodiments the SIRT1 activator is chosen to have an EC50 for activating human SIRT1 deacetylase activity that is at least 5 fold less than the EC50 for activating yeast Sir2 (such as *Candida, S. cerevisiae*, etc), and even more preferably at least 10 fold, 100 fold or even 1000 fold less.

In other embodiments, the subject sirtuin activators do not have any substantial ability to inhibit protein kinases; to phosphorylate mitogen activated protein (MAP) kinases; to inhibit the catalytic or transcriptional activity of cyclo-oxygenases, such as COX-2; to inhibit nitric oxide synthase (iNOS); or to inhibit platelet adhesion to type I collagen at concentrations (e.g., in vivo) effective for activating the deacetylase activity of the sirtuin. For instance, in preferred embodiments, the sirtuin activator is chosen to have an $EC_{50}$ for activating sirtuin deacetylase activity that is at least 5 fold less than the $EC_{50}$ for performing any of these activities, and even more preferably at least 10 fold, 100 fold or even 1000 fold less.

In other embodiments, a compound described herein does not have significant or detectable anti-oxidant activities, as determined by any of the standard assays known in the art. For example, a compound does not significantly scavenge free-radicals, such as $O_2$ radicals. A compound may have less than about 2, 3, 5, 10, 30 or 100 fold anti-oxidant activity relative to another compound, e.g., resveratrol.

A compound may also have a binding affinity for a sirtuin of about $10^{-9}$M, $10^{-10}$M, $10^{-11}$M, $10^{-12}$M or less. A compound may reduce the $K_m$ of a sirtuin for its substrate or $NAD^+$ by a factor of at least about 2, 3, 4, 5, 10, 20, 30, 50 or 100. A compound may have an $EC_{50}$ for activating the deacetylase activity of a sirtuin of less than about 1 nM, less than about 10 nM, less than about 100 nM, less than about 1 µM, less than about 10 µM, less than about 100 µM, or from about 1-10 nM, from about 10-100 nM, from about 0.1-1 µM, from about 1-10 µM or from about 10-100 µM. A compound may activate the deacetylase activity of a sirtuin by a factor of at least about 5, 10, 20, 30, 50, or 100, as measured in an acellular assay or in a cell based assay as described in the Examples. A compound may cause at least a 10%, 30%, 50%, 80%, 2 fold, 5 fold, 10 fold, 50 fold or 100 fold greater induction of the deacetylase activity of SIRT1 relative to the same concentration of resveratrol or other compound described herein. A compound may also have an $EC_{50}$ for activating SIRT5 that is at least about 10 fold, 20 fold, 30 fold, 50 fold greater than that for activating SIRT1.

A compound may traverse the cytoplasmic membrane of a cell. For example, a compound may have a cell-permeability of at least about 20%, 50%, 75%, 80%, 90% or 95%.

Compounds described herein may also have one or more of the following characteristics: the compound may be essentially non-toxic to a cell or subject; the compound may be an organic molecule or a small molecule of 2000 amu or less, 1000 amu or less; a compound may have a half-life under normal atmospheric conditions of at least about 30 days, 60 days, 120 days, 6 months or 1 year; the compound may have a half-life in solution of at least about 30 days, 60 days, 120 days, 6 months or 1 year; a compound may be more stable in solution than resveratrol by at least a factor of about 50%, 2 fold, 5 fold, 10 fold, 30 fold, 50 fold or 100 fold; a compound may promote deacetylation of the DNA repair factor Ku70; a compound may promote deacetylation of RelA/p65; a compound may increase general turnover rates and enhance the sensitivity of cells to TNF-induced apoptosis.

In certain embodiments, a sirtuin activator, e.g., resveratrol or nicotinamide riboside, is administered at a dose having a sirtuin activating effect equal to or greater than 200 mg resveratrol, e.g., at least about 200, 300, 400, 500, 600, 700, 800, 900 or 1000 mg/kg/day of resveratrol. Other doses are set forth in US application publication No. 20070149466, which is specifically incorporated by reference herein.

DEFINITIONS FOR CHEMICAL COMPOUNDS

The term "cis" is art-recognized and refers to the arrangement of two atoms or groups around a double bond such that the atoms or groups are on the same side of the double bond. C is configurations are often labeled as (Z) configurations.

The term "trans" is art-recognized and refers to the arrangement of two atoms or groups around a double bond such that the atoms or groups are on the opposite sides of a double bond. Trans configurations are often labeled as (E) configurations.

The term "covalent bond" is art-recognized and refers to a bond between two atoms where electrons are attracted electrostatically to both nuclei of the two atoms, and the net effect of increased electron density between the nuclei counterbalances the internuclear repulsion. The term covalent bond includes coordinate bonds when the bond is with a metal ion.

The term "synthetic" is art-recognized and refers to production by in vitro chemical or enzymatic synthesis.

The term "meso compound" is art-recognized and refers to a chemical compound which has at least two chiral centers but is achiral due to a plane or point of symmetry.

The term "chiral" is art-recognized and refers to molecules which have the property of non-superimposability of the mirror image partner, while the term "achiral" refers to molecules which are superimposable on their mirror image partner. A "prochiral molecule" is a molecule which has the potential to be converted to a chiral molecule in a particular process.

The term "stereoisomers" is art-recognized and refers to compounds which have identical chemical constitution, but differ with regard to the arrangement of the atoms or groups in space. In particular, "enantiomers" refer to two stereoisomers of a compound which are non-superimposable mirror images of one another. "Diastereomers", on the other hand, refers to stereoisomers with two or more centers of dissymmetry and whose molecules are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product.

The term "regioisomers" is art-recognized and refers to compounds which have the same molecular formula but differ in the connectivity of the atoms. Accordingly, a "regioselective process" is one which favors the production of a particular regioisomer over others, e.g., the reaction produces a statistically significant increase in the yield of a certain regioisomer.

The term "epimers" is art-recognized and refers to molecules with identical chemical constitution and containing more than one stereocenter, but which differ in configuration at only one of these stereocenters.

The term "structure-activity relationship" or "(SAR)" is art-recognized and refers to the way in which altering the molecular structure of a drug or other compound alters its biological activity, e.g., its interaction with a receptor, enzyme, nucleic acid or other target and the like.

The term "aliphatic" is art-recognized and refers to a linear, branched, cyclic alkane, alkene, or alkyne. In certain embodiments, aliphatic groups in the present compounds are linear or branched and have from 1 to about 20 carbon atoms.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure. The term "alkyl" is also defined to include halosubstituted alkyls.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "heteroatom" is art-recognized and refers to an atom of any element other than carbon or hydrogen. Illustrative heteroatoms include boron, nitrogen, oxygen, phosphorus, sulfur and selenium.

The term "aryl" is art-recognized and refers to 5-, 6- and 7-membered single-ring aromatic groups that may include from zero to four heteroatoms, for example, benzene, naphtalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle" is art-recognized and refers to an aromatic or non-aromatic ring in which each atom of the ring is carbon.

The term "nitro" is art-recognized and refers to —$NO_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —$SO_2^-$. "Halide" designates the corresponding anion of the halogens, and "pseudohalide" has the definition set forth on 560 of "*Advanced Inorganic Chemistry*" by Cotton and Wilkinson.

The terms "amine" and "amino" are art-recognized and refer to both unsubstituted and substituted amines, e.g., a moiety that may be represented by the general formulas:

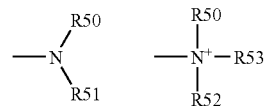

wherein R50, R51 and R52 each independently represent a hydrogen, an alkyl, an alkenyl, —$(CH_2)_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —$(CH_2)_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

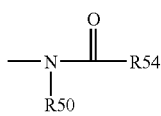

wherein R50 is as defined above, and R54 represents a hydrogen, an alkyl, an alkenyl or —$(CH_2)_m$—R61, where m and R61 are as defined above.

The term "amido" is art recognized as an amino-substituted carbonyl and includes a moiety that may be represented by the general formula:

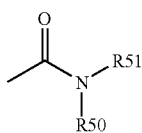

wherein R50 and R51 are as defined above. Certain embodiments of amides may not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—$(CH_2)_m$—R61, wherein m and R61 are defined above. Representative alkylthio groups include methylthio, ethyl thio, and the like.

The term "carbonyl" is art recognized and includes such moieties as may be represented by the general formulas:

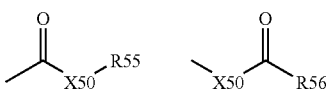

wherein X50 is a bond or represents an oxygen or a sulfur, and R55 and R56 represents a hydrogen, an alkyl, an alkenyl, —$(CH_2)_m$—R61 or a pharmaceutically acceptable salt, R56 represents a hydrogen, an alkyl, an alkenyl or —$(CH_2)_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—$(CH_2)_m$—R61, where m and R61 are described above.

The term "sulfonate" is art recognized and refers to a moiety that may be represented by the general formula:

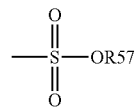

in which R57 is an electron pair, hydrogen, alkyl, cycloalkyl, or aryl.

The term "sulfate" is art recognized and includes a moiety that may be represented by the general formula:

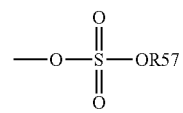

in which R57 is as defined above.

The term "sulfonamido" is art recognized and includes a moiety that may be represented by the general formula:

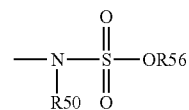

in which R50 and R56 are as defined above.

The term "sulfamoyl" is art-recognized and refers to a moiety that may be represented by the general formula:

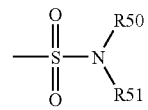

in which R50 and R51 are as defined above.

The term "sulfonyl" is art-recognized and refers to a moiety that may be represented by the general formula:

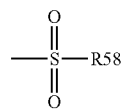

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

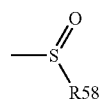

in which R58 is defined above.

The term "phosphoryl" is art-recognized and may in general be represented by the formula:

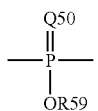

wherein Q50 represents S or O, and R59 represents hydrogen, a lower alkyl or an aryl. When used to substitute, e.g., an alkyl, the phosphoryl group of the phosphorylalkyl may be represented by the general formulas:

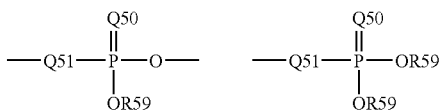

wherein Q50 and R59, each independently, are defined above, and Q51 represents O, S or N. When Q50 is S, the phosphoryl moiety is a "phosphorothioate".

The term "phosphoramidite" is art-recognized and may be represented in the general formulas:

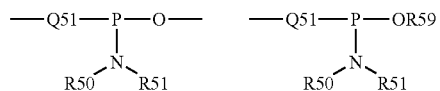

wherein Q51, R50, R51 and R59 are as defined above.

The term "phosphonamidite" is art-recognized and may be represented in the general formulas:

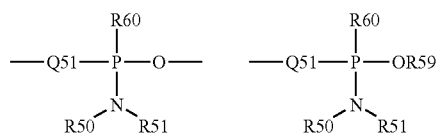

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g. alkyl, m, n, and the like, when it occurs more than once in any structure, is intended to be independent of its definition elsewhere in the same structure.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—(CH$_2$)$_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compounds contained in compositions described herein may exist in particular geometric or stereoisomeric forms. In addition, compounds may also be optically active. Contemplated herein are all such compounds, including cis- and trans-isomers, R- and S-enantiomers, diastereomers, (D)-isomers, (L)-isomers, the racemic mixtures thereof, and other mixtures thereof. Additional asymmetric carbon atoms may be present in a substituent such as an alkyl group. All such isomers, as well as mixtures thereof, are encompassed herein.

If, for instance, a particular enantiomer of a compound is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. Heteroatoms such as nitrogen may have hydrogen substituents and/or any permissible substituents of organic compounds described herein which satisfy the valences of the heteroatoms. Compounds are not intended to be limited in any manner by the permissible substituents of organic compounds.

The chemical elements are identified in accordance with the Periodic Table of the Elements, CAS version, *Handbook of Chemistry and Physics*, 67th Ed., 1986-87, inside cover.

The term "protecting group" is art-recognized and refers to temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed by Greene and Wuts in *Protective Groups in Organic Synthesis* (2$^{nd}$ ed., Wiley: New York, 1991).

The term "hydroxyl-protecting group" is art-recognized and refers to those groups intended to protect a hydroxyl group against undesirable reactions during synthetic procedures and includes, for example, benzyl or other suitable esters or ethers groups known in the art.

The term "carboxyl-protecting group" is art-recognized and refers to those groups intended to protect a carboxylic acid group, such as the C-terminus of an amino acid or peptide or an acidic or hydroxyl azepine ring substituent, against undesirable reactions during synthetic procedures and includes. Examples for protecting groups for carboxyl groups involve, for example, benzyl ester, cyclohexyl ester, 4-nitrobenzyl ester, t-butyl ester, 4-pyridylmethyl ester, and the like.

The term "amino-blocking group" is art-recognized and refers to a group which will prevent an amino group from participating in a reaction carried out on some other functional group, but which can be removed from the amine when desired. Such groups are discussed by in Ch. 7 of Greene and Wuts, cited above, and by Barton, *Protective Groups in Organic Chemistry* ch. 2 (McOmie, ed., Plenum Press, New York, 1973). Examples of suitable groups include acyl protecting groups such as, to illustrate, formyl, dansyl, acetyl, benzoyl, trifluoroacetyl, succinyl, methoxysuccinyl, benzyl and substituted benzyl such as 3,4-dimethoxybenzyl, o-nitrobenzyl, and triphenylmethyl; those of the formula —COOR where R includes such groups as methyl, ethyl, propyl, isopropyl, 2,2,2-trichloroethyl, 1-methyl-1-phenylethyl, isobutyl, t-butyl, t-amyl, vinyl, allyl, phenyl, benzyl, p-nitrobenzyl, o-nitrobenzyl, and 2,4-dichlorobenzyl; acyl groups and substituted acyl such as formyl, acetyl, chloroacetyl, dichloroacetyl, trichloroacetyl, trifluoroacetyl, benzoyl, and p-methoxybenzoyl; and other groups such as methanesulfonyl, p-toluenesulfonyl, p-bromobenzenesulfonyl, p-nitrophenylethyl, and p-toluenesulfonyl-aminocarbonyl. Preferred amino-blocking groups are benzyl (—$CH_2C_6H_5$), acyl [C(O)$R_1$] or Si$R'_3$ where $R_1$ is $C_1$-$C_4$ alkyl, halomethyl, or 2-halo-substituted-($C_2$-$C_4$ alkoxy), aromatic urethane protecting groups as, for example, carbonylbenzyloxy (Cbz); and aliphatic urethane protecting groups such as t-butyloxycarbonyl (Boc) or 9-fluorenylmethoxycarbonyl (FMOC).

The definition of each expression, e.g. lower alkyl, m, n, p and the like, when it occurs more than once in any structure, is intended to be independent of its definition elsewhere in the same structure.

The term "electron-withdrawing group" is art-recognized, and refers to the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, March, *Advanced Organic Chemistry* 251-59 (McGraw Hill Book Company: New York, 1977). The Hammett constant values are generally negative for electron donating groups ($\sigma(P)$=−0.66 for $NH_2$) and positive for electron withdrawing groups ($\sigma(P)$=0.78 for a nitro group), $\sigma(P)$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "small molecule" is art-recognized and refers to a composition which has a molecular weight of less than about 2000 amu, or less than about 1000 amu, and even less than about 500 amu. Small molecules may be, for example, nucleic acids, peptides, polypeptides, peptide nucleic acids, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays described herein. The term "small organic molecule" refers to a small molecule that is often identified as being an organic or medicinal compound, and does not include molecules that are exclusively nucleic acids, peptides or polypeptides.

The term "prophylactic" or "therapeutic" treatment is art-recognized and refers to administration of a drug to a host. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

The term "bioavailable" when referring to a compound is art-recognized and refers to a form of a compound that allows for it, or a portion of the amount of compound administered, to be absorbed by, incorporated to, or otherwise physiologically available to a subject or patient to whom it is administered.

The term "pharmaceutically-acceptable salts" is art-recognized and refers to the relatively non-toxic, inorganic and organic acid addition salts of compounds, including, for example, those contained in compositions described herein.

Other Exemplary Agents that May be Used

Methods for improving cognitive performance or for preventing or compensating for cognitive decline may also comprise increasing the protein level of a sirtuin, such as SIRT1, or a biologically active fragment thereof.

"Biologically active portion of a sirtuin" refers to a portion of a sirtuin protein having a biological activity, such as the ability to deacetylate. Biologically active portions of sirtuins may comprise the core domain of sirtuins. For example, amino acids 62-293 of SIRT1, which are encoded by nucleotides 237 to 932 of the nucleotide sequence, encompass the $NAD^+$ binding domain and the substrate binding domain. Therefore, this region is sometimes referred to as the core domain. Other biologically active portions of SIRT1, also sometimes referred to as core domains, include about amino acids 261 to 447, which are encoded by nucleotides 834 to 1394 of the nucleotide sequence; about amino acids 242 to 493, which are encoded by nucleotides 777 to 1532 of the nucleotide sequence; or about amino acids 254 to 495, which are encoded by nucleotides 813 to 1538 of the nucleotide sequence.

Increasing protein levels can be achieved by introducing into a cell one or more copies of a nucleic acid that encodes a sirtuin or a fragment thereof. For example, the level of SIRT1 can be increased in a mammalian cell by introducing into the mammalian cell a nucleic acid encoding SIRT1. The nucleic acid may be under the control of a promoter that regulates the expression of the SIRT1 nucleic acid. Alternatively, the nucleic acid may be introduced into the cell at a location in the genome that is downstream of a promoter. Methods for increasing the level of a protein by these ways are well known in the art. Illustrative methods are described in the Examples.

A nucleic acid that is introduced into a cell to increase the protein level of a sirtuin may encode a protein that is at least about 80%, 85%, 90%, 95%, 98%, or 99% identical to the sequence of a sirtuin. For example, the nucleic acid encoding the protein may be at least about 80%, 85%, 90%, 95%, 98%, or 99% identical to a nucleotide sequence encoding SIRT1. The nucleic acid may also be a nucleic acid that hybridizes, preferably under stringent hybridization conditions, to a nucleic acid encoding a wild-type sirtuin. Stringent hybridization conditions may include hybridization and a wash in 0.2×SSC at 65° C. When using a nucleic acid that encodes a protein that is different from a wild-type sirtuin protein, such as a protein that is a fragment of a wild-type sirtuin, the protein is preferably biologically active, e.g., is capable of deacetylation. It is only necessary to express in a cell a portion of the sirtuin that is biologically active. For example, a protein that differs from wild-type SIRT1 preferably contains the core structure thereof. Whether a protein retains a biological function, e.g., deacetylation capabilities, can be determined according to methods known in the art.

The term "percent identical" refers to sequence identity between two amino acid sequences or between two nucleotide sequences. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Preferably, an alignment program that permits gaps in the sequence is utilized to align the sequences. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

In certain embodiments, a nucleic acid encoding a sirtuin or a biologically active portion thereof is administered to a subject in the form of a vector, such as an expression vector. Any means for the introduction of polynucleotides into mammals, human or non-human, or cells thereof may be adapted to the practice of this invention for the delivery of the various constructs of the invention into the intended recipient. In one embodiment of the invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat. Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

In one method of the invention, the DNA constructs are delivered using viral vectors. The transgene may be incorporated into any of a variety of viral vectors useful in gene therapy, such as recombinant retroviruses, adenovirus, adeno-associated virus (AAV), hybrid adenovirus-AAV vector, retroviral vector, herpes simplex virus-1, vaccinia virus and RNA viruses, or recombinant bacterial or eukaryotic plasmids.

In another embodiment, the level of a sirtuin protein is increased in a cell by contacting cells with a sirtuin protein, e.g., by administering a sirtuin to a subject. Sirtuin proteins may be modified or packaged in such a way as to increase their passage through a cell membrane. Proteins may be administered with a delivery system, such as liposomes.

Methods for increasing sirtuin protein levels also include methods for stimulating the transcription of genes encoding sirtuins, methods for stabilizing the corresponding mRNAs, methods, and other methods known in the art. Upstream activators of sirtuins, e.g., those in the NAD+ salvage pathway, as described, e.g., in WO 04/016726, may also be used.

In other embodiments, methods of treatment include increasing the flux through the NAD+ salvage pathway or reducing nicotinamide levels, such as described in WO 2004/01676. The activity or protein level of an enzyme of the NAD+ salvage pathway, such as PNC1, NPT1 (or human homologues thereof) or nicotinamide phosphoribosyltransferase (NAMPRT) may be increased. The human gene for NAMPRT is also referred to as pre-B-cell colony enhancing factor 1 (PBEF1) and visfatin and exists as two isoforms (see, e.g., Samal et al. (1994) Mol. Cell. Biol. 14:1431, Rongwaux et al. (2002) Euro. J. Immunol. 32:3225 and Fukuhara et al. Science 307:426-30 (2005); U.S. Pat. Nos. 5,874,399 and 6,844,163). The sequence of isoform a is available under GenBank Accession numbers NM_005746, NP_005737 and U02020 and the sequence of isoform b is available under GenBank Accession numbers NM_182790, NP_877591 and BC020691.

In yet other embodiments, nicotinamide riboside or analogs thereof are administered. Nicotinamide riboside can be prepared by treating NMN (from, e.g., Sigma) with a phosphatase, as described, e.g., in Bieganowski et al. (2004) Cell 117:495. Nicotinamide riboside can be in the oxidized or reduced form, the latter of which appears to be more stable (Friedlos et al. (1992) Biochem Pharmacol. 44:631. Nicotinamide riboside (74) is depicted below.

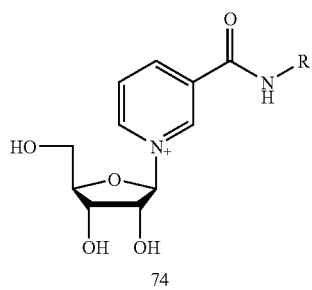

Nicotinamide riboside and some of its analogs are represented by formula A:

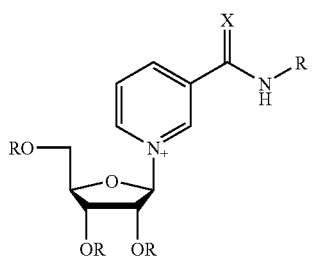

wherein

R represents independently for each occurrence H, acetyl, benzoyl, acyl, phosphate, sulfate, (alkyoxy)methyl, triarylmethyl, (trialkyl)silyl, (dialkyl)(aryl)silyl, (alkyl)(diaryl)silyl, or (triaryl)silyl; and X represents O or S.

Nicotinamide riboside can be contacted with the cell at a concentration of about 1 nM to 10 μM. A cell may be optionally contacted with an agent that increases protein or activity levels of a nicotinamide riboside kinase (Nrk) enzyme, that phosphorylates nicotinamide riboside to form nicotinamide mononucleotide (NMN). Nrk exits in one form in yeast, Nrk1, and in two forms in humans, Nrk1 (GenBank Accession No. NM_017881.1; NP_060351) and Nrk2 (GenBank Accession Nos. NM_170678; NP_733778).

Exemplary Methods

Provided herein are methods for improving cognitive performance or a cognitive function in a subject or for preventing or compensating for the decline or impairment of cognitive performance. A method may comprise administering to a subject, e.g., a subject in need thereof, a therapeutically effective amount of an agent that increases the activity or protein level of a sirtuin protein, such as human SIRT1. A subject may be a mammal, such as a human, canine, feline, equine, bovine, ovine, porcine, sheep, mouse or rat. A subject may also be a non-human mammal.

The term "agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fruits, vegetables, nuts, oil, wine, fungi, or animal (particularly mammalian) cells or tissues. The activity of such agents may render it suitable as a "therapeutic agent" which is a biologically, physiologically, or pharmacologically active substance (or substances) that acts locally or systemically in a subject. A "sirtuin-activating agent" refers to an agent that increases the activity or protein level of a sirtuin, either directly or indirectly, and includes sirtuin-activating compounds and sirtuin proteins and nucleic acids.

The term "therapeutic agent" is art-recognized and refers to any chemical moiety that is a biologically, physiologically, or pharmacologically active substance that acts locally or systemically in a subject. The term thus means any substance intended for use in the diagnosis, cure, mitigation, treatment or prevention of disease or in the enhancement of desirable physical or mental development and/or conditions in an animal or human.

The term "therapeutic effect" is art-recognized and refers to a local or systemic effect in animals, particularly mammals, and more particularly humans caused by a pharmacologically active substance. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions described herein may be administered in a sufficient amount to produce a at a reasonable benefit/risk ratio applicable to such treatment.

As used in reference to cognitive performance, the term "amount effective" is intended to mean an amount sufficient to improve cognitive performance or reduce the severity of an impairment in cognitive performance in a subject compared to a subject that is not administered the amount. Reduction in severity encompasses preventing, restraining, slowing, stopping, or reversing progression, severity, or a resultant symptom, including behavioral or physiological indicators, biochemical markers or metabolic indicators. Symptoms of impairment in cognitive performance include, for example, reduced mental functions, including learning, problem solving, remote memory, recent memory, word comprehension, orientation, attention span, calculation, abstract thinking, and judgment. A reduction in severity also includes a delay in the onset of symptoms in a subject susceptible to impairment of cognitive performance.

"Cognitive performance" refers to mental functions including, for example, learning (such as associative learning), problem solving, remote memory, recent memory, word comprehension, orientation, attention span, calculation, abstract thinking, and judgment. Cognitive functioning relates to the ability to learn, long and short term memory, memory consolidation, verbal and visual memory, recall, and visual reproduction. Cognitive function, in addition to memory, also includes reasoning, such as abstract reasoning; perception; and spatial orientation. As described herein, there are various tests known to those having skill in the art for determining whether an agent improves cognitive performance in a subject. Representative examples of such tests include Alzheimer's Disease Assessment Scale for cognitive function (ADAS-cogn.), Mini-Mental State Examination (MMSE), Clinician Interview Based Impression of Change (CIBIC) or CIBIC-plus and Global Deterioration, as further described herein.

"Associative learning" refers to learning connected to a positive or negative stimulus. It is a learning principle based on the belief that ideas and experiences reinforce one another and can be mentally linked to enhance the learning process (The American Heritzge Stedman's Medical Dictionary, $2^{nd}$ edition, 2004). Classical conditioning and operant conditioning are examples of associative learning. "Non-associative learning" is the opposite of associative learning, i.e., learning in which there is no conned stimulus. "Habituation" is an example of non-associative learning. "Habituated" refers to the reduction or elimination of the response to a stimulus upon frequent exposure.

As used herein, "cognitive function" is understood to mean "of or pertaining to the mental processes of perception, memory, judgment and reasoning" (Random House Dictionary, Unabridged, 2.sup.nd ed., Random House, NY 1987). See also, Taber's cyclopedic Medical Dictionary, F. A. Davison C. V., Philadelphia, 1989. The phrase "preventing deterioration of cognitive function" includes the prevention of deterioration of one of more of the following cognitive domains: orientation, attention and concentration, psychomotor speed and function, language and naming, verbal memory (immediate and delayed recall), category fluency, abstract reasoning and praxis (motor integration and executive control of complex learned movements). The prevention of deterioration of cognitive function can include prevention in patients not yet showing deterioration of cognitive function, and preferably, in patients who have shown deterioration in cognitive function.

One facet of cognitive function relates to learning and memory. The ability to learn relates a subject's capacity to acquire, retain or generalize specific skills or sets of information. A subject's ability to learn can be affected by deficiencies in attention, memory, perception or reasoning.

As described further below, the methods described herein may be useful to a healthy subject of any age (e.g., children, adolescents, adults and the elderly). A healthy subject is a subject who is not known to have any deficits in cognitive performance relative to its usual cognitive performance, as can be tested with any of the tests further described herein. Thus, the methods described herein may be useful to improve a cognitive function, such as to stimulate or enhance memory, both short term and long term, and learning ability in subjects that suffer no deficits, chronic deficits or temporary/acute deficits. The methods may also be used to treat a subject having or at risk of having a condition or disease that impairs cognitive performance.

For example, the methods described herein may be used to improve cognitive performance of a healthy subject. Such a subject may simply desire to improve its learning skills, memory or attention span, for example. In an illustrative embodiment, a subject who is preparing for an intellectual challenge, e.g., a test or exam, such as an aptitude test, may wish to increase its ability to learn and memorize. A method may thus comprise administering to a subject an agent described herein before and/or during the test. Administration may be a single dose or several doses of one or more sirtuin activating agents. Administration may be one or more months, weeks, days or hours prior to the test. A subject may be tested to confirm the efficiency of the sirtuin activating agent in the subject, e.g., by monitoring the level or activity of a sirtuin protein or a protein that is downstream of a sirtuin protein, or by determining cognitive performance in the subject before, during and/or after the treatment.

The methods described herein may also be used to prevent or compensate for a cognitive impairment that results from a particular condition or state of a subject. For example, the methods may be used to prevent or repair the cognitive decline, such as memory loss, that is normally associated with aging. Thus, a subject that is noticing a cognitive impairment may benefit from the administration of a sirtuin activating agent. The methods may also apply to older subjects even if they have not noticed a cognitive impairment. A subject may be a subject that is at least about 40, 50, 60, 70 or 80 years old. Such a subject may wish to receive a sirtuin activating agent on a daily, weekly, or monthly basis, for example. A subject may also take a test to measure cognitive function and receive a sirtuin activating agent based on the results of the test.

The methods described herein may also be used to counteract factors that cause an impairment in cognitive performance in a subject, for example, sleep deprivation. Adequate sleep sustains cognitive performance, while less than adequate sleep leads to a decrease in cognitive performance over time as described by Thorne et al., Military Systems, Defense and Civil Institute of Environmental Medicine (1983); Newhouse et al., Neuropsychopharmacology 2: 153-164 (1989); Newhouse et al., Military Psychology 4: 207-233 (1992), all of which are incorporated herein by reference in their entirety. Using computer-based cognitive performance tests, it has been shown that total sleep deprivation degrades human cognitive performance by approximately 25% for each successive period of 24 hours awake. Robust, cumulative decrements in cognitive performance occur during continuous total sleep deprivation as measured by computer-based testing and complex operational simulation. On fixed, restricted daily sleep amounts, cumulative reduced sleep also leads to a cognitive performance decline as described by Dinges et al., Sleep 20: 267-277 (1997), which is incorporated herein by reference. No other factor besides the amount of sleep contributes so substantially and consistently to the normal, daily variations in cognitive performance. Thus, the methods of the invention for improving cognitive performance can be useful in operational settings, both civilian and military, when sleep deprivation reduces productivity on cognitive tasks. For example, the invention methods can be used to improve cognitive performance in a subject in any setting where bouts of sleep deprivation or exhaustion are routinely encountered, for example, a commercial setting such as the airline or health care industry; a military setting; or a recreational setting such as an endurance athletic event. The invention can be practiced to compensate for a decline in cognitive performance as is associated with temporary as well as prolonged sleep deprivation, mental exhaustion, physical exhaustion or over-exertion. For example, the method can be useful to increase cognitive performance in an athlete undergoing a peak performance or endurance event, for example, a long run such as, for example, a half-marathon, marathon or triathlon.

In addition to sleep/wake history, cognitive performance varies with the time of day. When humans follow a nocturnal sleep/diurnal wake schedule, for example, an 8-hour sleep/16-hour wake cycle, with nightly sleep commencing at approximately midnight, body temperature reaches a minimum usually between 2:00 AM and 6:00 AM. Body temperature then begins rising to a maximum usually between 8:00 PM and 10:00 PM. Likewise, systematic studies of daily human cognitive performance rhythms show that speed of responding improves across the day to reach a maximum in the evening, usually between 8:00 PM and 10:00 PM, then dropping more rapidly to a minimum occurring in the early morning hours, usually between 2:00 AM and 6:00 AM. Similar but somewhat less consistent rhythms have been shown from testing based on various cognitive performance tasks. Thus, superimposed on the effect of total sleep deprivation on cognitive performance there can be a variation in cognitive performance over each 24-hour period. These variations may be lessened or eliminated with the methods described herein.

Various other factors have been shown to correlate with cognitive performance, including objective and subjective measures of sleepiness, drowsiness, and fatigue. For example, a relationship between excessive daytime sleepiness (EDS) and cognitive impairment has been reported by Ohayon and Vecchierini Arch Intern Med. 162: 201-208 (2002). These can also be prevented or compensated for by the methods described herein.

The methods described herein may also be used to counteract the impairment of cognitive performance associated with or resulting from exposure to a condition or to a drug, such as a legal or FDA approved drug (medication or medicament) or an illegal or non-FDA approved drug. For example, a subject to be treated as described herein may be a subject having a substance-induced cognitive decline. A substance may be a drug, such as a barbiturate or benzodiazepine, cocaine, amphetamine; alcohol; or an anesthetic, such as a general anesthetic, e.g., halothane, isoflurane and fentanyl. A method may comprise administering to a subject a sirtuin activating agent prior to, during and/or after exposure to the drug. Thus, for example, to counteract the effect of alcohol on cognitive performance, a sirtuin activating agent may be taken before the ingestion of alcohol, at the same time, and/or after the ingestion of alcohol. The methods may also be used to counteract the effect of trauma, such as brain or head trauma, such as resulting from surgery (e.g., temporal lobe brain surgery) or an accident; brain masses caused by tumors or infection, herpes encephalitis and other brain infections; stroke; ischemia, such as transient ischemic attack (TIA); transient global amnesia; or electroconvulsive therapy.

The methods described herein may also be used to prevent or counteract cognitive impairment resulting from a condition or disease, e.g., a chronic condition or disease, or an age-related condition or disease. Thus, methods described herein may be used for treating or preventing diseases or disorders. "Treating" a subject having a disease or disorder includes curing as well as ameliorating at least one symptom of any condition or disease or preventing a condition or disease from worsening. Exemplary diseases include neurodegenerative diseases and conditions of the central nervous system (CNS), such as Lewy body diseases, Alzheimer's disease, amyotrophic lateral sclerosis (ALS), Parkinson's Disease, Huntington's Chorea, senile dementia, Pick's disease, parkinsonism dementia syndrome, progressive subcortical gliosis, progressive supranuclear palsy, thalamic degeneration syndrome, hereditary aphasia, and myoclonus epilepsy.

Multiple sclerosis (MS), such as secondary or progressive MS, may also be treated, as well as its effects. Patients endure mild concentration or memory problems, while others experience depression, manic-depression, and paranoia. Other symptoms include sexual dysfunction, tremors, dizziness, slurred speech, trouble swallowing, urinary problems, and episodes of facial pain or inappropriate emotions.

Another condition that may be treated or prevented includes delirium. Delirium is a clinical state characterized by fluctuating disturbances in cognition, mood, attention, arousal, and self-awareness, which arises acutely, either without prior intellectual impairment or superimposed on chronic intellectual impairment (Merck Manual of Diagnosis and Therapy; merck.com). Delirium may be caused by a metabolic disease, a drug side effect, a structural lesion, or an infectious disease. For example, disorders causing delirium include anoxia, hyperkalemia, hyperparathyroidism, hyperthyroidism, hypoglycemia, hypokalemia, hypothyroidism, metabolic acidosis, postconcussion, postictal state, and transient ischemia. Drugs with anticholinergic properties such as antiemetics, antihistamines, antiparkinsonian drugs, antipsychotics, antispasmodics, muscle relaxants, tricyclic antidepressants may cause delirium. Other drugs that may cause delirium include alcohol, antihypertensives, benzodiazepines, cimetidine, digoxin, narcotics and other CNS depressants (merck.com).

Structural lesions that may cause delirium include vascular occlusion and cerebral infarction, subarachnoid hemorrhage, cerebral hemorrhage, primary or metastatic brain tumors, subdural hematomas, and brain abscesses. Most structural lesions can be detected by CT or MRI, and many produce focal neurologic signs observable during physical examination (merck.com).

Delirium may be caused by acute meningitis or encephalitis or by infections outside the brain, perhaps through the elaboration of toxins or production of fever. Pneumonia (even without impaired oxygenation), urinary tract infections, sepsis, or fever from viral infections can produce confusion in the vulnerable brain (merck.com).

Dementia is another condition that can be treated or prevented as described herein. Dementia is a chronic deterioration of intellectual function and other cognitive skills severe enough to interfere with the ability to perform activities of daily living (merck.com). Non-Alzheimer's dementias include Lewy body dementia, vascular dementia, Parkinson's disease, progressive supranuclear palsy, Huntington's disease (chorea), Pick's disease, frontal lobe dementia syndromes, normal-pressure hydrocephalus, subdural hematoma, Creutzfeld-Jakob disease, Gerstmann-Straussler-Scheinker disease (prion-related cause), general paresis and AIDS dementia. Other metabolic-toxic diseases causing dementia include anoxia, B12 deficiency, chronic drug-alcohol-nutritional abuse, folic acid deficiency, hypercalcemia associated with hyperparathyroidism, hypoglycemia, hypothyroidism, organ system failure, hepatic encephalopathy, respiratory encephalopathy, uremic encephalopathy and pellagra. Structural causes of dementia include Alzheimer's disease, ALS, brain trauma (acute severe), chronic subdural hematoma, dementia pugilistica, brain tumor, cerebellar degeneration, communicating hydrocephalus, Huntington's disease (chorea), irradiation to frontal lobes, MS, normal-pressure hydrocephalus, Parkinson's disease, Pick's disease, progressive multifocal leukoencephalopathy, progressive supranuclear palsy, surgery, vascular disease, multi-infarct dementia and Wilson's disease. Infectious causes of dementia include bacterial endocarditis, brain abscess, Creutzfeld-Jakob disease, Gerstmann-Straussler-Scheinker disease, HIV-related disorders, neurosyphilis (general paresis), tuberculous and fungal meningitis and viral encephalitis (merck.com).

Central nervous system disorders or diseases that may be treated include the following: (a) infectious Diseases of CNS:

Tetanus, Poliomyelitis and other nonarthropod-borne viral disease, Creutzfeldt-Jakob disease, Rabies, Meningitis (Bacterial, Viral, Other), Encephalitis, Brain abscess; (b) Degenerative/Hereditary Diseases of CNS, such as Alzheimer disease, Parkinson disease, ALS, movement disorders, such as Periodic limb movement and Restless Legs Syndrome, Ataxia, Dystonia, Multiple system atrophies (e.g., Shy-Drager syndrome), Myoclonus, TICS (involuntary muscle contractions), periodic limb movement disorder (PLMD), Tourette's syndrome, Tremor (e.g., essential tremor, resting tremor) and Wilson disease; (c) Other Diseases of CNS: Mental retardation, Quadriplegia and other paralytic syndromes, Seizure disorders, Cerebral palsy; (d) Vascular Diseases of CNS: Cerebral hemorrhage, Intracranial hemorrhage, Transient cerebral ischemia, Cerebrovascular disease, Occlusion/stenosis of precerebral/cerebral arteries; (e) Neoplasms: Malignant intracranial neoplasm, Malignant neoplasm of nervous system; and (f) Ill-defined Symptoms referable to the Nervous System: Migraine, Headache, delerium, Hallucinations Syncope and collapse, Dizziness/giddiness, Abnormal involuntary movement, Ataxia, Speech disturbance, and Sleep disorders.

The methods may also be used to treat learning disabilities, such as attention deficit disorders, e.g., hyperactivity disorder (ADHD), such as those that occur in children. Accordingly, subjects in need of treatment may be subjects that are between 1 and 18 years old, between 1 and 10 years old, or between 1 and 5 years old.

Other conditions or diseases that can be treated include frontal-temporal dementia, mood and anxiety disorders, post-traumatic stress disorder, depression, Schizophrenia, autism, anxiety, Down syndrome, panic attacks, binge eating, social phobia, an affective disorder, a psychiatric disorder, mild cognitive impairment, cognitive complaint patients, seizures, neurodegenerative illnesses, dementia, head trauma or injury, hysteria accompanied by confusion, cognitive disorders; age-related dementias; age-induced memory impairment; ion deficit disorder; psychosis; cognitive deficits associated with psychosis; and drug-induced psychosis.

A subject in need of therapy may be a subject having been diagnosed with an unusually low cognitive performance relative to, e.g., the subject's usual or optimal cognitive performance, or relative to the cognitive performance of an average subject. A subject in need of therapy may also be a subject who has been diagnosed as having or likely to develop a disease that is associated with or results in cognitive impairment, e.g., a neurodegenerative disease. A subject may also be a subject who has been determined as being likely to develop a disease, e.g., a subject having a form of a gene indicating susceptibility of developing the disease, or a subject in whose family the disease is more frequent than normally.

A method may comprise first determining the cognitive performance of a subject, and if the cognitive performance of the subject is lower than a control value, then administering to the subject a sirtuin-activating agent. A control value may be a value that corresponds to the usual cognitive performance of the subject. A control value may also be a value corresponding to the average cognitive performance of a group of control subjects of similar age to that of the subject.

A method may also comprise determining the cognitive performance of the subject after administration of a sirtuin-activating agent. For example a treatment may consist of the administration of several doses of the agent, and cognitive performance may be determined after administration of one or more doses of the agent. Cognitive performance may also be determined before and after administration of an agent.

A method may also comprise determining the level or activity of a sirtuin, either before, during and/or after the treatment. Methods for determining the level or activity of a sirtuin are known in the art.

Diagnosis and assessment of subjects having or at risk of having a cognitive impairment may be undertaken using any one of commonly used protocols for diagnosing, assessing and measuring the progression of these conditions. For example, to measure cognitive function, objective testing using standardized neuropsychological assessments with established normative values for nonclinical populations can be administered at baseline and at various times, e.g., after one or more hours, one or more days, one or more weeks, one or more months or one or more years. Cognitive performance can be assessed by testing the performance on a wide variety of tasks, for example, vigilance tasks and tasks requiring sustained attention. For vigilance and other tasks, accuracy can be used as the measure of cognitive performance, while other tasks use reaction time or its inverse, speed. Still others use a measure that is calculated as speed multiplied by accuracy, that is the amount of useful work performed per unit of time. The cognitive assessment measures that can be used include the Mini-Mental Status Exam (MMSE), the Modified Mini-Mental State Exam (3MS), Logical Memory, the Trail making Test (TMT) and other tests, e.g., those described herein.

The MMSE test is an 11-item (30 point) brief screening scale of cognitive status. Scores below 24 are generally recognized as reflecting significant cognitive impairment (Folstein, M., et al. (1975). "Mini-Mental State:" a practical method for grading the cognitive state of patients for the clinician. Journal of Psychiatric Research, 12: 189-198). Although the test is not sensitive to minor changes in cognitive performance, it provides a useful benchmark of overall cognitive functioning and can identify dramatic changes in cognitive performance that might indicate that the subject has developed new medical or neuropsychiatric conditions.

The Modified Mini-Mental State Examination (3MS) is a revision of the MMSE that includes four additional items (date and place of birth, word fluency, similarities, and delayed recall of words) to sample a wider range of cognitive abilities, an expanded range of scores from 30 to 100 to provide finer discrimination among subjects, and standardized testing and scoring procedures (Teng, E. & Chui, H. (1987). The modified mini-mental state (3MS) examination. Journal of Clinical Psychiatry, 48: 314-318). These modifications were made with the objective of improving the reliability and validity of the MMSE; recent publications support that the 3MS is psychometrically superior to the MMSE (Teng, E., Chui, H., and Gong, H. (1990). Comparisons between the Mini Mental Status Exam (MMSE) and its modified version—the 3MS test. In K. Hasegawa; Lamarre, C. and Patten, S. (1991). Evaluation of the Modified Mini Mental State Examination in a general psychiatric population. Canadian Journal of Psychiatry, 36: 507-511.; [0521] Grace, J., Nadler, J., White, D., et al. (1996). Folstein vs. Modified Mini-Mental State Examination in geriatric stroke: stability, validity, and screening utility. Archives of Neurology, 52: 477-484; Bravo, G. & Hebert, R. (1997). Reliability of the Modified Mini Mental State Examination in the context of a two-phase community prevalence study. Neuroepidemiology, 16:141-148; [0525] McDowell, I., Kristjansson, B., Hill, G., and Hebert, R. (1997). Community screening for dementia: The Mini Mental State Exam (MMSE) and the Modified Mini Mental State Exam (3MS) compared. Journal of Clinical Epidemiology, 50: 377-383). In a non-demented elderly population with an age range 65-69 yrs (N=2098), the mean score and standard deviation (sd) was 90.9 (7.6) (Bravo, G. & Hebert, R. (1997). Age- and education-specific reference values for the Mini-mental and Modified Mini-mental State Examinations derived from a nondemented elderly population. International Journal of Geriatric Psychiatry, 12: 1008-1018).

Empirical data from prospective, epidemiologic studies indicate the magnitude of change in the 3MS score in nondemented populations that could be considered clinically significant. A 5-point or greater decline in 3MS score over 3 yrs in the Cardiovascular Health Study was considered to represent a clinically significant change (Kuller, L., Shemanski, L., Manolio, T., et al. (1998). Relationship between ApoE, MRI findings, and cognitive function in the Cardiovascular Health Study. Stroke, 29: 388-398). In the Canadian Study of Health and Aging, a decline of 10-points (approximately 1 sd of the sample 3MS score) over the course of 5 yrs was considered clinically meaningful and correlated with differential rates of dementia and institutionalization (Maxwell, C., Hogan, D. and Ebly, E. (1999). Calcium-channel blockers and cognitive function in elderly people: results from the Canadian Study of Health and Aging. Canadian Medical Association Journal, 161: 501-506).

The Logical Memory I and II (Wechsler Memory Scale—Revised) (LMI and LMII) tests are standardized tests of verbal memory that examine the ability to recall ideas in two orally presented stories (Wechsler, D. (1987). Wechsler Memory Scale—Revised. San Antonio, Tex.: The Psychological Corporation). LMI is an assessment of immediate recall. LMII measures performance on delayed recall. Based on the standardization sample for the WMS-R, the mean score (and sd) norms for LMI and LMII by age group are: age 55-64: LMI=22.5 (6.3), LMII=18.1 (6.0); age 65-69: LMI=22.0 (7.4), LMII=16.8 (8.1); age 70-74: LMI=20.9 (7.3), LMII 14.7 (9.2) (Wechsler, 1987). In a community dwelling, cognitively unimpaired population with a mean age of 79 yrs (N=234), the mean score (sd) on LMI was 21.3 (6.1) and on LMII was 15.3 (7.6). For those with mild cognitive impairment (MCI; N=76), the mean score on LMI was 12.7 (5.2) and on LMII was 4.2 (5.2) (Petersen, R., et al. (1999). Mild cognitive impairment: clinical characterization and outcome. Archives of Neurology, 56: 303-308).

The Trail Making Test Parts A & B is an assessment of psychomotor speed and function as well as attention, concentration, sequencing, and mental flexibility. Scores are determined by the time required for completion (max=30 sec). In a non-demented population with age range 60-69 years (N=61), the mean (sd) for Trails A was 35.8 sec (11.9) and for Trails B was 81.2 sec (38.5) (Spreen, R. & Strauss, E. (1998). A compendium of neuropsychological tests (2.sup.nd Ed.), pp. 533-547. New York: Oxford University Press).

The 21-item Alzheimer's Disease Assessment Scale (ADAS) is a performance-based scale which includes 11 items to assess cognitive function, e.g. memory and orientation, (ADAS-Cog) and 10 items to assess non-cognitive function, e.g. mood state and behavioral changes, (ADAS-Noncog). A score between 0 and 70 is possible on the cognitive part of the scale, where 0 means the patient made no errors at all and 70 means the patient is profoundly demented. In practice, however, a healthy individual will probably score between 5 and 10. The scale therefore clearly spans the full range of cognitive from normal to terminally demented. The 11 cognitive items include spoken language ability, comprehension of spoken language, recall of test instructions, word-finding difficulty in spontaneous speech, following commands, naming objects and fingers, constructional praxis, ideational praxis, orientation, word-recall task and word-recognition task. The word-recall task is administered first and then the following 10 minutes are spent in an open-ended conversation in order to assess the various other aspects of language. The remaining cognitive tasks are then administered. (alzheimer-insights.com)

The CIBIC-Plus is rated on a scale from 1 (marked improvement) to 7 (marked worsening); a rating of 4 denotes no change.

The Global Deterioration Scale (GDS) provides caregivers an overview of the stages of cognitive function for those suffering from a primary degenerative dementia such as Alzheimer's disease. It is broken down into 7 different stages. Stages 1-3 are the pre-dementia stages. Stages 4-7 are the dementia stages. Beginning in stage 5, an individual can no longer survive without assistance. Within the GDS, each stage is numbered (1-7), given a short title, i.e., Forgetfulness, Early Confusional, etc. followed by a brief listing of the characteristics for that stage. Caregivers can get a rough idea of where an individual is at in the disease process by observing that individual's behavioral characteristics and comparing them to the GDS (see geriatric-resources.com).

The Brief Cognitive Rating Scale (BCRS) is an assessment tool to be used with the Global Deterioration Scale (GDS) to help stage a person suffering from a primary degenerative dementia such as Alzheimer's disease. Developed by Dr. Barry Reisberg, this assessment tool tests 5 different areas known as Axis (4 cognitive and 1 functional). For the first 4 axis, the tester will ask a variety of questions to determine the level of impairment. The results of the 5th axis (Functioning) are determined primarily by observation. Tester can use the Functional Assessment Staging test (FAST) for a more accurate assessment. After a score is determined for each Axis, total the results and divide by 5. This answer will result in a stage corresponding on the GDS (see geriatric-resources.com).

Under FAST, a person at stage 1 has no difficulties, either subjectively or objectively; a person at stage 2 has complains of forgetting location of objects; subjective word finding difficulties only; a person at stage 3 has decreased job functioning evident to coworkers; difficulty in traveling to new locations; a person at stage 4 has decreased ability to perform complex tasks (e.g., planning dinner for guests; handling finances; marketing); a person at stage 5 requires assistance in choosing proper clothing for the season or occasion; a person at stage 6a has difficulty putting clothing on properly without assistance; a person at stage 6b is unable to bathe properly; may develop fear of bathing and will usually require assistance adjusting bath water temperature; a person at stage 6c has an inability to handle mechanics of toileting (i.e., forgets to flush; doesn't wipe properly); a person at stage 6d has urinary incontinence, occasional or more frequent; a person at stage 6e has fecal incontinence, occasional or more frequent; a person at stage 7a has an ability to speak limited to about half a dozen words in an average day; a person at stage 7b has intelligible vocabulary limited to a single word in an average day; a person at stage 7c is nonambulatory (unable to walk without assistance); a person at stage 7d is unable to sit up independently; a person at stage 7e is unable to smile; and a person at stage 7f is unable to hold his/her head up.

Those skilled in the art understand that vigilance tasks are appropriate measures of cognitive performance under conditions of sleep deprivation, and that either reaction time (speed) or some measure that takes reaction time into account is a valid and reliable way of measuring cognitive performance. These and other measures of cognitive performance known in the art can be useful to confirm improvement in cognitive performance by the invention methods.

The Multiple Sleep Latency Test (MSLT) is a widely accepted objective measure of sleepiness/alertness and can also be useful to predict or assess an impairment in cognitive performance. In the MSLT, individuals try to fall asleep while lying in a darkened, quiet bedroom. Various physiological measures used to determine sleep or wakefulness are recorded, for example, eye movements, brain activity and muscle tone, and the amount of time taken to reach the first 30 seconds of stage 1 (light) sleep is determined. Shorter latencies to stage 1 are considered to indicate greater sleepiness (lower alertness). Sleep latencies under 5 minutes are considered to be pathological and indicative of a sleep disorder or sleep deprivation. During both total and partial sleep deprivation, alertness and cognitive performance decline. Thus, there is a correlation between MSLT-determined sleepiness/alertness and cognitive performance, such that the MSLT as well as other tests known in the art for alertness as well as other features of cognitive performance, for example, can be useful to determine whether the application of the invention method for improving cognitive performance is indicated.

Subjective measures of alertness also have been shown to correlate with cognitive performance and can be used to predict cognitive performance impairments. As with the MSLT, during both total and partial sleep deprivation, scores on the Stanford Sleepiness Scale (SSS) increase. Similar to the MSLT, subjective tests such as the SSS-determined alertness can be used to predict or assess impairments in cognitive performance. Some other examples of subjective measures of sleepiness/alertness include the Epworth Sleepiness Scale as described by Johns, Chest 103: 30-36 (1993); the Karolinska Sleepiness scale as described by Akerstedt and Gillberg, International Journal of Neuroscience 52: 29-37 (1990). These and other tests known in the art that can be used to assess features of cognitive performance are useful to assess or predict an impairment in cognitive performance and to determine whether an indication exists to practice the methods provided by the invention.

Cognitive tests may also be computer based.

The methods described herein may allow a person to improve on any of the cognitive tests, such as to move from one stage to another stage characterizing a higher cognitive function. A subject may also move by more than one stage or by one or more points on a scale, depending on the particular test. A successful treatment may be demonstrated by a change in stages or number of points in a particular test, relative to the normal expectation resulting from the disease or condition. A treatment may also be considered successful if a person stays at the same stage of a test for a longer period of time than expected considering the person's health status.

The methods may comprise administering one or more sirtuin activating agents together or sequentially. Sirtuin activating agents may be administered on a chronic basis or in a single dose depending on the situation.

Sirtuin activating agents may also be administered to a subject with one or more other agents. Other agents may include anti-oxidants, such as vitamin C; beta glucans; epigallocatechin gallate; Proanthocyanidin B2; Alpha Lipoic Acid (ALA), N-Acetyl-Cysteine (NAC), Dimethylglycine (DMG), Co-enzym Q (CoQ 10), S-Adenosylmethionine (SamE), L-Glutathione, L-Carnitine or Acetyl-L-Carnitine, Green Tea., Milk Thistle, Gingko, DHEA, Curcumin, Grape Seed, Melatonin; Vitamin A, D & E, L-Carnitine, Acetyl-L-Carnitine, Thalidomide, Ketotifen, Lactoferrin, Alpha or Omega Interferon, cytokines, Korean Ginseng; dimethylglycine (DMG), glucosamine hydrochloride, methyl sulfonyl methane, elemental magnesium; arctigenin, boswellic acid, flavonoids, emodin, e icosapentaenoic acid (EPA), docosahexanoic acid (DHA), HIV drugs such as Abacavir, Lamivudine, Tenofovir, Emtricitabine, Didanosine, Lecithin; and 2-bromo-2-nitropropane-1,3 diol (BNPD). Other agents may also be agents that stimulate alertness, e.g., caffeine or theine. Other agents may also be agents used to treat a condition or disease that causes cognitive impairment, e.g., an agent for treating Alzheimer's disease. These other agents may be administered at the same time or at a different time than the sirtuin activating agent. Accordingly, compositions comprising a sirtuin activating agent and another agent are also provided herein.

Also provided herein are methods for identifying an agent that enhances a cognitive function in a subject. A method may comprise (i) identifying an agent that increases the level or activity of a sirtuin and (ii) testing the agent identified in (i) in an animal model of cognitive function, such as those described herein. Other animal models to test cognition are: Morris Water Maze test; passive avoidance test; active avoidance test; place (preference) conditioning; T-Maze test; Y-Maze test; Radial arm maze; Hole-board test; Novel object recognition test; Barnes Maze; pre-pulse inhibition of startle; home cage observation; rotarod; and instrumental learning paradigms such as skinner maze. References for such tests are set forth below: Morris Water Maze test (Morris et al. Nature, 1982, 297 (5868), 618); passive avoidance test (Davis et al. Pharmacol Biochem Behav. 1976, 4(1):13); active avoidance test (Handwerker et al. Brain Res. 1974, 75(2):324); place (preference) conditioning (Swerdlow et al. Psychopharmacology (Berl). 1984, 84(2):163); T-Maze test (Takahashi et al. Neurosci Lett. 2005 3; 380(3):270); Y-Maze test (Dore et al. Neurotoxicol Teratol. 2001, 23(5):463); Radial arm maze (Goodale et al. Behav Brain Res. 1981, 3(2):273); Hole-board test (File et al. Psychopharmacologia. 1975, 44(1):47); Novel object recognition test (Ennaceur et al. Behav Brain Res. 2005, 159(2):247 and Lee et al. Eur J. Neurosci. 2003, 18(6): 1660); Barnes Maze (Dennes et al. Psychopharmacology (Berl). 1993; 111(4):435); pre-pulse inhibition of startle (Davis et al. Pharmacol Biochem Behav. 1975, 3(5):861) and Breier A. Br J Psychiatry Suppl. 1999; (37):16); rotarod (Sharma et al. J. Neurosci. 2005, 25(22):5351); operant learning paradigms such as skinner maze (Skinner B F. Science and human behavior (1953) New York: McMillan and MacDonell et al. Alcohol. 1987; 22(3):285); Pavlovian fear conditioning (Fanselow M S Neuron, 1998, 20, (4), 625 and Hamann et al. Neuropsychologia, 40, (8) 11187); Inhibitory avoidance test (Vianna et al. Proc Natl Acad Sci USA. 2001 Oct. 9; 98(21):12251).

Pharmaceutical Compositions and Methods

Compounds, nucleic acids, proteins, cells and other compositions can be administered to a subject according to methods known in the art. For example, nucleic acids encoding a protein or an antisense molecule can be administered to a subject as described above, e.g., using a viral vector. Cells can be administered according to methods for administering a graft to a subject, which may be accompanied, e.g., by administration of an immunosuppressant drug, e.g., cyclosporin A. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000.

Pharmaceutical agents for use in accordance with the present methods may be formulated in conventional manner using one or more physiologically acceptable carriers or excipients. Thus, proteins and nucleic acids described herein as well as compounds or agents that increase the protein or expression level of nucleic acids described herein, and their physiologically acceptable salts and solvates may be formulated for administration by, for example, injection, inhalation or insufflation (either through the mouth or the nose) or oral, buccal, parenteral or rectal administration. In one embodiment, the agent is administered locally, e.g., at the site where the target cells are present, such as by the use of a patch.

Agents can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the agents can be formulated in liquid solutions, preferably in physiologically compatible buffers such as Hank's solution or Ringer's solution. In addition, the agents may be formulated in solid form and redissolved or suspended immediately prior to use. Lyophilized forms are also included.

Agents may be administered systemically or peripherally or parenterally, e.g., by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal, and intrasternal injection and infusion.

Kits

Also provided herein are kits, e.g., kits for therapeutic purposes. A kit may comprise one or more sirtuin activating agents, e.g., compounds, such as those described herein. A kit may optionally comprise devices for administering the compounds to subjects and instructions for use. Devices include syringes, stents and other devices for introducing a compound into a subject or applying it to the skin of a subject.

All publications, patents, patent applications, and GenBank Accession numbers mentioned herein are hereby incorporated by reference in their entirety as if each individual publication or patent was specifically and individually indicated to be incorporated by reference. In case of conflict, the present application, including any definitions herein, will control.

The present invention is further illustrated by the following examples which should not be construed as limiting in any way.

EXAMPLES

Example 1

Resveratrol Facilitates Associative Learning

Learning is a process by which organisms alter and adapt their behavior in response to environmental stimuli. As such learning and memory are mechanisms that are ultimately important for the organisms survival and its biological fitness. In a number of pathological situations, including Alzheimer's disease, lewy body diseases, mood and anxiety disorders but also during normal aging cognitive processes such as learning and memory are impaired. It is therefore desirable to identify components that would enhance cognitive function.

Resveratrol (3,5,4'-tri-hydroxystilbene) is a phytoalexin naturally occurring in plants and is present in high concentrations in the skin of grapes and in wine. Trans-resveratrol has been shown to have free radical scavenger property and prevents oxidative damage in numerous in vitro and in vivo studies (Pervaiz, 2003). Recently it has been reported that resveratrol is a potent agonist of the Sirt1 deacetylase thereby expanding the lifespan of yeast and metazoans (Howitz et al., 2003; Wood et al., 2004).

Here we report that resveratrol facilitates associative learning in mice. We furthermore show that application of resveratrol attenuates risk factors that impair learning and memory such as ethanol or expression of p25, a protein implicated with various neurodegenerative diseases (Cruz and Tsai, 2004). These data demonstrate that resveratrol can enhance cognitive function and prevent cognitive decline when neuroplasticity is challenged.

A fundamental type of learning is associative learning that can be analyzed in rodents using the pavlovian fear conditioning paradigm (Fendt and Fanselow, 1999; Fischer et al., 2003). As fear conditioning is a robust and commonly used method to analyze learning and allows to delineate the involvement of distinct brain structures in the learning process, we choose this paradigm to investigate the effect of reveratrol on learning.

The principle of Pavlovian fear conditioning is as follows. During the training procedure mice are exposed to a novel context (context 1), consisting of an observation chamber with defined lightning, odor, background noise and geometry. After exploring this novel environment for 180 s the animals are exposed to a tone for 30 s followed by a mild electric foot shock for 2 s. On the basis of associative learning mice display aversive freezing behavior during a memory test consisting of re-expose to the conditioning context 24 h after the training. The specificity of the associated memory is demonstrated by the finding that mice show no freezing behavior when exposed to a different context (context 2). Tone-dependent fear memories can be analyzed by presenting the tone in context 2. Freezing is an inborn behavior that rodents express in threatening situations. It is defined as the complete absence of movement, except respiration and heartbeat. Whereas mice display no freezing behavior during training, a significant increase of freezing behavior is observed upon re-exposure to the conditioned context only. Therefore, freezing behavior is commonly used to quantify the amount of learning.

C57BL/6J mice were anesthetized and microcannula (PlasticOne; AP −0 mm, lateral 1 mm, depth 2 mm) were implanted into the lateral brain ventricles (icv). In the first experiment mice were subjected to single icv. injection's of resveratrol (5 µg/mouse) or vehicle (30% DMSO/aCSF; artificial cerebrospinal fluid) for 7 consecutive days. The animals were trained by context- and tone-dependent fear conditioning 24 h after the last icv. injection and memory retention was analyzed the following day (see FIG. 1A). Resveratrol injected animals showed significantly increased freezing behavior during the context- and tone-dependent memory test when compared to the vehicle group, showing that learning and memory was facilitated by resveratrol (FIG. 1B). Importantly, daily injection of resveratrol did not affect explorative behavior or pain sensation (FIG. 1C) indicating that resveratrol specifically affected memory consolidation.

Figure 2:
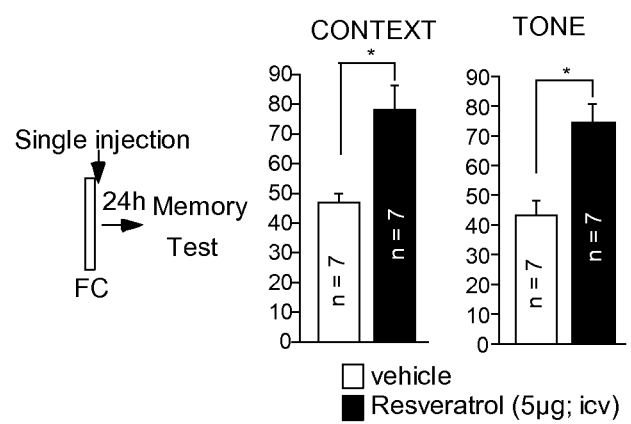
FIG. 2. A single icv. injection of resveratrol facilitates memory consolidation. Left: Experimental design. Right: Freezing behavior during the memory test of mice that were injected icv. with resveratrol or vehicle during immediately after context- and tone dependent fear conditioning. Resveratrol injected mice showed significantly enhanced freezing when compared to the vehicle group *P<0.05 vs. vehicle.

To test the acute effect of resveratrol on learning and memory mice were subjected to context- and tone-dependent fear conditioning. In this experiment resveratrol (5 µg/mouse) or vehicle (30% DMSO in aCSF) was injected into the lateral brain ventricles (i.c.v) immediately after the training (FIG. 2). The mice were tested for memory retention 24 h later by re-exposure to the conditioning context. Resveratrol injected animals showed significantly increased freezing behavior during the context- and tone-dependent memory test when compared to the vehicle group. These results showed that memory consolidation was facilitated by a single injection of resveratrol after the training (FIG. 2).

Figure 3:
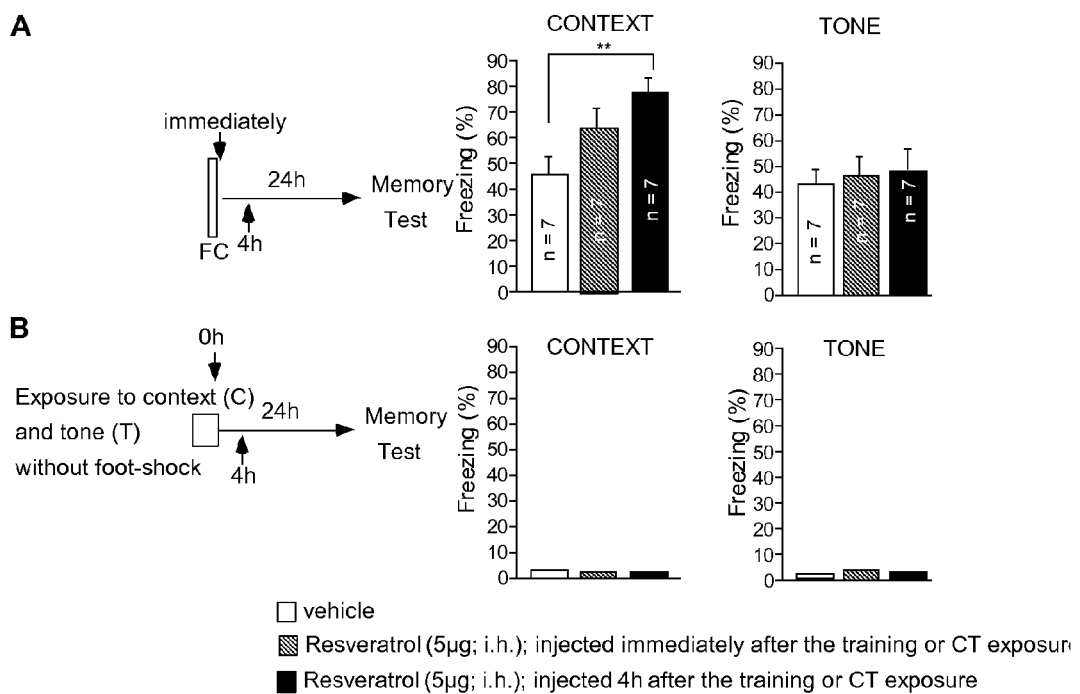
FIG. 3. Intra-hippocampal injection of resveratrol facilitates context-dependent associative learning. A. Left: Experimental design. Right: Freezing behavior of experimental groups during the context and tone-dependent memory test. B. Left: Experimental design. Mice (n=6/group) were mock-fear conditioned by exposure to the context and tone that was not followed by the foot shock. Right: Freezing behavior of experimental groups during the context and tone-dependent memory test. **P<0.01 vs. vehicle. As mice injected with vehicle either immediately or 4 h after the training performed indistinguishable only the 4 h vehicle group is shown here.

Context-dependent fear conditioning requires the hippocampus whereas tone-dependent fear conditioning relies on an intact amygdala (Kim and Fanselow, 1992). To test whether resveratrol facilitated learning by modulating hippocampal function, microcannula were implanted into the dorsal hippocampus (i.h.; AP −1.5 mm, lateral 1 mm, depth 2 mm) of mice that were trained by context- and tone-dependent fear conditioning 5 days post-surgery. Resveratrol (5 µg/mouse) or vehicle (30% DMSO in aCSF) was injected i.h. immediately or 4 h after the training. The latter group showed significantly enhanced freezing behavior during the context-dependent memory test when compared to vehicle-injected animals. Freezing during the tone-dependent memory test was not different among groups (FIG. 3A). Taken into account that the hippocampus is not required for tone-dependent fear learning this finding further shows that resveratrol specifically facilitating associative learning and does not affect freezing behavior per se. This view is supported by the finding that i.h. injection of resveratrol did not affect freezing behavior when mice where subjected to a mock-training procedure consisting of context-tone-exposure that was not followed by the aversive foot shock (FIG. 3B).

These results demonstrated that resveratrol facilitated learning and memory in mice under normal conditions. We further asked whether resveratrol would prevent cognitive decline in response to factors that impair learning.

Example 2

Figure 4:
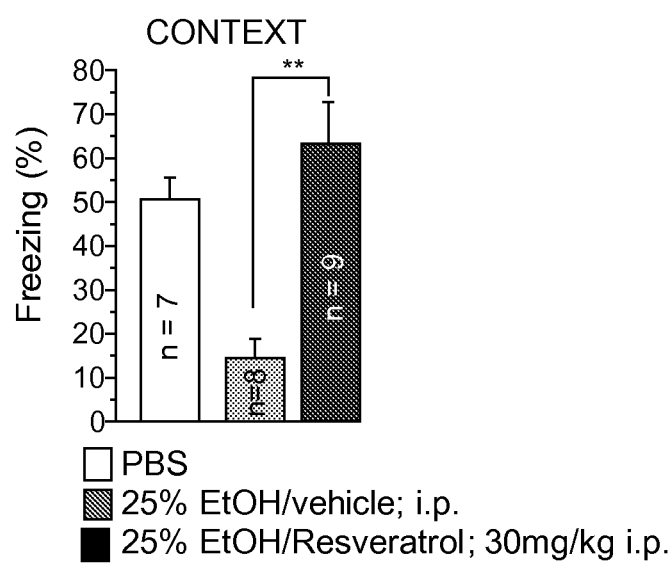
FIG. 4. Resveratrol prevents ethanol-induced impairment of learning. Mice were subjected to context-dependent fear conditioning and injected (ip.) with ethanol, ethanol resveratrol or PBS immediately afterwards. While ethanol severe impaired freezing during the memory test, resveratrol attenuated this effect. **P<0.01.

Resveratrol Prevents Cognitive Decline in Response to Factors that Impair Learning It was previously shown that administration of ethanol (by ip injection) severely disrupts the acquisition of context-dependent fear memories (Melia et al., 1996). This effect was not due to ethanol-induced changes in motivational state or state-dependent learning but to impaired neuronal activity. To this end we trained mice by context-dependent fear conditioning and injected (ip.) ethanol (33% ethanol/PBS) or ethanol and resveratrol (30 mg/kg resveratrol in 33% ethanol/PBS) immediately afterwards. In agreement with previous studies, ethanol injected mice displayed impaired freezing behavior during the context-dependent memory test, demonstrating that learning was severely impaired. In contrast, mice injected with ethanol and resveratrol performed indistinguishable to mice injected only with PBS. Thus, these findings show that resveratrol prevents ethanol induced decrease of learning and memory in mice (FIG. 4).

Figure 5:
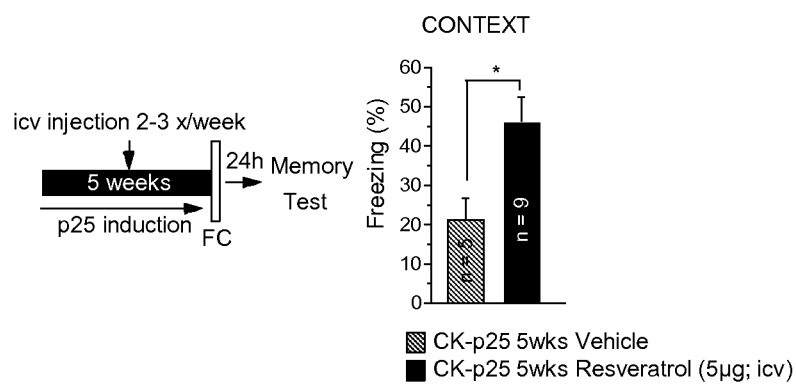
FIG. 5. Resveratrol prevents p25 mediated impaired learning. Left: Experimental design. Right: Freezing behavior of 5 week-induced CK-p25 mice injected with resveratrol or vehicle.

The p25 protein is generated by proteolytic cleavage of the Cdk5 activator p35. P25 leads to aberrant Cdk5 activity and has been implicated with neurodegenerative diseases (Cruz and Tsai, 2004). Bi-transgenic animals, expressing p25 in a targeted and region-restricted manner in the forebrain (CK-p25 mice), develop severe cognitive deficits after prolonged p25 production (Fischer et al., submitted). As such, fear conditioning is dramatically impaired when p25 is expressed for 6 weeks. To analyze whether resveratrol can attenuate p25-mediated cognitive decline p25 expression was induced in CK-p25 for 5 weeks while 2-3×/week the animals were injected icv. with either resveratrol (5 µg/mouse) or vehicle (30% DMSO/aCSF). Subsequently the animals were fear conditioned and tested for memory retention 24 h later. In contrast to vehicle injected CK-p25 mice, freezing behavior was significantly enhanced in the resveratrol group, demonstrating that resveratrol injection prevents cognitive decline in response to p25 expression (FIG. 5).

In summary our data demonstrate that resveratrol facilitates learning and memory in mice and attenuates the maladaptive effect of risk factors that otherwise would impair cognitive function. Thus, resveratrol is a promising drug to treat patients that suffer form from cognitive dysfunction.

REFERENCES

Cruz et al. (2004). Curr Opin Neurobiol 14, 390-394; Fendt et al. (1999) Neurosci Biobehav Rev 23, 743-760; Fischer et al. (2003) Curr Drug Targets CNS Neurol Disord 6, 375-381; Howitz et al. (2003) Nature 425, 191-196; Kim et al. (1992) Science 256, 675-677; Melia et al. (1996) Neuroscience 74, 313-322; Pervaiz, S. (2003) FASEB J 17, 1975-1985; Wood et al. (2004) Nature 430, 689-689.

Example 3

SIRT1 Overexpressing Mice Show Improved Learning 4.5 months old transgenic mice overexpressing SIRT1 under the control of the doxycycline-inducible Cre system (Beard et al. (2006) Genesis 44:23) were submitted to the fear conditioning paradigm. In a first experiment, we evaluated the capacity of the mice to associate (remember) the context with the electric shock we gave during the training phase, an ability that is regulated by hippocampus. In a second experiment, we evaluated the capacity of the mice to associate the electric shock with the previous stimulus—an alarm noise—that we gave before the electro shock, an ability that is related to the amygdala function.

The results of the first experiment show that about 40% (from about 30-50%) of the wildtype mice and about 48% (from about 38-58%) of the SIRT1 overexpressing mice froze.

The results of the second experiment show that, whereas only about 30% of wildtype mice froze after a freezing stimulus, about 60% of the SIRT1 overexpressing mice froze.

EQUIVALENTS

Those skilled in the art will recognize, or be able to ascertain using no more than routine experimentation, many equivalents of the specific embodiments described herein. Such equivalents are intended to be encompassed by the following claims.

The invention claimed is:

1. A method for improving cognitive performance in a mammalian subject, comprising
   (i) determining the cognitive performance of a mammalian subject;
   (ii) comparing the cognitive performance of the mammalian subject to a control value; and
   (iii) administering to the mammalian subject a SIRT1-activating agent if the cognitive performance of the mammalian subject is lower than the control value, wherein the SIRT1-activating agent is a non-naturally occurring compound, and wherein the SIRT1-activating agent is not a stilbene, flavone or flavonoid.

2. The method of claim 1, wherein the control value is a value that corresponds to the usual cognitive performance of the mammalian subject or is a value of the average cognitive performance of a group of control mammalian subjects of similar age to that of the mammalian subject.

3. The method of claim 1, wherein the SIRT1-activating agent is administered orally.

4. The method of claim 1, further comprising administering to the mammalian subject another agent.

5. The method of claim 4, wherein the other agent is an anti-oxidant.

6. The method of claim 1, wherein the mammalian subject is a human.

* * * * *